United States Patent
Grompe et al.

(10) Patent No.: US 9,000,257 B2
(45) Date of Patent: Apr. 7, 2015

(54) FUMARYLACETOACETATE HYDROLASE (FAH)-DEFICIENT PIGS AND USES THEREOF

(75) Inventors: Markus Grompe, Portland, OR (US); Scott Nyberg, Rochester, MN (US); Joseph Lillegard, Rochester, MN (US); Raymond Hickey, Portland, OR (US)

(73) Assignees: Oregon Health & Science University, Portland, OR (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/642,213

(22) PCT Filed: Mar. 23, 2011

(86) PCT No.: PCT/US2011/029659
§ 371 (c)(1),
(2), (4) Date: Oct. 19, 2012

(87) PCT Pub. No.: WO2011/133284
PCT Pub. Date: Oct. 27, 2011

(65) Prior Publication Data
US 2013/0191931 A1    Jul. 25, 2013

Related U.S. Application Data

(60) Provisional application No. 61/326,931, filed on Apr. 22, 2010.

(30) Foreign Application Priority Data

Sep. 22, 2010   (JP) .................. 2010-212896

(51) Int. Cl.
| | | |
|---|---|---|
| *C12N 5/071* | (2010.01) | |
| *G01N 33/50* | (2006.01) | |
| *A01K 67/027* | (2006.01) | |
| *A61K 49/00* | (2006.01) | |
| *C12N 15/861* | (2006.01) | |

(52) U.S. Cl.
CPC ............ *C12N 5/067* (2013.01); *A01K 67/0271* (2013.01); *A01K 67/0276* (2013.01); *A61K 49/0008* (2013.01); *C12N 5/0672* (2013.01); *C12N 15/861* (2013.01); *G01N 33/5067* (2013.01); *G01N 33/5008* (2013.01); *A01K 2207/12* (2013.01); *A01K 2207/15* (2013.01); *A01K 2217/075* (2013.01); *A01K 2227/108* (2013.01); *A01K 2267/025* (2013.01); *A01K 2267/03* (2013.01)

(58) Field of Classification Search
CPC ........... A01K 67/0271; A01K 67/0276; A01K 2207/12; A01K 2207/15; A61K 49/0008; C12N 5/067; C12N 5/0672; C12N 12/861; G01N 33/5008
See application file for complete search history.

(56) References Cited

U.S. PATENT DOCUMENTS

2007/0134212 A1*  6/2007  Beschorner et al. ....... 424/93.21

FOREIGN PATENT DOCUMENTS

| WO | WO 2008/151283 | 12/2008 |
| WO | WO 2010/127275 | 11/2010 |

OTHER PUBLICATIONS

Ekser et al., Transplant Immunology 2009, 21:87-92.*
Azuma et al., "Robust Expansion of Human Hepatocytes in Fah$^{-/-}$/Rag2$^{-/-}$ Il2rg$^{-/-}$ Mice," *Nature Biotech.*, vol. 25(8):903-910, 2007.
Li et al., N-Nitrosodiethylamine-Induced Pig Liver Hepatocellular Carcinoma Model: Radiological and Histopathological Studies, *Cardiovasc. Intervent. Radiol.*, vol. 29:420-428, 2006.
Paulk et al., Adeno-Associated Virus gene Repair Corrects a Mouse Model of Hereditary Tyrosinemia In Vivo, *Hepatology*, vol. 51:1200-1208, 2010.
Rogers et al., "Disruption of the CFTR Gene Produces a Model of Cystic Fibrosis in Newborn Pigs," *Science* vol. 321:1837-1841, 2008.
Shafritz, "A Human Hepatocyte Factory," *Nature Biotech.*, vol. 25(8):871-872, 2007.
Welsh et al., "Development of a Porcine Model of Cystic Fibrosis," *Trans Am Clin Climatol Assoc* vol. 120:149, 2009.

* cited by examiner

*Primary Examiner* — Doug Schultz
(74) *Attorney, Agent, or Firm* — Klarquist Sparkman, LLP

(57) ABSTRACT

Described herein is the generation of Fah$^{+/-}$ heterozygote pigs by homologous recombination and somatic cell nuclear transfer, and a method for producing Fah$^{-/-}$ homozygote pigs. The Fah-deficient pigs of the disclosure can be used for a variety of research and therapeutic purposes, such as for the expansion of human hepatocytes, and as large animal models of hereditary tyrosinemia type 1, cirrhosis and hepatocellular carcinoma.

15 Claims, 9 Drawing Sheets

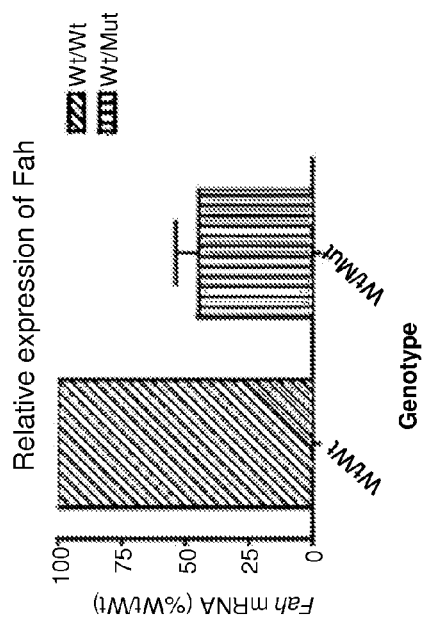
FIG. 8A
FIG. 8B
FIG. 8C
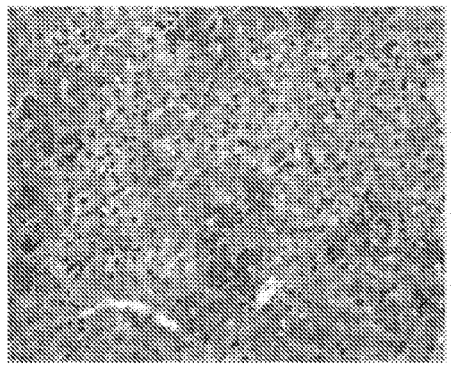
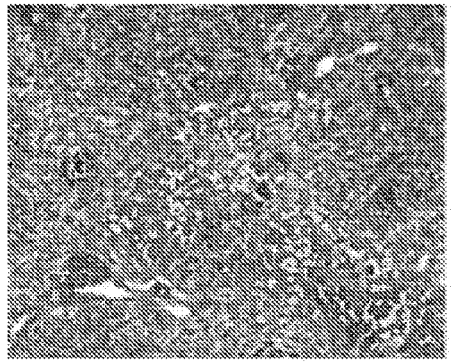
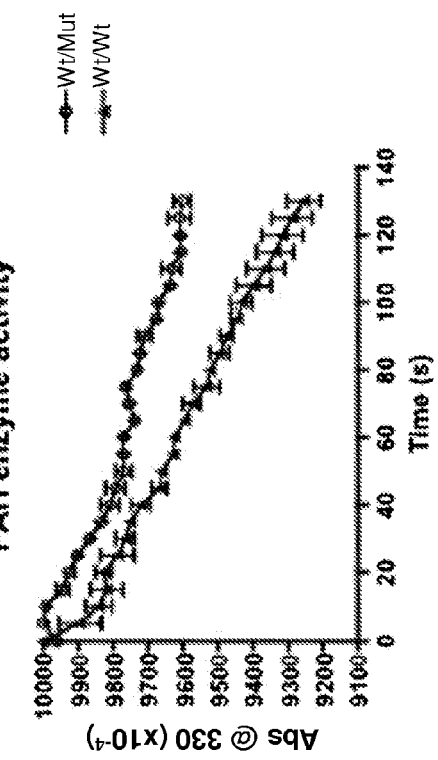
FIG. 8D
FIG. 8E
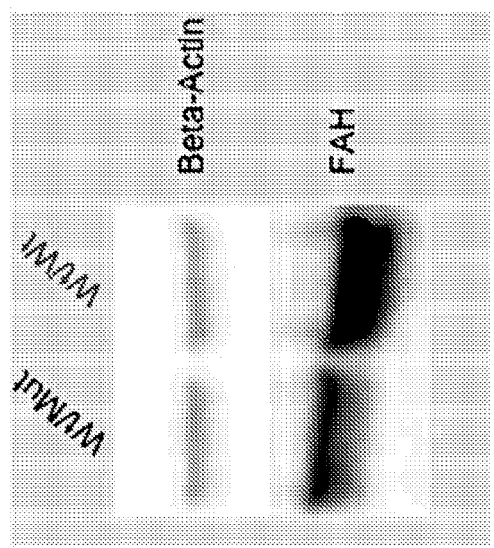

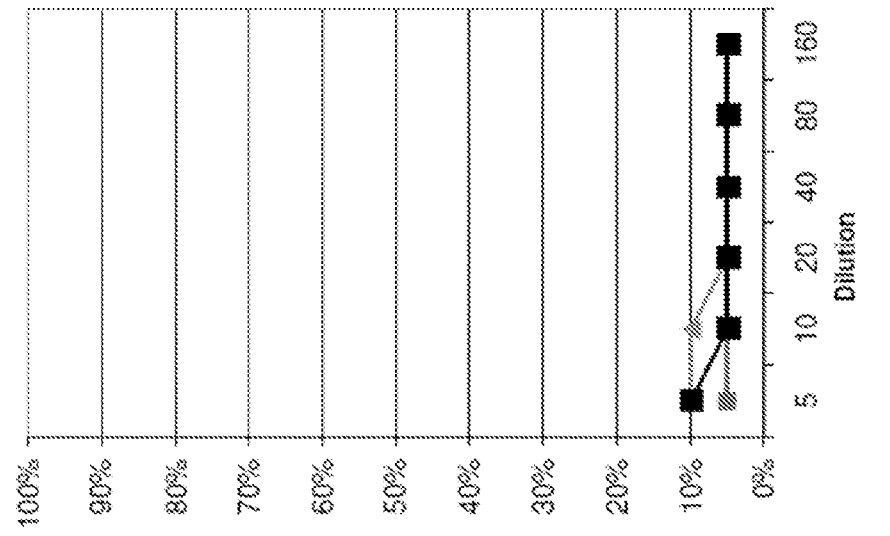
FIG. 9A Group 1 -Tolerize/-Priming
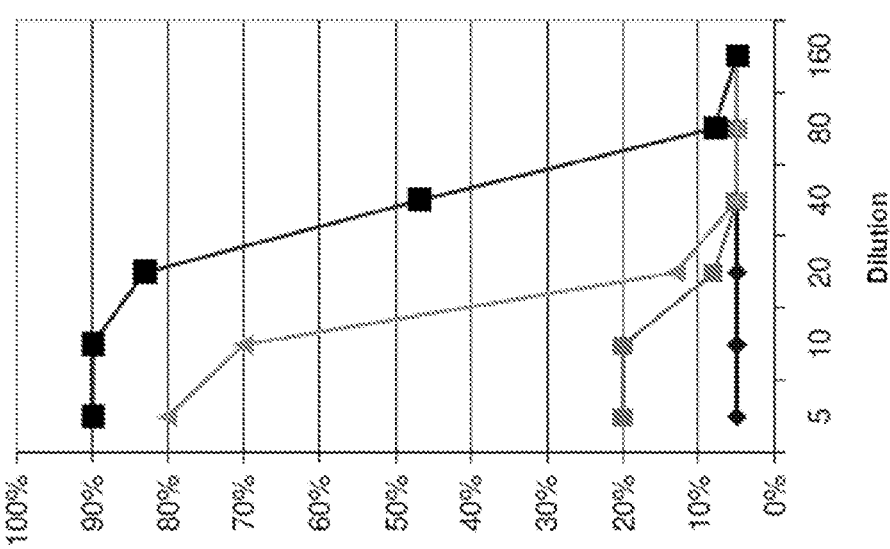
FIG. 9B Group 2 -Tolerize/+Priming
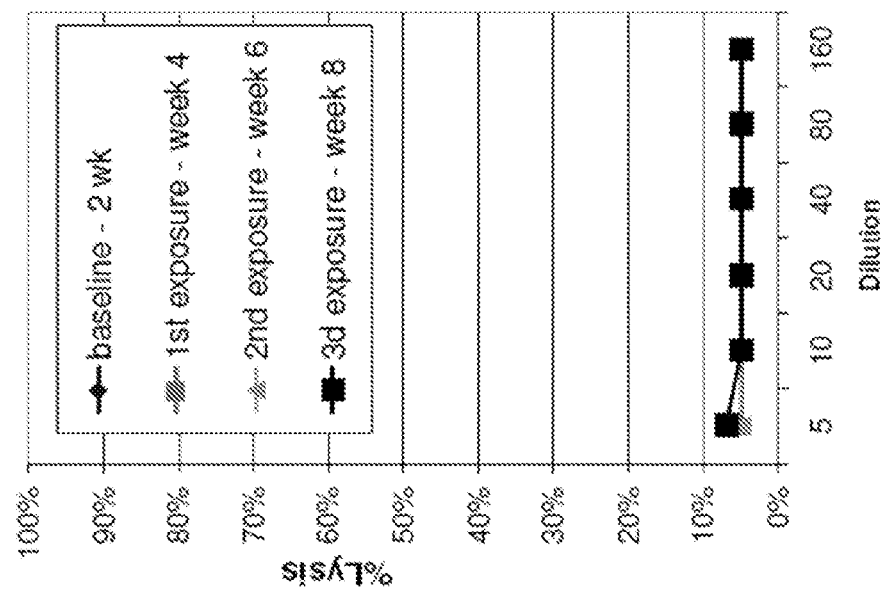
FIG. 9C Group 3 +Tolerize/+Priming

FUMARYLACETOACETATE HYDROLASE (FAH)-DEFICIENT PIGS AND USES THEREOF

CROSS REFERENCE TO RELATED APPLICATIONS

This is the U.S. National Stage of International Application No. PCT/US2011/029659, filed Mar. 23, 2011, which was published in English under PCT Article 21(2), which claims the benefit of U.S. Provisional Application No. 61/326,931, filed Apr. 22, 2010, and Japan Application No. 2010-212896, filed Sep. 22, 2010, both which are herein incorporated by reference in their entirety.

STATEMENT OF GOVERNMENT SUPPORT

This invention was made with government support under DK086070 awarded by the National Institutes of Health. The government has certain rights in the invention.

FIELD

This disclosure concerns Fah-deficient pigs and their use. This disclosure also relates to a method of expanding hepatocytes from other species, including humans, in Fah-deficient pigs.

BACKGROUND

The liver is the principal site for the metabolism of xenobiotic compounds including medical drugs. Because many hepatic enzymes are species-specific, it is necessary to evaluate the metabolism of candidate pharmaceuticals using cultured primary human hepatocytes or their microsomal fraction (Brandon et al. *Toxicol. Appl. Pharmacol.* 189:233-246, 2003; Gomez-Lechon et al. *Curr. Drug Metab.* 4:292-312, 2003). While microsomal hepatocyte fractions can be used to elucidate some metabolic functions, other tests depend on living hepatocytes. Some compounds, for example, induce hepatic enzymes and thus their metabolism changes with time. To analyze enzyme induction, hepatocytes must be not only viable, but fully differentiated and functional.

Human hepatocytes are widely used by the pharmaceutical industry during preclinical drug development. Their use is mandated by the FDA as part of drug development. For drug metabolism and other studies, hepatocytes are typically isolated from cadaveric organ donors and shipped to the location where testing will be performed. The condition (viability and state of differentiation) of hepatocytes from cadaveric sources is highly variable and many cell preparations are of marginal quality. The availability of high quality human hepatocytes is further hampered by the fact that they cannot be significantly expanded in tissue culture (Runge et al. *Biochem. Biophys. Res. Commun.* 274:1-3, 2000; Cascio S. M., *Artif. Organs* 25:529-538, 2001). After plating, the cells survive but do not divide. Hepatocytes from readily available mammalian species, such as the mouse, are not suitable for drug testing because they have a different complement of metabolic enzymes and respond differently in induction studies. Immortal human liver cells (hepatomas) or fetal hepatoblasts are also not an adequate replacement for fully differentiated adult cells. Human hepatocytes are also necessary for studies in the field of microbiology. Many human viruses, such as viruses which cause hepatitis, cannot replicate in any other cell type.

Moreover, bioartificial liver assist devices, which use hepatocytes ex vivo, have been used to support patients in acute liver failure. In addition, several clinical trials of hepatocyte transplantation have been carried out, which provided proof-of-principle that hepatocyte transplantation can be beneficial. Currently, human hepatocytes cannot be expanded significantly in culture. Hepatocytes derived from stem cells in culture are immature and generally lack full functionality. Therefore, all hepatocytes in use today are derived from human donors, either cadaveric or surgical specimens, which significantly limits hepatocyte availability. If enough human hepatocytes were available, bioartificial liver assist devices would become a viable technology and human hepatocyte transplantation could find wide-spread use. Given these limitations, methods of expanding primary human hepatocytes are highly desirable.

SUMMARY

Described herein are Fah-deficient pigs, which have utility for a variety of purposes, including for the expansion of hepatocytes from other species (particularly humans), and as a large animal model of liver diseases, including cirrhosis, hepatocellular carcinoma and hepatic infection. Although a Fah-deficient mouse model has been previously described, the Fah-deficient pig offers significant advantages, particularly for the expansion of human hepatocytes as the number of hepatocytes that can be expanded in mice is limited due to their small size. Moreover, Fah-deficient mice fail to recapitulate all of the key features of the human disease hereditary tyrosinemia type I (HT1), which results from a deficiency in the FAH enzyme. The Fah-deficient pig disclosed herein provides a large animal model of human HT1 disease and represents the first large animal model of HCC arising spontaneously in the background of cirrhosis.

Provided herein are methods of expanding human hepatocytes in vivo. In some embodiments, the method includes transplanting human hepatocytes into a Fah-deficient pig and allowing the human hepatocytes to expand. In some cases, the Fah-deficient pig is immunosuppressed. Alternatively or in addition, human cells can be transplanted into a Fah-deficient pig fetus before thymic development in order to induce immunological tolerance to human cells, including hepatocytes. Thus, in some embodiments, the method of expanding human hepatocytes in vivo includes transplanting human hepatocytes into a Fah-deficient pig fetus and allowing the human hepatocytes to expand following birth of the Fah-deficient pig. In some examples, the Fah-deficient pig fetus is surgically externalized to transplant the human hepatocytes.

Isolated hepatocytes (such as human hepatocytes) expanded in and collected from Fah-deficient pigs are also provided.

Also provided is a genetically modified pig whose genome is homozygous for a disruption in the Fah gene such that the disruption results in loss of expression of functional FAH protein, wherein the pig exhibits decreased liver function. In some examples, the Fah-deficient pig further includes transplanted human hepatocytes. In some cases, the Fah-deficient pig is immunosuppressed. In some cases, the Fah-deficient pig has been pre-natally tolerized to human cells. A genetically modified pig heterozygous for a disruption in the Fah gene is also provided.

Also provided is a method for selecting an agent effective for the treatment of a human liver disease by administering a candidate agent to a Fah-deficient pig and assessing the effect of the candidate agent on the liver disease. An improvement in one or more signs or symptoms of the liver disease, indicates the candidate agent is effective for the treatment of the liver disease.

Further provided is a method for selecting an agent effective for the treatment of infection by a human hepatic pathogen by administering a candidate agent to a Fah-deficient pig transplanted with human hepatocytes, wherein the transplanted human hepatocytes in the Fah-deficient pig are infected with the hepatic pathogen; and assessing the effect of the candidate agent on the hepatic infection.

A method for selecting an agent effective for the treatment of cirrhosis by administering a candidate agent to a Fah-deficient pig and assessing the effect of the candidate agent on at least one diagnostic marker of cirrhosis in the Fah-deficient pig is also provided. In this method, the Fah-deficient pig has been administered NTBC (or a similar compound, such as another pharmacologic inhibitor of phenylpyruvate dioxygenase, for example methyl-NTBC) at a dose that results in development of cirrhosis in the pig. Further provided is a method for selecting an agent effective for the treatment of hepatocellular carcinoma (HCC) by administering a candidate agent to a Fah-deficient pig and assessing the effect of the candidate agent on HCC in the Fah-deficient pig. In this method, the Fah-deficient pig has been administered NTBC (or a similar compound) at a dose that results in development of HCC in the pig.

A method of assessing the effect of an exogenous agent on human hepatocytes in vivo is also provided. In some embodiments, the method includes administering the exogenous agent to a Fah-deficient pig; and measuring at least one marker of liver function in the Fah-deficient pig.

Further provided are methods of evaluating gene therapy protocols and vectors for the liver (including gene expression and gene knockdown vectors); drug metabolism, pharmacokinetics, efficacy, toxicology and safety; and human genetic liver diseases. Such methods can utilize Fah-deficient pigs transplanted with human hepatocytes, or human hepatocytes that have been expanded in and collected from Fah-deficient pigs.

The foregoing and other objects, features, and advantages of the invention will become more apparent from the following detailed description, which proceeds with reference to the accompanying figures.

BRIEF DESCRIPTION OF THE FIGURES

FIG. 8A is an image of an H&E stained section of liver from a Fah-null heterozygote piglet (magnification ×125). The liver histology is normal. FIG. 8B is an immunohistochemistry image of FAH protein detected using a rabbit anti-FAH polyclonal antibody in a formalin-fixed liver section from a Fah-null heterozygote piglet (magnification ×200). There is characteristic FAH staining in the hepatocytes. FIG. 8C is a graph showing that there is a 55% reduction (average=55.3%, standard error=0.09) of Fah gene expression in heterozygotes compared to wild-type siblings by qPCR analysis. Fah gene expression is compared to expression of the housekeeping gene beta-actin (Actb). Error bars represent standard error, n=2. FIG. 8D shows a Western blot using a polyclonal rabbit anti-FAH antibody, imaged using a chemiluminescent substrate for detection of the HRP-conjugated secondary antibody. Thirty µg of protein lysate was added for each sample. There is a decrease of FAH protein in the liver lysates from Fah-null heterozygote piglets when compared to wild-type littermates. FIG. 8E is a graph showing FAH enzyme activity is reduced in Fah-null heterozygote piglets. The absorbance of FAA at 330 nm is plotted on the Y-axis and time in seconds is plotted on the X-axis. Error bars represent standard error, n=2.

FIGS. 9A-9C are graphs showing the results of a cytotoxicity assay to evaluate tolerance to human cells induced in piglets by fetal exposure to human mesenchymal stem cells.

SEQUENCE LISTING

Figure 1:
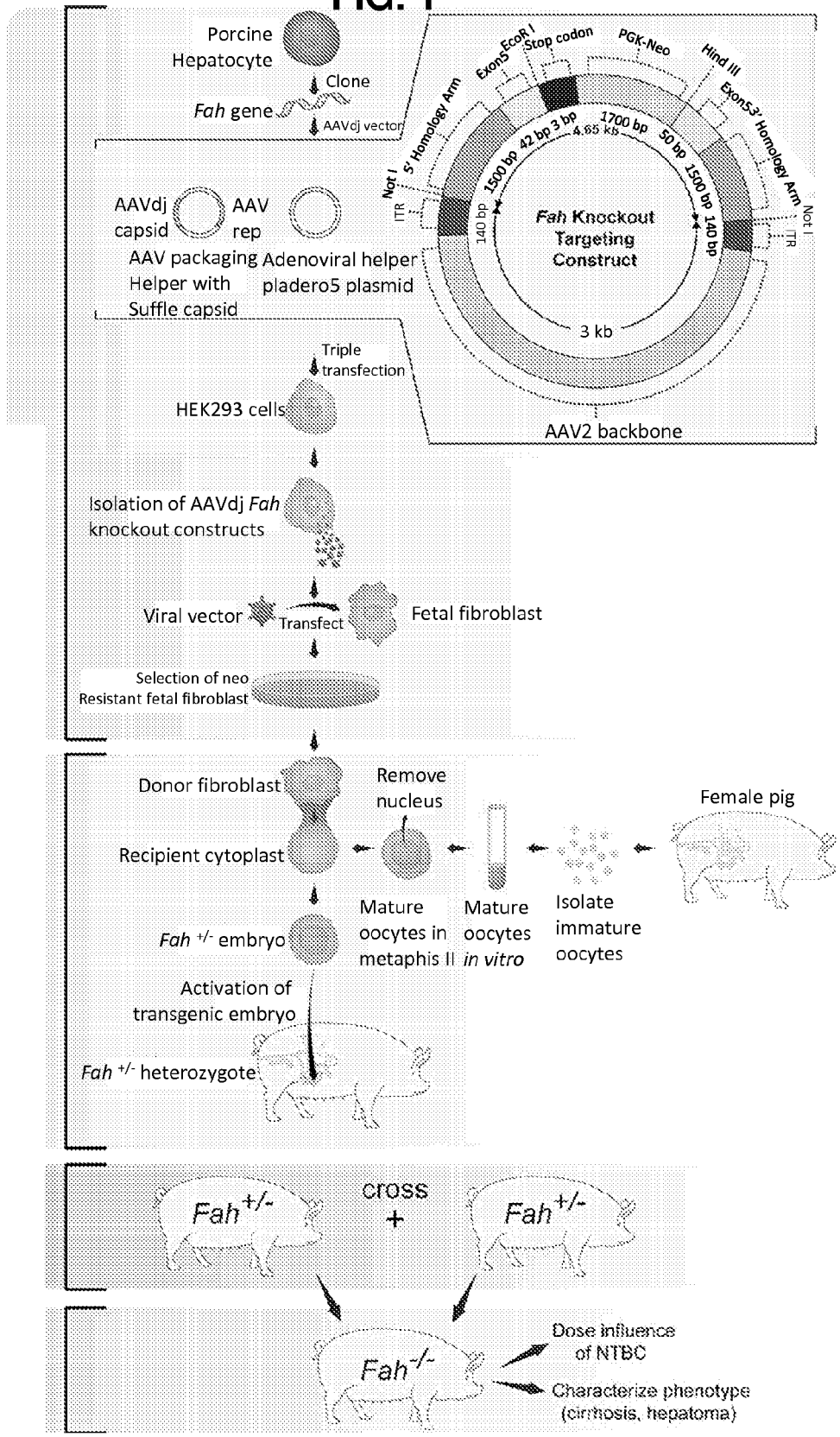
FIG. 1 is a schematic illustration of the procedure used to generate Fah-deficient pigs.
Figure 2A:
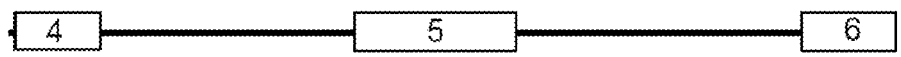
FIGS. 2A-2E are a series of gene constructs that illustrate the porcine Fah gene disruption procedure: (A) Genomic Fah locus with exons 4, 5 and 6. (B) PCR procedure to generate genomic homology arms 5' and 3' to exon 5. The exon 5 primer for the 5' amplification contains a tail with an in-frame stop codon (TGA), as well as a restriction site for cloning in the PGK-neo (neomycin-phosphotransferase resistance gene) cassette. Similarly, the exon 5 primer for the 3' fragment also contains a restriction site. (C) Targeting cassette. (D) Targeting cassette cloned into an AAV-DJ vector. The intended recombination event is depicted. The ITR loops are shown. (E) Structure of the targeted locus after recombination. The stop codon and neo-cassette have been inserted into exon 5. The PCR primers used for detecting correct recombination are shown. Importantly, one primer is placed outside the homology contained within the targeting vector and the other is placed within the PGK-neo cassette.
Figure 2B:
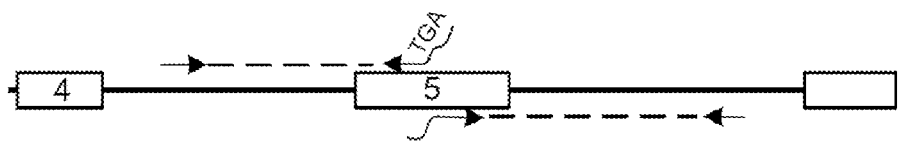
Figure 2C:
Figure 2D:
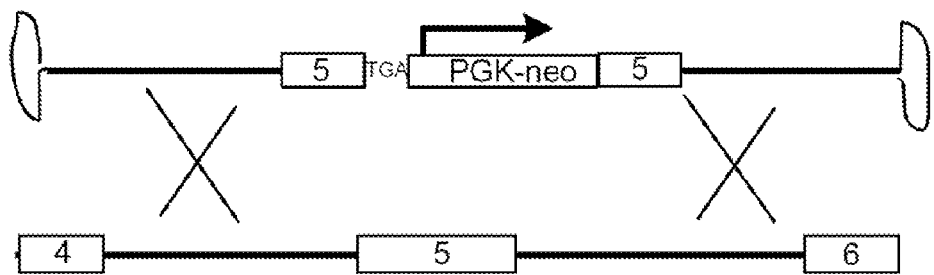
Figure 2E:
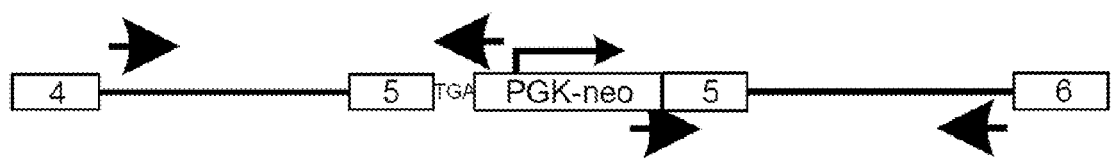

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. The Sequence Listing is submitted as an ASCII text file, created on Oct. 15, 2012, 35.7 KB, which is incorporated by reference herein. In the accompanying sequence listing:

SEQ ID NO: 1 is the nucleotide sequence of a 20 kb region of the pig Fah gene.

SEQ ID NO: 2 is the nucleotide sequence of the Fah gene targeting construct.

SEQ ID NOs: 3-20 are nucleotide sequences of PCR primers.

DETAILED DESCRIPTION

I. Abbreviations

AAV Adeno-associated virus
ADSC Adipose tissue-derived stem cell
ALT Alanine aminotransferase
AST Aspartate aminotransferase
CMV Cytomegalovirus
DNA Deoxyribonucleic acid
ES Embryonic stem
FACS Fluorescence activated cells sorting
FAH Fumarylacetoacetate hydrolase
FSH Follicle stimulating hormone
gDNA Genomic DNA
HBV Hepatitis B virus
HCC Hepatocellular carcinoma
HCG Human chorionic gonadotropin
HCV Hepatitis C virus
hMSC Human mesenchymal stem cells
HT1 hereditary tyrosinemia type 1
iPS Induced pluripotent stem
IPSC Induced pluripotency stem cells
ITR Inverted terminal repeat
IVF In vitro fertilization
MOI Multiplicity of infection
mTOR Mammalian target of rapamycin
NTBC 2-(2-nitro-4-trifluoro-methyl-benzoyl)-1,3 cyclohexanedione
PCR Polymerase chain reaction
SA Succinylacetone
SCNT Somatic cell nuclear transfer

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Agent that inhibits or prevents the development of liver disease: A compound or composition that when administered to a Fah-deficient animal, prevents, delays or inhibits the development of liver disease in the animal. Liver disease or liver dysfunction is characterized by any one of a number of signs or symptoms, including, but not limited to an alteration in liver histology (such as necrosis, inflammation, fibrosis, dysplasia or hepatic cancer), an alteration in levels of liver-specific enzymes and other proteins (such as aspartate aminotransferase, alanine aminotransferase, bilirubin, alkaline phosphatase and albumin), plasma or urinary succinylacetone (SA), or generalized liver failure. In some embodiments, the agent that inhibits liver disease is a pharmacologic inhibitor of phenylpyruvate dioxygenase, such as 2-(2-nitro-4-trifluoro-methyl-benzoyl)-1,3 cyclohexanedione (NTBC) or methyl-NTBC. In one non-limiting example, the agent that inhibits liver disease is NTBC.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (scFvs) that bind to a target protein (or an epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that can stimulate the production of antibodies or a T-cell response in an animal, including compositions that are injected or absorbed into an animal. An antigen reacts with the products of specific humoral or cellular immunity. A "pathogen-specific antigen" is an antigen, such as a protein, expressed by a pathogen, such as a virus, bacteria or parasite that elicits an immune response in a subject.

Azathioprine: An immunosuppressant that is a purine synthesis inhibitor, inhibiting the proliferation of cells, especially leukocytes. This immunosuppressant is often used in the treatment of autoimmune diseases or organ transplant rejection. It is a pro-drug, converted in the body to the active metabolites 6-mercaptopurine (6-MP) and 6-thioinosinic acid. Azathioprine is produced by a number of generic manufacturers and as branded names (Azasan™ by Salix; Imuran™ by GlaxoSmithKline; Azamun™; and Imurel™).

Biological sample: A sample obtained from cells, tissue or bodily fluid of a subject, such as peripheral blood, serum, plasma, cerebrospinal fluid, bone marrow, urine, saliva, tissue biopsy, surgical specimen, and autopsy material. Also referred to herein as a "sample."

Cirrhosis: Refers to a group of chronic liver diseases characterized by loss of the normal microscopic lobular architecture and regenerative replacement of necrotic parenchymal tissue with fibrous bands of connective tissue that eventually constrict and partition the organ into irregular nodules. Cirrhosis has a lengthy latent period, usually followed by sudden abdominal pain and swelling with hematemesis, dependent edema, or jaundice. In advanced stages there may be ascites, pronounced jaundice, portal hypertension, varicose veins and central nervous system disorders that may end in hepatic coma.

Collecting: As used herein, "collecting" expanded human hepatocytes refers to the process of removing the expanded hepatocytes from an animal that has been injected or transplanted with isolated human hepatocytes (also referred to as a recipient animal). Collecting optionally includes separating the hepatocytes from other cell types. In one embodiment, the expanded human hepatocytes are collected from the liver of a Fah-deficient animal. In some examples, the expanded human hepatocytes are collected from the liver of a Fah-deficient pig.

Common-γ chain of the interleukin receptor (Il2rg): A gene encoding the common gamma chain of interleukin receptors. Il2rg is a component of the receptors for a number of interleukins, including IL-2, IL-4, IL-7 and IL-15 (Di Santo et al. *Proc. Natl. Acad. Sci. U.S.A.* 92:377-381, 1995). Animals deficient in Il2rg exhibit a reduction in B cells and T cells and lack natural killer cells. Also known as interleukin-2 receptor gamma chain.

Cryopreserved: As used herein, "cryopreserved" refers to a cell (such as a hepatocyte) or tissue that has been preserved or maintained by cooling to low sub-zero temperatures, such as 77 K or −196° C. (the boiling point of liquid nitrogen). At these low temperatures, any biological activity, including the biochemical reactions that would lead to cell death, is effectively stopped.

Cyclosporin A: An immunosuppressant compound that is a non-ribosomal cyclic peptide of 11 amino acids produced by the soil fungus *Beauveria nivea*. Cyclosporin A is used for the prophylaxis of graft rejection in organ and tissue transplantation. Cyclosporin A is also known as cyclosporine and ciclosporin.

Decreased liver function: An abnormal change in any one of a number of parameters that measure the health or function of the liver. Decreased liver function is also referred to herein as "liver dysfunction." Liver function can be evaluated by any one of a number of means well known in the art, such as, but not limited to, examination of liver histology and measurement of liver enzymes or other proteins. For example, liver dysfunction can be indicated by necrosis, inflammation, fibrosis, oxidative damage or dysplasia of the liver. In some instances, liver dysfunction is indicated by hepatic cancer, such as hepatocellular carcinoma. Examples of liver enzymes and proteins that can be tested to evaluate liver dysfunction include, but are not limited to, alanine aminotransferase (ALT), aspartate aminotransferase (AST), bilirubin, alkaline phosphatase and albumin. Liver dysfunction also can result in generalized liver failure. Procedures for testing liver function are well known in the art, such as those taught by Grompe et al. (*Genes Dev.* 7:2298-2307, 1993) and Manning et al. (*Proc. Natl. Acad. Sci. U.S.A.* 96:11928-11933, 1999).

Deficient: As used herein, "Fah-deficient" or "deficient in Fah" refers to an animal, such as a pig, comprising a disruption in the Fah gene (such as an insertion, deletion or one or more point mutations), which results in a substantial decrease in, or the absence of, Fah mRNA expression and/or functional FAH protein. As used herein, the term "loss of expression" of functional FAH protein does not refer to only a complete loss of expression, but also includes a substantial decrease in expression of functional FAH protein, such as a decrease of about 80%, about 90%, about 95% or about 99%. In some embodiments, the Fah-deficient animal comprises homozygous insertions in the Fah gene (such as an insertion that includes an in-frame stop codon). In some embodiments, the insertion is in exon 5 of Fah. In some embodiments, the Fah-deficient animal comprises homozygous deletions in the Fah gene. As one example, the homozygous deletion is in exon 5 of Fah. In another embodiment, the Fah-deficient animal comprises one or more point mutations in the Fah gene. Examples of suitable Fah point mutations are known in the art (see, for example, Aponte et al. *Proc. Natl. Acad. Sci. U.S.A.* 98(2):641-645, 2001).

Deplete: To reduce or remove. For example, "macrophage depletion" refers to the process of eliminating, removing, reducing or killing macrophages in an animal. An animal that has been depleted of macrophages is not necessarily completely devoid of macrophages but at least exhibits a reduction in the number or activity of macrophages. In one embodiment, macrophage depletion results in at least a 10%, at least a 25%, at least a 50%, at least a 75%, at least a 90% or a 100% reduction in functional macrophages.

Disruption: As used herein, a "disruption" in a gene refers to any insertion, deletion or point mutation, or any combination thereof. In some embodiments, the disruption leads to a partial or complete loss of expression of mRNA and/or functional protein.

Embryonic stem (ES) cells: Pluripotent cells isolated from the inner cell mass of the developing blastocyst. ES cells are pluripotent cells, meaning that they can generate all of the cells present in the body (bone, muscle, brain cells, etc.). Methods for producing murine ES cells can be found in U.S. Pat. No. 5,670,372. Methods for producing human ES cells can be found in U.S. Pat. No. 6,090,622, PCT Publication No. WO 00/70021 and PCT Publication No. WO 00/27995. Also contemplated herein are induced pluripotent stem cells (iPS cells), which are a type of pluripotent stem cell artificially derived from a non-pluripotent cell (such as an adult somatic cell) by inducing expression of certain genes, such as OCT3/4, SOX2, NANOG, LIN28, Klf4, and/or c-Myc (Yu et al., *Science* 318(5858):1917-1920, 2007; Takahashi et al., *Cell* 131(5):861-872, 2007). Thus far, iPS cells from mouse (Okita et al., *Nature* 448(7151):313-317, 2007), human (Yu et al., *Science* 318(5858):1917-1920, 2007; Takahashi et al., *Cell* 131(5):861-872, 2007), rat (Li et al., *Cell Stem Cell* 4(1):16-19, 2009), monkey (Liu et al., *Cell Stem Cell* 3(6):587-590, 2008) and pig (Esteban et al., *J. Biol. Chem. Epub Apr. 21,* 2009) have been reported.

Engraft: To implant cells or tissues in an animal. As used herein, engraftment of human hepatocytes in a recipient animal refers to the process of human hepatocytes becoming implanted in the recipient animal following injection. Engrafted human hepatocytes are capable of expansion in the recipient animal.

Expand: To increase in quantity. As used herein, "expanding" human hepatocytes refers to the process of allowing cell division to occur such that the number of human hepatocytes increases.

Fetus: The unborn offspring of an animal in the postembryonic period.

FK506: FK506, also known as tacrolimus or fujimycin, is an immunosuppressant drug. FK506 a 23-membered macrolide lactone first discovered in the fermentation broth of a Japanese soil sample that contained the bacteria *Streptomyces tsukubaensis*. This compound is often used after allogeneic organ transplant to reduce the activity of the patient's immune system and lower the risk of organ rejection. FK506 reduces T-cell and interleukin-2 activity. It is also used in a topical preparation in the treatment of severe atopic dermatitis (eczema), severe refractory uveitis after bone marrow transplants, and the skin condition vitiligo.

Fludarabine: A purine analog that inhibits DNA synthesis. Fludarabine is often used as a chemotherapeutic drug for the treatment of various hematologic malignancies.

Fumarylacetoacetate hydrolase (FAH): A metabolic enzyme that catalyzes the last step of tyrosine catabolism. Mice having a homozygous deletion of the Fah gene exhibit altered liver mRNA expression and severe liver dysfunction (Grompe et al. *Genes Dev.* 7:2298-2307, 1993). Point mutations in the Fah gene have also been shown to cause hepatic failure and postnatal lethality (Aponte et al. *Proc. Natl. Acad. Sci. U.S.A.* 98(2):641-645, 2001). Humans deficient for Fah develop the liver disease hereditary tyrosinemia type 1 (HT1) and develop liver failure. Fah deficiency leads to accumulation of fumarylacetoacetate, a potent oxidizing agent and this ultimately leads to cell death of hepatocytes deficient for Fah. Thus, Fah-deficient animals can be repopulated with hepatocytes from other species, including humans.

Gestation: The period of development from conception (fertilization of an oocyte) to birth. The gestation period for a pig is (on average) 112-115 days.

Hepatic pathogen: Refers to any pathogen, such as a bacterial, viral or parasitic pathogen, that infects cells of the liver. In some embodiments, the hepatic pathogen is a "hepatotropic virus" (a virus that targets the liver), such as HBV or HCV.

Hepatocellular carcinoma (HCC): HCC is a primary malignancy of the liver typically occurring in patients with inflammatory livers resulting from viral hepatitis, liver toxins or hepatic cirrhosis.

Hepatocyte: A type of cell that makes up 70-80% of the cytoplasmic mass of the liver. Hepatocytes are involved in protein synthesis, protein storage and transformation of carbohydrates, synthesis of cholesterol, bile salts and phospholipids, and detoxification, modification and excretion of exogenous and endogenous substances. The hepatocyte also initiates the formation and secretion of bile. Hepatocytes manufacture serum albumin, fibrinogen and the prothrombin group of clotting factors and are the main site for the synthesis of lipoproteins, ceruloplasmin, transferrin, complement and glycoproteins. In addition, hepatocytes have the ability to metabolize, detoxify, and inactivate exogenous compounds such as drugs and insecticides, and endogenous compounds such as steroids.

Hereditary tyrosinemia type 1 (HT1): Tyrosinemia is an error of metabolism, usually inborn, in which the body cannot effectively break down the amino acid tyrosine. HT1 is the most severe form of this disorder and is caused by a shortage of the enzyme fumarylacetoacetate hydrolase (FAH) encoded by the gene Fah found on human chromosome number 15. FAH is the last in a series of five enzymes needed to break down tyrosine. Symptoms of HT1 usually appear in the first few months of life and include failure to gain weight and grow at the expected rate (failure to thrive), diarrhea, vomiting, yellowing of the skin and whites of the eyes (jaundice), cabbage-like odor, and increased tendency to bleed (particularly nosebleeds). HT1 can lead to liver and kidney failure, problems affecting the nervous system, and an increased risk of liver cancer.

Heterozygous: Having dissimilar alleles at corresponding chromosomal loci. For example, an animal heterozygous for a particular gene mutation has the mutation in one allele of the gene but not the other.

Homozygous: Having identical alleles at one or more loci. As used herein, "homozygous for disruptions" refers to an organism having disruptions (such as a deletion, insertion of point mutation) of both alleles of a gene.

Immunodeficient: Lacking in at least one essential function of the immune system. As used herein, an "immunodeficient" animal is one lacking specific components of the immune system or lacking function of specific components of the immune system (such as, for example, B cells, T cells or NK cells). In some cases, an immunodeficient animal lacks macrophages. In some embodiments, an immunodeficient animal (such as a Fah-deficient pig) comprises one or more genetic alterations that prevent or inhibit the development of functional immune cells (such as B cells, T cells or NK cells). In some examples, the genetic alteration is in the Rag1, Rag2 or Il2rg gene. Thus, in some cases, the immunodeficient animal is Rag1$^{-/-}$, Rag2$^{-/-}$ or Il2rg$^{-/-}$.

Immunosuppressant: Any compound that decreases the function or activity of one or more aspects of the immune system, such as a component of the humoral or cellular immune system or the complement system. Immunosuppressants are also referred to as "immunosuppressive agents." In particular embodiments of the disclosure, the immunosuppressant is FK506, cyclosporin A, fludarabine, mycophenolate, prednisone, rapamycin or azathioprine, or combinations thereof.

Known immunosuppressants include, but are not limited to: (1) antimetabolites, such as purine synthesis inhibitors (e.g., azathioprine and mycophenolic acid), pyrimidine synthesis inhibitors (e.g., leflunomide and teriflunomide) and antifolates (e.g., methotrexate); (2) macrolides, such as FK506, cyclosporine A and pimecrolimus; (3) TNF-α inhibitors, such as thalidomide and lenalidomide; (4) IL-1 receptor antagonists, such as anakinra; (5) mammalian target of rapamycin (mTOR) inhibitors, such as rapamycin (sirolimus), deforolimus, everolimus, temsirolimus, zotarolimus and biolimus A9; (6) corticosteroids, such as prednisone; and (7) antibodies to any one of a number of cellular or serum targets.

Exemplary cellular targets and their respective inhibitor compounds include, but are not limited to complement component 5 (e.g., eculizumab); tumor necrosis factors (TNFs) (e.g., infliximab, adalimumab, certolizumab pegol, afelimomab and golimumab); IL-5 (e.g., mepolizumab); IgE (e.g., omalizumab); BAYX (e.g., nerelimomab); interferon (e.g., faralimomab); IL-6 (e.g., elsilimomab); IL-12 and IL-13 (e.g., lebrikizumab and ustekinumab); CD3 (e.g., muromonab-CD3, otelixizumab, teplizumab, visilizumab); CD4 (e.g., clenoliximab, keliximab and zanolimumab); CD11a (e.g., efalizumab); CD18 (e.g., erlizumab); CD20 (e.g., afutuzumab, ocrelizumab, pascolizumab); CD23 (e.g., lumiliximab); CD40 (e.g., teneliximab, toralizumab); CD62L/L-selectin (e.g., aselizumab); CD80 (e.g., galiximab); CD147/basigin (e.g., gavilimomab); CD154 (e.g., ruplizumab); BLyS (e.g., Belimumab); CTLA-4 (e.g., ipilimumab, tremelimumab); CAT (e.g., bertilimumab, lerdelimumab, metelimumab); integrin (e.g., natalizumab); IL-6 receptor (e.g., Tocilizumab); LFA-1 (e.g., odulimomab); and IL-2 receptor/CD25 (e.g., basiliximab, daclizumab, inolimomab).

Other immunosuppressive agents include zolimomab aritox, atorolimumab, cedelizumab, dorlixizumab, fontolizumab, gantenerumab, gomiliximab, maslimomab, morolimumab, pexelizumab, reslizumab, rovelizumab, siplizumab, talizumab, telimomab aritox, vapaliximab, vepalimomab, anti-thymocyte globulin, anti-lymphocyte globulin; CTLA-4 inhibitors (e.g., abatacept, belatacept); aflibercept; alefacept; rilonacept; and TNF inhibitors (e.g., etanercept).

Immunosuppression: Refers to the act of reducing the activity or function of the immune system. Immunosuppression can be achieved by administration of an immunosuppressant compound or can be the effect of a disease or disorder (for example, immunosuppression that results from HIV infection or due to a genetic defect). In some cases, immunosuppression occurs as the result of a genetic mutation that prevents or inhibits the development of functional immune cells.

Induced pluripotency stem cells (IPSC): A type of pluripotent stem cell artificially derived from a non-pluripotent cell, typically an adult somatic cell, by inducing expression of certain genes. IPSCs can be derived from any organism, such as a mammal. In some embodiments, IPSCs are produced from mice, rats, rabbits, guinea pigs, goats, pigs, cows, non-human primates or humans. Human derived IPSCs are exemplary.

IPSCs are similar to ES cells in many respects, such as the expression of certain stem cell genes and proteins, chromatin methylation patterns, doubling time, embryoid body formation, teratoma formation, viable chimera formation, and potency and differentiability. Methods for producing IPSCs are known in the art. For example, IPSCs are typically derived by transfection of certain stem cell-associated genes (such as Oct-3/4 (Pouf51) and Sox2) into non-pluripotent cells, such as adult fibroblasts. Transfection can be achieved through viral vectors, such as retroviruses, lentiviruses, or adenoviruses. For example, cells can be transfected with Oct3/4, Sox2, Klf4, and c-Myc using a retroviral system or with OCT4, SOX2, NANOG, and LIN28 using a lentiviral system. After 3-4 weeks, small numbers of transfected cells begin to become morphologically and biochemically similar to pluripotent stem cells, and are typically isolated through morphological selection, doubling time, or through a reporter gene and antibiotic selection. In one example, IPSCs from adult human cells are generated by the method of Yu et al. (*Science* 318(5854):1224, 2007) or Takahashi et al. (*Cell* 131(5):861-72, 2007). IPSCs are also known as iPS cells.

Infectious load: Refers to the quantity of a particular pathogen in a subject or in a sample from the subject. Infectious load can be measured using any one of a number of methods known in the art. The selected method will vary depending on the type of pathogen to be detected and the reagents available to detect the pathogen. Infectious load can also be measured, for example, by determining the titer of the pathogen, the method for which will vary depending on the pathogen to be detected. For example, the titer of some viruses can be quantified by performing a plaque assay. In some examples, infectious load is measured by quantifying the amount of a pathogen-specific antigen in a sample. In other examples, infectious load is measured by quantifying the amount of a pathogen-specific nucleic acid molecule in a sample. Quantifying encompasses determining a numerical value or can be a relative value.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extrachromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

An "isolated hepatocyte" refers to a hepatocyte that has been obtained from a particular source, such as an organ donor. In some embodiments, an "isolated hepatocyte" is a hepatocyte that has been removed from the body of a donor. In some embodiments, "isolated hepatocytes" are hepatocytes in suspension or hepatocytes contained within a piece of tissue. In particular examples, isolated hepatocytes are those that are substantially separated or purified away from other cell types, or purified away from other types of tissue, such as adipose tissue or fibrotic tissue.

Mammalian target of rapamycin (mTOR) inhibitor: A molecule that inhibits expression or activity of mTOR. mTOR inhibitors include, but are not limited to small molecule, antibody, peptide and nucleic acid inhibitors. For example, an mTOR inhibitor can be a molecule that inhibits the kinase activity of mTOR or inhibits binding of mTOR to a ligand. Inhibitors of mTOR also include molecules that down-regulate expression of mTOR. A number of mTOR inhibitors are known in the art, including rapamycin (sirolimus).

Mycophenolate: An immunosuppressant typically used to prevent rejection of allogeneic transplants. This drug is generally administered orally or intravenously. Mycophenolate is derived from the fungus *Penicillium stoloniferum*. Mycophenolate mofetil, the pro-drug form, is metabolized in the liver to the active moiety mycophenolic acid. It inhibits inosine monophosphate dehydrogenase, the enzyme that controls the rate of synthesis of guanine monophosphate in the de novo pathway of purine synthesis used in the proliferation of B and T lymphocytes. Mycophenolic acid is commonly marketed under the trade names CellCept™ (mycophenolate mofetil; Roche) and Myfortic™ (mycophenolate sodium; Novartis).

NTBC (2-nitro-4-trifluoro-methyl-benzoyl)-1,3 cyclohexanedione): An inhibitor of 4-hydroxy-phenylpyruvate dioxygenase (HPPD). HPPD catalyzes the conversion of 4-hydroxyphenylpyruvate to homogentisate, the second step in tyrosine catabolism. Treatment with NTBC blocks the tyrosine catabolism pathway at this step and prevents the accumulation of succinylacetone, a pathognomonic metabolite that accumulates in Fah-deficient humans and animals.

Prednisone: A synthetic corticosteroid that is an effective immunosuppressant. It is often used to treat certain inflammatory diseases, autoimmune diseases and cancers as well as treat or prevent organ transplant rejection. Prednisone is usually taken orally but can be delivered by intramuscular injection or intravenous injection. It is a prodrug that is converted by the liver into prednisolone, which is the active drug and also a steroid.

Rapamycin: A compound with known immunosuppressive and anti-proliferative properties. Rapamycin, also known as sirolimus, is a macrolide that was first discovered as a product of the bacterium Streptomyces hygroscopicus. Rapamycin binds and inhibits the activity of mTOR.

Recipient: As used herein, a "recipient animal" is an animal (such as a pig) that has been injected with the isolated human hepatocytes described herein. Typically, a portion (the percentage can vary) of the human hepatocytes engraft in the recipient animal. In some embodiments, the recipient animal is immunosuppressed.

Recombinase activating gene 1 (Rag1): A gene involved in activation of immunoglobulin V(D)J recombination. The RAG1 protein is involved in recognition of the DNA substrate, but stable binding and cleavage activity also requires RAG2.

Recombinase activating gene 2 (Rag2): A gene involved in recombination of immunoglobulin and T cell receptor loci. Animals deficient in the Rag2 gene are unable to undergo V(D)J recombination, resulting in a complete loss of functional T cells and B cells (Shinkai et al. *Cell* 68:855-867, 1992).

Serial transplantation: The process for expanding human hepatocytes in vivo in which hepatocytes expanded in a first animal are collected and transplanted, such as by injection, into a secondary animal for further expansion. Serial transplantation can further include tertiary, quaternary or additional animals (Overturf et al., *Am. J. Pathol.* 151: 1078-9107, 1997).

Somatic cell nuclear transfer (SCNT): A laboratory technique for creating a clonal embryo, using an ovum with a donor nucleus. In SCNT, the nucleus of a somatic cell is removed and the rest of the cell discarded. At the same time, the nucleus of an egg cell is removed. The nucleus of the somatic cell is then inserted into the enucleated egg cell. After being inserted into the egg, the somatic cell nucleus is reprogrammed by the host cell. The egg, now containing the nucleus of a somatic cell, is stimulated with a shock and will begin to divide. After many mitotic divisions in culture, this single cell forms a blastocyst with almost identical DNA to the original organism.

Sow: An adult female pig.

Stem cell: A cell having the unique capacity to produce unaltered daughter cells (self-renewal; cell division produces at least one daughter cell that is identical to the parent cell) and to give rise to specialized cell types (potency). Stem cells include, but are not limited to, embryonic stem (ES) cells, embryonic germ (EG) cells, germline stem (GS) cells, human mesenchymal stem cells (hMSCs), adipose tissue-derived stem cells (ADSCs), multipotent adult progenitor cells (MAPCs), multipotent adult germline stem cells (maGSCs) and unrestricted somatic stem cell (USSCs). The role of stem cells in vivo is to replace cells that are destroyed during the normal life of an animal. Generally, stem cells can divide without limit. After division, the stem cell may remain as a stem cell, become a precursor cell, or proceed to terminal differentiation. A precursor cell is a cell that can generate a fully differentiated functional cell of at least one given cell type. Generally, precursor cells can divide. After division, a precursor cell can remain a precursor cell, or may proceed to terminal differentiation. In one embodiment, the stem cells give rise to hepatocytes.

Subject: Living multi-cellular vertebrate organisms, a category that includes both human and non-human mammals, including pigs.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject. As used herein, a "candidate agent" is a compound selected for screening to determine if it can function as a therapeutic agent for a particular disease or disorder.

Titer: In the context of the present disclosure, titer refers to the amount of a particular pathogen in a sample.

Tolerance: A state of unresponsiveness to a specific antigen or group of antigens to which a subject (such as a human or animal) is normally responsive. Immune tolerance is achieved under conditions that suppress the immune reaction and is not just the absence of an immune response. Immune tolerance can result from a number of causes including prior contact with the same antigen in fetal life or in the newborn period when the immune system is not yet mature; prior contact with the antigen in extremely high or low doses; exposure to radiation, chemotherapy drugs, or other agents that impair the immune system; heritable diseases of the immune system; and acquired diseases of the immune system.

Toxin: In the context of the present disclosure, "toxin" refers to any poisonous substance, including any chemical toxin or biological toxin.

Transgene: An exogenous nucleic acid sequence introduced into a cell or the genome of an organism.

Transgenic animal: A non-human animal, usually a mammal, having a non-endogenous (heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal according to methods well known in the art. A "transgene" is meant to refer to such heterologous nucleic acid, such as, heterologous nucleic acid in the form of an expression construct (such as for the production of a "knock-in" transgenic animal) or a heterologous nucleic acid that upon insertion within or adjacent to a target gene results in a decrease in target gene expression (such as for production of a "knock-out" transgenic animal). A "knock-out" of a gene means an alteration in the sequence of the gene that results in a decrease of function of the target gene, preferably such that target gene expression is undetectable or insignificant. Transgenic knock-out animals can comprise a heterozygous knock-out of a target gene, or a homozygous knock-out of a target gene. "Knock-outs" also include conditional knock-outs, where alteration of the target gene can occur upon, for example, exposure of the animal to a substance that promotes target gene alteration, introduction of an enzyme that promotes recombination at the target gene site (for example, Cre in the Cre-lox system), or other method for directing the target gene alteration postnatally.

Transplant or transplanting: Refers to the process of grafting an organ, tissue or cells from one subject to another subject, or to another region of the same subject.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An integrating vector is capable of integrating itself into a host nucleic acid. An expression vector is a vector that contains the necessary regulatory sequences to allow transcription and translation of inserted gene or genes.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

In humans, hereditary tyrosinemia type I (HT1) is a severe, autosomal recessive inborn error of metabolism caused by deficiency of fumarylacetoacetate hydrolase (FAH), a metabolic enzyme that catalyzes the last step of tyrosine metabolism (Lindblad et al., *Proc Natl Acad Sci USA* 74:4641-4645, 1977). Affected children develop micronodular cirrhosis and 36% develop HCC by age five if untreated (Russo and O'Regan, *Am J Hum Genet* 47:317-324, 1990). A small animal model of HT1 was previously developed by generating Fah mutant mice by gene targeting in embryonic stem cells (Grompe et al., *Genes Dev* 7:2298-2307, 1993). The phenotype of these mice is analogous to many of the key features of the human disorder, including the formation of liver cancer, and has proven to be an important research model for both HT1 and HCC (Al-Dhalimy et al., *Mol Genet Metab* 75:38-45, 2002; Grompe et al., *Nat Genet.* 10:453-460, 1995; Sun et al., *J Am Soc Nephrol* 11:291-300, 2000; Willenbring et al., *Cancer Cell* 14:59-67, 2008). However, this mouse model fails to recapitulate all of the aspects of the human disorder, most importantly cirrhosis.

Current methodologies to induce cirrhosis and HCC in animals often utilize harsh chemicals, radioactively labeled substances or the over-expression of viral genes (Gold et al., *Environ Health Perspect* 93:233-246, 1991; Hahn et al., *Toxicol Pathol* 24:281-289, 1996; Kim et al., *Nature* 351:317-320, 1991; Koike et al., *Hepatology* 19:810-819, 1994; Yan et al., *J Cancer Res Clin Oncol* 122:283-288, 1996). Using these methods HCC has been created in a number of animals, including pigs (Graw and Berg, *Cancer Res Clin Oncol* 89:137-143, 1977). However, these approaches fail to reproduce all of the relevant cellular and molecular events associated with HCC along with the typical tumor-host interaction seen between primary and metastatic HCC in humans (Aravalli et al., *Eur Radiol* 19:1049-1053, 2009). Currently, the porcine model of nitrosodiethylamine induced cirrhosis and HCC is the preferred large animal model for testing new liver directed therapies (Li et al., *Cardiovasc Intervent Radiol* 29:420-428, 2006). In addition to the incomplete formation of tumors in all animals, one of the primary limitations of this model is the long time (12-18 months) needed to induce HCC.

Similar deficits in small animal models of other human disease have been reported as well. In cystic fibrosis (CF), multiple mice and rabbit models were engineered to contain several of the common genetic mutations seen in humans. However, these models failed to fully reproduce the disease phenotype observed in humans (Li et al., *Cardiovasc Intervent Radiol* 29:420-428, 2006; Guilbault et al., *Am J Respir Cell Mol Biol* 36:1-7, 2007). The pig is an appropriate research model because of its similarity in size, anatomy and biology to the human (Cooper et al., *Annu Rev Med* 53:133-147, 2002). This led researchers to create a porcine model of CF by using adeno-associated virus (AAV)-mediated gene targeting in combination with SCNT to create their pig model of CF, which has now been shown to display the characteristic manifestations of CF seen in humans (Rogers et al., *J Clin Invest* 118:1571-1577, 2008; Rogers et al., *Science* 321:1837-1841, 2008).

The CF pig was the first time AAV had been used to generate a porcine gene-knockout model. Up to this point, the generation of large animal models of disease had been hindered by the inability to apply mouse embryonic stem cell targeting approaches to non-murine models. AAV-mediated gene targeting and SCNT provide an alternative method to generate gene-knockout animals. AAV vectors have been shown to be able to introduce specific mutations, including insertions, into homologous chromosomal sequences of many cell types and species (Russell and, Hirata, *Nat Genet.* 18:325-330, 1998; Paulk et al., *Hepatology* 51:1200-1208, 2010). In addition, AAV-mediated gene targeting has been shown to be more efficient than conventional techniques based on transfection or electroporation of plasmid constructs (Brown et al., *Science* 277:831-834, 1997; Yanez and Porter, *Gene Ther* 5:149-159, 1998). However, the highest published targeting efficiency of AAV in various systems remains close to 1% (Russell et al., *Nat Biotechnol* 20:658, 2002).

Disclosed herein is the development of a more efficient method to create pig knock-out models of human diseases and the production of Fah-null heterozygote pigs to be used to generate homozygote Fah-null animals for studies related to metabolic liver disease, cirrhosis, HCC and gene therapy. As described in the Examples below, the novel chimeric AAV-DJ serotype was used to disrupt the porcine Fah gene by targeted gene knockout by homologous recombination. Disclosed herein is the successful and efficient generation of targeted Fah-null heterozygote fibroblasts and their use by SCNT to generate Fah-null heterozygote pigs.

IV. Overview of Several Embodiments

Disclosed herein is the generation of $Fah^{+/-}$ heterozygote pigs by homologous recombination in fetal pig fibroblasts, followed by somatic cell nuclear transfer. Also disclosed is a method for producing Fah$^{-/-}$ homozygote pigs. The Fah-deficient pigs of the disclosure can be used for a variety of research and therapeutic purposes, such as for the expansion of hepatocytes from other species (such as humans), and as large animal models of liver disease, including hereditary tyrosinemia type 1 (HT1), cirrhosis, hepatocellular carcinoma and liver infection. Although a Fah-deficient mouse model has been previously described (Grompe et al. *Genes Dev.* 7:2298-2307, 1993; PCT Publication Nos. WO 2008/151283 and WO 2010/127275), the Fah-deficient pig offers significant advantages, particularly for the expansion of human hepatocytes as the number of hepatocytes that can be expanded in mice is limited due to their small size. Moreover, Fah-deficient mice fail to recapitulate all of the key features of the human disease HT1, which results from a deficiency in the FAH enzyme. The Fah-deficient pig disclosed herein provides a large animal model of human HT1 disease and represents the first large animal model of HCC arising spontaneously in the background of cirrhosis.

Described herein are two methods for expanding hepatocytes in Fah-deficient pigs. Although the expansion of human hepatocytes is exemplified, the methods disclosed herein can be used to expand hepatocytes from other species, for example mice, rats, dogs, cats, cows, horses and non-human primates, such as baboons, chimpanzees and rhesus macaques. The first method disclosed herein involves postnatal transplantation of human hepatocytes into Fah-deficient piglets or adult pigs, such as piglets or pigs made by the method disclosed herein. Post-natal transplantation is accompanied by treatment with one or more immunosuppressive agents to prevent rejection of the human cells. The second method involves fetal transplantation of human hepatocytes. In this method, pig fetuses are surgically externalized and injected with human hepatocytes. Tolerance to the human hepatocytes will develop, eliminating the need to administer immunosuppressive drugs to the Fah-deficient pigs transplanted with human hepatocytes.

Although the use of immunosuppressive drugs is exemplified as a means of created immunodeficient animals, also contemplated are genetic alterations that result in a lack of a specific component of the immune system, or a lack of functionality of a specific component of the immune system (such as a lack of functional B, T and/or NK cells). In some embodiments, the genetic alteration is in the Rag1, Rag2 or Il2rg gene. Specific cells of the immune system (such as macrophages or NK cells) can also be depleted. Methods of depleting particular cell types are known in the art.

Moreover, the two disclosed methods of expanding human hepatocytes in Fah-deficient pigs can be combined. Fetal transplantation can be carried out to induce tolerance to the human hepatocytes, thus permitting the administration of a larger dose of human hepatocytes postnatally.

Thus, provided herein is a method of expanding human hepatocytes in vivo by transplanting human hepatocytes into a Fah-deficient pig and allowing the human hepatocytes to expand. The length of time for hepatocyte expansion can vary and will depend on a variety of factors, including the number of hepatocytes originally transplanted, the number of human hepatocytes desired following expansion and/or the desired degree of liver repopulation with the human hepatocytes. In some cases, these factors will be dictated by the desired use of the hepatocytes or the desired use of the Fah-deficient pig engrafted with the human hepatocytes. In some embodiments, the human hepatocytes are expanded in the Fah-deficient pig for at least about 3 days, at least about 5 days, at least about 7 days, at least about 2 weeks, or at least about 4 weeks, at least about 2 months, at least about 3 months, at least about 4 months, at least about 5 months, at least about 6 months, at least about 7 months, at least about 8 months, at least about 9 months, at least about 10 months or at least about 11 months. In particular examples, the human hepatocytes are expanded in the Fah-deficient pig for at least 7 days. In other examples, the human hepatocytes are expanded in the Fah-deficient pig for at least 6 months. In some examples, the human hepatocytes are expanded in the Fah-deficient pig no more than 12 months.

In some embodiments, the Fah-deficient pig is administered an agent that inhibits, delays or prevents the development of liver disease in the pig. Administration of such an agent is necessary to prevent liver dysfunction and/or death of the animal prior to repopulation of the animal with healthy (FAH-expressing) hepatocytes. The agent can be any compound or composition known in the art to inhibit liver disease. One such agent is 2-(2-nitro-4-trifluoro-methyl-benzoyl)-1,3 cyclohexanedione (NTBC), but other pharmacologic inhibitors of phenylpyruvate dioxygenase, such as methyl-NTBC can be used. NTBC (or a similar compound) is administered to regulate the development of liver disease in the Fah-deficient pig. The dose, dosing schedule and method of administration can be adjusted as needed to prevent liver dysfunction in the Fah-deficient pig. In some embodiments, the Fah-deficient pig is further administered NTBC for at least two days, at least three days, at least four days, at least five days or at least six days following hepatocyte transplantation. In some embodiments, the Fah-deficient pig is further administered NTBC for at least about one week, at least about two weeks, at least about three weeks, at least about four weeks, at least about one month, at least about two months, at least about three months, at least about four months, at least about five months, or at least about six months.

The dose of NTBC administered to the Fah-deficient pig can vary. In some embodiments, the dose is about 0.2 mg/kg to about 2.0 mg/kg per day. In particular examples, the dose of NTBC is about 1 mg/kg per day. In other embodiments, NTBC is administered at a dose of about 0.01 mg/kg/day to about 0.50 mg/kg/day. In another embodiment, the NTBC is administered at a dose of about 0.05 mg/kg/day to about 0.10 mg/kg/day, such as about 0.05 mg/kg/day, about 0.06 mg/kg/day, about 0.07 mg/kg/day, about 0.08 mg/kg/day, about 0.09 mg/kg/day or about 0.10 mg/kg/day.

In other embodiments, the pig is administered a candidate agent that is being tested for hepatoprotective or hepatotherapeutic properties. A method similar to that discussed above for NTBC can be used to assess the protective effect of the agent.

NTBC can be administered by any suitable means, such as, but limited to, in the drinking water, in the food or by injection. In one embodiment, the concentration of NTBC administered in the drinking water is about 1 to about 8 mg/L, such as about 1 mg/L, about 2 mg/L, about 3 mg/L, about 4 mg/L, about 5 mg/L, about 6 mg/L, about 7 mg/L or about 8 mg/L. In another embodiment, the concentration of NTBC administered in the drinking water is about 1 to about 2 mg/L, such as about 1.0 mg/L, about 1.2 mg/L, about 1.4 mg/L, about 1.6 mg/L, about 1.8 mg/L or about 2.0 mg/L.

In some embodiments of the method, the Fah-deficient pig is immunosuppressed. In some examples, immunosuppression is the result of administration of one or more immunosuppressive agents. Any suitable immunosuppressive agent or agents effective for achieving immunosuppression in a pig can be used. Examples of immunosuppressive agents include, but are not limited to, FK506, cyclosporin A, fludarabine, mycophenolate, prednisone, rapamycin and azathioprine. Combinations of immunosuppressive agents can also be administered. In some embodiments, the one or more immunosuppressive agents are administered to the Fah-deficient pig at least about 2 days prior to human hepatocyte transplantation. Immunosuppression may be continued for a period of time, for example for a portion of or the entire life of the pig.

In some embodiments, the human hepatocytes are transplanted by injection into the hepatic artery, spleen or portal vein of the Fah-deficient pig.

In some embodiments, the Fah-deficient pig comprises homozygous disruptions in the Fah gene such that the disruption results in loss of expression of functional FAH protein. The loss of expression of functional FAH protein need not be complete loss of expression. In some examples, loss of expression of functional FAH protein is loss of expression of about 80%, about 90%, about 95% or about 99%.

The Fah gene disruption can be any modification that results in a significant diminishment or complete loss of expression of functional FAH protein. In some embodiments, the disruption is an insertion, a deletion or one or more point mutations in the Fah gene, or any combination thereof. In particular examples, the disruption is an insertion. In some examples, the insertion includes an in-frame stop codon. The insertion can also include additional nucleic acid sequences, such as nucleic acid encoding a selectable marker.

In some embodiments, the human hepatocytes transplanted into the Fah-deficient pig are isolated human hepatocytes. In some embodiments, the human hepatocytes are transplanted as part of a liver tissue graft. The isolated human hepatocytes can be obtained from any one of a number of different sources. In one embodiment, the human hepatocytes are isolated from the liver of an organ donor. In another embodiment, the human hepatocytes are isolated from a surgical resection. In another embodiment, the human hepatocytes are derived from a stem cell, such as an embryonic stem cell, an induced pluripotency stem cell, a mesenchymal-derived stem cell, an adipose tissue-derived stem cell, a multipotent adult progenitor cell, an unrestricted somatic stem cell or tissue-specific liver stem cell, which can be found in the liver itself, the gall bladder, the intestine or pancreas. In another embodiment, the human hepatocytes are derived from monocytes or amniocytes, thus a stem cell or progenitor cell is obtained in vitro to produce hepatocytes. In another embodiment, the human hepatocytes are cryopreserved prior to injection.

In some embodiments, the method further includes collecting the expanded human hepatocytes from the Fah-deficient pig.

Also provided herein is a method of expanding human hepatocytes in vivo by transplanting human hepatocytes into a Fah-deficient pig fetus and allowing the human hepatocytes to expand following birth of the Fah-deficient pig. The length of time for hepatocyte expansion after birth can vary and will depend on a variety of factors, including the number of hepatocytes originally transplanted, the number of human hepatocytes desired following expansion and/or the desired degree of liver repopulation with the human hepatocytes. In some cases, these factors will be dictated by the desired use of the hepatocytes or the desired use of the Fah-deficient pig engrafted with the human hepatocytes. In some embodiments, the human hepatocytes are expanded in the Fah-deficient pig for at least about 3 days, at least about 5 days, at least about 7 days, at least about 2 weeks, or at least about 4 weeks, at least about 2 months, at least about 3 months, at least about 4 months, at least about 5 months, at least about 6 months, at least about 7 months, at least about 8 months, at least about 9 months, at least about 10 months, or at least about 11 months. In particular examples, the human hepatocytes are expanded in the Fah-deficient pig for at least 7 days. In other examples, the human hepatocytes are expanded in the Fah-deficient pig for at least 6 months. In some examples, the human hepatocytes are expanded in the Fah-deficient pig no more than 12 months.

In some embodiments, the Fah-deficient pig fetus is surgically externalized to transplant the human hepatocytes. The gestational age of the pig fetus at which the human hepatocytes are injected can vary, but is generally before the thymus has developed. Thus, in some embodiments, human hepatocytes are injected into the pig fetus between about day 30 and about day 45, such as between days 35-45, of gestation of the pig. In particular examples, the human hepatocytes are transplanted at day 35 of gestation of the pig. In other particular examples, the human hepatocytes are transplanted at day 40 of gestation of the pig. In some embodiments, the human hepatocytes are transplanted by injection into the umbilical vein of the Fah-deficient pig fetus, or directly into the fetal liver. The number of human hepatocytes injected can vary. In some embodiments, the pig fetus is injected with 100,000 to $1\times10^8$, such as 500,000 to $1\times10^7$, human hepatocytes. In some examples, the pig fetus is injected with about $1\times10^6$ to about $1\times10^8$, such as about $1\times10^7$, human hepatocytes. In one non-limiting example, the pig fetus is injected with approximately $1\times10^7$ human hepatocytes directly into the fetal liver. In other examples, the number of human hepatocytes injected is about 100,000 to about 500,000, such as about 300,000.

In some embodiments, the sow pregnant with the Fah-deficient pig fetus is administered an agent that inhibits, delays or prevents the development of liver disease in the pig. The agent can be any compound or composition known in the art to inhibit liver disease, such as a pharmacologic inhibitor of phenylpyruvate dioxygenase, for example NTBC or methyl-NTBC. In some embodiments, the Fah-deficient piglet is also administered NTBC (or a similar compound) for about 1 to about 6 days after birth. In some embodiments, the Fah-deficient piglet is also administered NTBC for at least one month, at least two months, at least three months, at least four months, at least five months or at least six months. In some embodiments, the Fah-deficient piglet is also administered NTBC indefinitely.

The dose, dosing schedule and method of administration can be adjusted as needed to prevent liver dysfunction in the Fah-deficient pig. The dose of NTBC administered to the Fah-deficient pig can vary. In some embodiments, the dose is about 0.2 mg/kg to about 2.0 mg/kg per day. In particular examples, the dose of NTBC is about 1 mg/kg per day. In other embodiments, NTBC is administered at a dose of about 0.01 mg/kg/day to about 0.50 mg/kg/day. In another embodiment, the NTBC is administered at a dose of about 0.05 mg/kg/day to about 0.10 mg/kg/day, such as about 0.05 mg/kg/day, about 0.06 mg/kg/day, about 0.07 mg/kg/day, about 0.08 mg/kg/day, about 0.09 mg/kg/day or about 0.10 mg/kg/day.

NTBC (or a similar compound) can be administered by any suitable means, such as, but limited to, in the drinking water, in the food or by injection. In one embodiment, the concentration of NTBC administered in the drinking water is about 1 to about 8 mg/L, such as about 1 mg/L, about 2 mg/L, about 3 mg/L, about 4 mg/L, about 5 mg/L, about 6 mg/L, about 7 mg/L or about 8 mg/L. In another embodiment, the concentration of NTBC administered in the drinking water is about 1 to about 2 mg/L, such as about 1.0 mg/L, about 1.2 mg/L, about 1.4 mg/L, about 1.6 mg/L, about 1.8 mg/L or about 2.0 mg/L.

In some embodiments, the human hepatocytes transplanted into the Fah-deficient pig fetus are isolated human hepatocytes. In some embodiments, the human hepatocytes are transplanted as part of a liver tissue graft. The isolated human hepatocytes can be obtained from any one of a number of different sources. In one embodiment, the human hepatocytes are isolated from the liver of an organ donor. In another embodiment, the human hepatocytes are isolated from a surgical resection. In another embodiment, the human hepatocytes are derived from a stem cell, such as an embryonic stem cell, an induced pluripotency stem cell, a mesenchymal-derived stem cell, an adipose tissue-derived stem cell, a multipotent adult progenitor cell, an unrestricted somatic stem cell or tissue-specific liver stem cell, which can be found in the liver itself, the gall bladder, the intestine or pancreas. In another embodiment, the human hepatocytes are derived from monocytes or amniocytes, thus a stem cell or progenitor cell is obtained in vitro to produce hepatocytes. In another embodiment, the human hepatocytes are cryopreserved prior to injection.

In some embodiments, the method further includes collecting the expanded human hepatocytes from the Fah-deficient pig.

Further provided herein is a method of serial transplantation of human hepatocytes (or hepatocytes from another species) in the Fah-deficient recipient pig. The method comprises collecting the expanded human hepatocytes from a first recipient pig and further expanding the hepatocytes in a second, third, fourth or additional recipient pig. Human hepatocytes can be collected from a pig using any one of a number of techniques. For example, the hepatocytes can be collected by perfusing the pig liver, followed by gentle mincing. Furthermore, the hepatocytes can be separated from other cell types, tissue and/or debris using well known methods, such as by using an antibody that specifically recognizes human cells, or human hepatocytes. Such antibodies include, but are not limited to an antibody that specifically binds to a class I major histocompatibility antigen, such as anti-human HLA-A,B,C (Markus et al. *Cell Transplantation* 6:455-462, 1997). Antibody bound hepatocytes can then be separated by panning (which utilizes a monoclonal antibody attached to a solid matrix), fluorescence activated cell sorting (FACS), magnetic bead separation or the like. Alternative methods of collecting hepatocytes are well known in the art. Methods of serially transplanting hepatocytes in an animal are described, for example, in PCT Publication No. 2008/151283.

Further provided herein is a genetically modified pig whose genome is homozygous for a disruption in the Fah gene such that the disruption results in loss of expression of functional FAH protein, wherein the pig exhibits decreased liver function. The loss of expression of functional FAH protein need not be complete loss of expression. In some examples, loss of expression of functional FAH protein is loss of expression of about 80%, about 90%, about 95% or about 99%. The Fah gene disruption can be any modification that results in a significant diminishment or complete loss of expression of functional FAH protein. In some embodiments, the disruption is an insertion, a deletion or one or more point mutations in the Fah gene, or any combination thereof. In particular examples, the disruption is an insertion. In some examples, the insertion includes an in-frame stop codon. The insertion can also include additional nucleic acid sequences, such as nucleic acid encoding a selectable marker.

In some embodiments, the Fah-deficient pig comprises transplanted human hepatocytes. In some embodiments, the Fah-deficient pig is immunosuppressed. In some examples, immunosuppression is the result of administration of one or more immunosuppressive agents. Any suitable immunosuppressive agent or agents effective for achieving immunosuppression in a pig can be used. Examples of immunosuppressive agents include, but are not limited to, FK506, cyclosporin A, fludarabine, mycophenolate, prednisone, rapamycin and azathioprine. Combinations of immunosuppressive agents can also be administered. In some examples, immunosuppression is the result of one or more genetic alterations that inhibit the development of functional immune cells. Immunosuppression may also result from depletion of particular immune cells, such as macrophages or NK cells.

A method for selecting an agent effective for the treatment of a human liver disease is also provided. In some embodiments, the method includes administering a candidate agent to a Fah-deficient pig and assessing the effect of the candidate agent on the liver disease, wherein an improvement in one or more signs or symptoms of the liver disease, indicates the candidate agent is effective for the treatment of the liver disease. In some embodiments, the liver disease is hepatic infection, cirrhosis or HCC.

Also provided herein is a method for selecting an agent effective for the treatment of infection by a human hepatic pathogen. In some embodiments, the method includes (i) administering a candidate agent to a Fah-deficient pig transplanted with human hepatocytes, wherein the Fah-deficient pig is infected with the hepatic pathogen; and (ii) assessing the effect of the candidate agent on the hepatic infection. A decrease in infectious load of the hepatic pathogen relative to infectious load in the Fah-deficient pig prior to administration of the candidate agent, indicates the candidate agent is effective for the treatment of the infection by the hepatic pathogen.

In some embodiments, the infectious load is determined by measuring titer of the pathogen in a sample obtained from the pig. In some embodiments, the infectious load is determined by measuring a pathogen-specific antigen in a sample obtained from the pig. In some embodiments, the infectious load is determined by measuring a pathogen-specific nucleic acid molecule in a sample obtained from the pig. In some embodiments, the hepatic pathogen is a hepatotropic virus, such as HBV or HCV.

Further provided is a method for selecting an agent effective for the treatment of cirrhosis. In some embodiments, the method includes (i) administering a candidate agent to a Fah-deficient pig, wherein the Fah-deficient pig has been administered a pharmacologic inhibitor of phenylpyruvate dioxygenase, such as NTBC, at a dose that results in development of cirrhosis in the pig; and (ii) assessing the effect of the candidate agent on at least one diagnostic marker of cirrhosis in the Fah-deficient pig. In some embodiments, the at least one diagnostic marker of cirrhosis is selected from aspartate aminotransferase (AST), alanine aminotransferase (ALT), bilirubin, alkaline phosphatase, albumin, or clotting factors. A decrease in the at least one AST, ALT, bilirubin, or alkaline phosphatase, and/or an increase in albumin in the Fah-deficient pig relative to the Fah-deficient pig prior to administration of the candidate agent, indicates the candidate agent is effective for the treatment of cirrhosis. In some embodiments, once the Fah-deficient pig has developed cirrhosis, the animal receives a full dose of NTBC to prevent further progression of cirrhosis. Other diagnostic markers (such as by imaging or liver biopsy) to evaluate cirrhosis can also be used in the disclosed methods.

Also provided is a method for selecting an agent effective for the treatment of hepatocellular carcinoma (HCC). In some embodiments, the method includes (i) administering a candidate agent to a Fah-deficient pig, wherein the Fah-deficient pig has been administered a pharmacologic inhibitor of phenylpyruvate dioxygenase, such as NTBC or methyl-NTBC, at a dose that results in development of HCC in the pig; and (ii)

assessing the effect of the candidate agent on HCC in the Fah-deficient pig. A decrease in tumor growth or tumor volume in the Fah-deficient pig relative to the Fah-deficient pig prior to administration of the candidate agent, indicates the candidate agent is effective for the treatment of HCC.

Further provided is a method of assessing the effect of an exogenous agent on human hepatocytes in vivo. In some embodiments, the method includes administering the exogenous agent to a Fah-deficient pig transplanted with human hepatocytes and measuring at least one marker of liver function in the Fah-deficient pig. In some embodiments, the at least one marker of liver function is selected from AST, ALT, bilirubin, alkaline phosphatase and albumin, and wherein an increase in AST, ALT, bilirubin or alkaline phosphatase, or a decrease in albumin in the Fah-deficient pig relative to the Fah-deficient pig prior to administration of the exogenous agent, indicates the exogenous agent is toxic. In some embodiments, the exogenous agent is a known or suspected toxin.

Also provided is a genetically modified Fah-deficient pig whose genome is heterozygous for a disruption in the Fah gene. In some embodiments, the disruption is in exon 5 of the Fah gene. In particular examples, the disruption is an insertion, a deletion or one or more point mutations in the Fah gene. An insertion can include, for example, a stop codon, a selectable marker, or both.

Further provided is a method of making a genetically modified Fah-deficient pig whose genome is homozygous for a disruption in the Fah gene. The method includes breeding genetically modified Fah-deficient pig having a genome heterozygous for a disruption in the Fah gene; and selecting offspring that are homozygous for the disruption in the Fah gene.

V. Fah-Deficient Pigs and Uses Thereof

Figure 6:
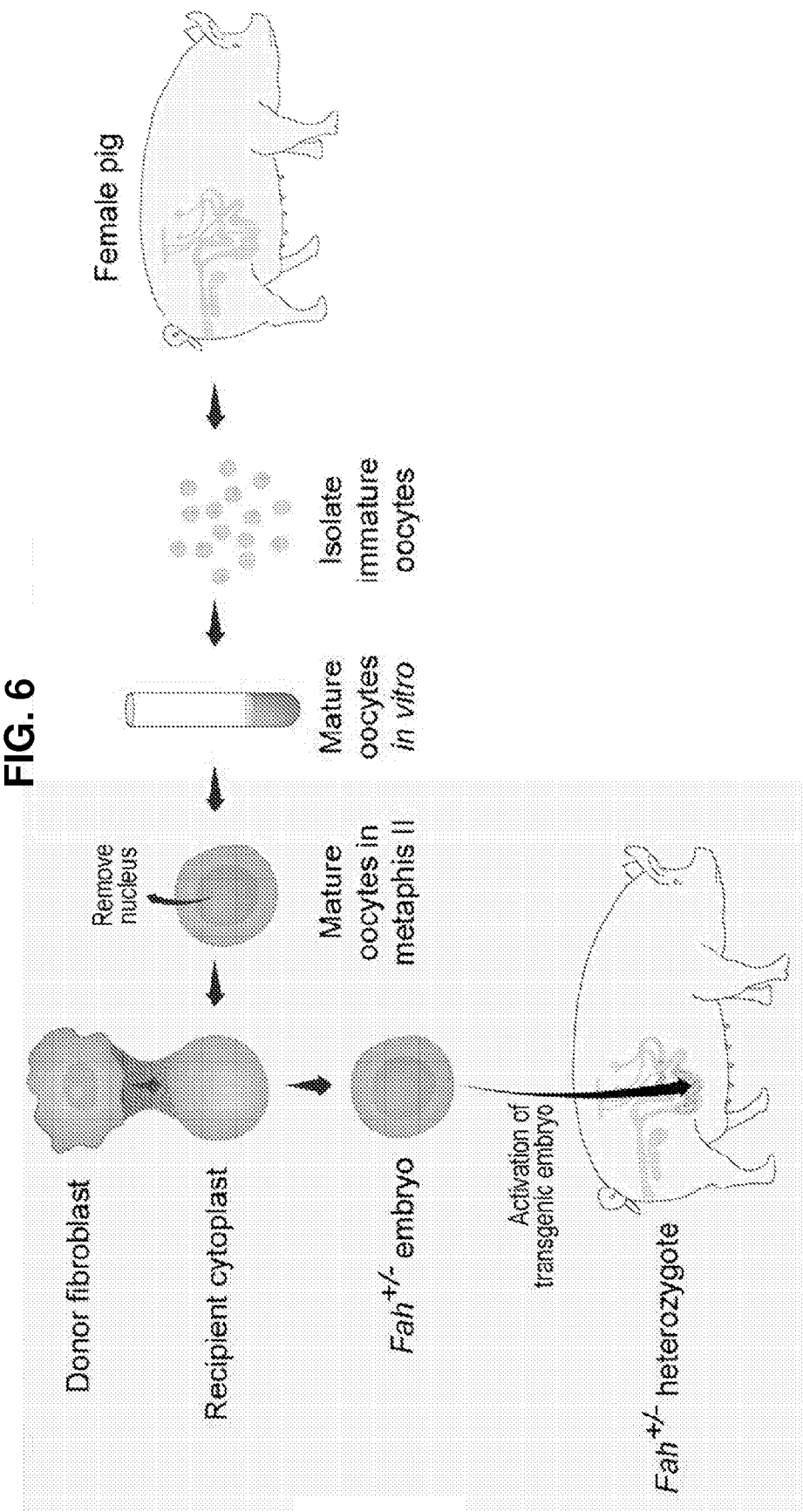
FIG. 6 is a schematic illustration of the somatic cell nuclear transfer (SCNT) technique.

Disclosed herein is the generation of Fah-deficient pigs by homologous recombination using an AAV targeting construct in pig fetal fibroblasts, followed by somatic cell nuclear transfer (SCNT). The procedure used to produce $Fah^{+/-}$ pigs from fetal fibroblasts by SCNT is illustrated in FIG. 6. An illustration of the methods to produce a $Fah^{-/-}$ pig is shown in FIG. 1. As discussed in greater detail below, Fah-deficient pigs are useful for a number of research and therapeutic purposes.

An exemplary method of generating $Fah^{+/-}$ pigs is described in Example 1 and a procedure to produce homozygote Fah-deficient pigs by cross-breeding $Fah^{+/-}$ pigs is described in Example 4. However, this disclosure is not limited to one particular method of generating a Fah-deficient pig, but encompasses any method known in the art to produce a $Fah^{-/-}$ pig.

As disclosed herein, $Fah^{+/-}$ pigs were generated by creating an AAV targeting construct for homologous recombinant in fetal pig fibroblasts. The AAV targeting construct included an in-frame stop codon, a neomycin-resistance cassette and 5' and 3' homology arms that target the construct for insertion in exon 5 of the Fah gene. Fetal pig fibroblasts were infected with the AAV targeting vector and selected for neomycin resistance to isolate individual cell clones with integrated vector. Cells were expanded and DNA from each clone was evaluated by PCR to confirm proper targeting.

To generate $Fah^{+/-}$ pigs from fetal fibroblasts, SCNT was used. Mature oocytes were isolated from female pigs, cultured in vitro, enucleated and fused with donor fibroblasts. The resulting embryos were transferred into activated recipient gilts (young female pigs). Piglets arising from SCNT were screened by PCR and Southern blot confirm their $Fah^{+/-}$ status.

$Fah^{+/-}$ heterozygote pigs can be cross-bred to generate $Fah^{-/-}$ homozygote pigs. Newborn piglets are administered NTBC or a similar compound to prevent liver failure. Once genotyping is complete, all $Fah^{-/-}$ homozygote pigs remain on NTBC. If desired, the dose of NTBC can be lowered to promote cirrhosis or HCC in the Fah-deficient pig, or NTBC treatment can be eliminated once Fah-deficient pigs have been transplanted with human hepatocytes or hepatocytes derived from another species (such as, for example, mice, rats, dogs, cats, cows, horses or non-human primates, such as baboons, chimpanzees and rhesus macaques), as discussed below.

A. Expansion of Human Hepatocytes and their Medical Use

The present disclosure contemplates the use of human hepatocytes expanded in and collected from recipient pigs as a source of human hepatocytes for liver reconstitution in a subject in need of such therapy. Reconstitution of liver tissue in a patient by the introduction of hepatocytes is a potential therapeutic option for patients with acute liver failure, either as a temporary treatment in anticipation of liver transplant or as a definitive treatment for patients with isolated metabolic deficiencies (Bumgardner et al. *Transplantation* 65: 53-61, 1998). Hepatocyte reconstitution may be used, for example, to introduce genetically modified hepatocytes for gene therapy or to replace hepatocytes lost as a result of disease, physical or chemical injury, or malignancy (U.S. Pat. No. 6,995,299). For example, use of transfected hepatocytes in gene therapy of a patient suffering from familial hypercholesterolemia has been reported (Grossman et al. *Nat. Genet.* 6: 335, 1994). In addition, expanded human hepatocytes can be used to populate artificial liver assist devices. Particular methods of transplanting and expanding human hepatocytes in Fah-deficient pigs, as well medical uses of the expanded human hepatocytes, are described in greater detail below.

1. Pre-Immune Fetal Transplantation of Fah-Deficient Pigs

One method disclosed herein for expanding human hepatocytes in Fah-deficient pigs includes transplanting human hepatocytes into Fah-deficient pig fetuses. In this method, $Fah^{-/-}$ pigs are bred to each other to generate only homozygous Fah-knockout offspring. At approximately day 35-45 of gestation (such as day 40), the Fah-deficient pig fetus is surgically externalized and injected with human hepatocytes via the umbilical vein or directly into the fetal liver. The number of human hepatocytes injected can vary and will depend on the desired use, route of delivery and other factors. In some embodiments, the pig fetus is injected with 100,000 to $1\times10^8$, such as 500,000 to $1\times10^7$, human hepatocytes. In some examples, the pig fetus is injected with about $1\times10^6$ to about $1\times10^8$, such as about $1\times10^7$, human hepatocytes. In one non-limiting example, the pig fetus is injected with approximately $1\times10^7$ human hepatocytes directly into the fetal liver. In other examples, the number of human hepatocytes injected is about 100,000 to about 500,000, such as about 300,000. Because of the immature nature of the immune system during fetal development, the Fah-deficient pig fetus will develop tolerance to human hepatocytes. Thus, it is not necessary to treat a Fah-deficient pig that has been transplanted with human hepatocytes during fetal development with immunosuppressive agents.

The pregnant sow is maintained on NTBC or a similar compound to prevent liver dysfunction throughout pregnancy. The dose of NTBC can vary. In some embodiments, the dose of NTBC is about 0.2 mg/kg to about 2.0 mg/kg per day. In some examples, the dose of NTBC is about 1.0 mg/kg per day. The dose of NTBC can be modified as needed to prevent liver dysfunction in the Fah-deficient animals. After birth, the Fah-deficient pig engrafted with human hepatocytes will be taken off NTBC to permit expansion of the human hepatocytes. In some examples, the Fah-deficient pig will be taken off NTBC immediately after birth. In other examples, the dose of NTBC is gradually reduced over time, such as over about 1 to 6 days.

2. Post-Natal Transplantation of Fah-Deficient Pigs

A second method of expanding human hepatocytes in Fah-deficient pigs includes post-natal transplantation of the human hepatocytes into Fah-deficient pigs. In some embodiments, the Fah-deficient piglet is transplanted shortly after birth, such as within 2 days or within a week. In other embodiments, older Fah-deficient pigs, including adult Fah-deficient pigs, are transplanted. The human hepatocytes are generally transplanted via the hepatic artery, intrasplenic injection or portal vein. The Fah-deficient pigs are maintained on a pharmacologic inhibitor of phenylpyruvate dioxygenase, such as NTBC or methyl-NTBC, to prevent liver dysfunction. Prior to transplantation of the human hepatocytes, the Fah-deficient pigs are treated with one or more immunosuppressive agents to prevent rejection of the human hepatocytes. Typically, the one or more immunosuppressive agents are administered about two days prior to human hepatocyte transplantation; however, the timing for initiating treatment with the immunosuppressive agents can vary if necessary in order to achieve optimal results. Administration of the immunosuppressive agents will typically continue indefinitely to prevent rejection of the human hepatocytes.

Once transplantation of the human hepatocytes has been completed, the Fah-deficient pigs are taken off of NTBC to allow for expansion of the human hepatocytes. The presence of the human hepatocytes (which are not deficient for Fah) allows the animals to remain healthy in the absence of NTBC. In some cases, treatment with NTBC is stopped immediately after hepatocyte transplantation. In other cases, NTBC is gradually reduced over time, such as over about one to about six days. In some embodiments, the dose of NTBC when administered to the Fah-deficient pig, is about 0.2 mg/kg to about 2.0 mg/kg per day. In some examples, the dose of NTBC is about 1.0 mg/kg per day. The dose of NTBC can be modified as needed to prevent liver dysfunction in the Fah-deficient animals.

In some cases, post-natal transplantation is used in pigs that were tolerized with human hepatocytes in utero.

3. Transplantation of Human Hepatocytes into Fah-Deficient Pigs

Any suitable source of human hepatocytes or hepatocyte precursors/progenitors can be used in the disclosed methods for transplantation in Fah-deficient pigs. For example, human hepatocytes can be derived from cadaveric donors or liver resections, or can be obtained from commercial sources. It is anticipated that it will be possible to transplant Fah-deficient pigs with human hepatocytes from donors of all ages or with cryopreserved hepatocytes. There is often a delay (typically 1 to 2 days) between isolation of human hepatocytes and transplantation, which can result in poor viability of the hepatocytes. However, the Fah-deficient pig system can serve as a means of expanding human hepatocytes even when the number of hepatocytes is limited in number.

Methods of isolating human hepatocytes are well known in the art. For example, methods of isolating human hepatocytes from organ donors or liver resections are described in PCT Publication Nos. WO 2004/009766 and WO 2005/028640 and U.S. Pat. Nos. 6,995,299 and 6,509,514. Hepatocytes can be obtained from a liver biopsy taken percutaneously or via abdominal surgery. Human hepatocytes for transplantation into a recipient animal, such as a Fah-deficient pig, can be isolated from human liver tissue by any convenient method known in the art. Liver tissue can be dissociated mechanically or enzymatically to provide a suspension of single cells, or fragments of intact human hepatic tissue may be used. For example, the hepatocytes can be isolated from donor tissue by routine collagenase perfusion (Ryan et al. *Meth. Cell Biol.* 13:29, 1976) followed by low-speed centrifugation. Hepatocytes can then be purified by filtering through a stainless steel mesh, followed by density-gradient centrifugation. Alternatively, other methods for enriching for hepatocytes can be used, such as, for example, fluorescence activated cell sorting, panning, magnetic bead separation, elutriation within a centrifugal field, or any other method well known in the art. Similar hepatocyte isolation methods can be used to collect expanded human hepatocytes from recipient animal liver (e.g., Fah-deficient pig liver).

Alternatively, human hepatocytes can be prepared using the technique described by Guguen-Guillouzo et al. (*Cell Biol. Int. Rep.* 6:625-628, 1982). Briefly, a liver or portion thereof is isolated and a cannula is introduced into the portal vein or a portal branch. The liver tissue is then perfused, via the cannula, with a calcium-free buffer followed by an enzymatic solution containing collagenase (such as about 0.025% collagenase) in calcium chloride solution (such as about 0.075% calcium chloride) in HEPES buffer at a flow rate of between 30 and 70 milliliters per minute at 37° C. The perfused liver tissue is minced into small (such as about 1 cubic millimeter) pieces. The enzymatic digestion is continued in the same buffer as described above for about 10-20 minutes with gentle stirring at 37° C. to produce a cell suspension. The released hepatocytes are collected by filtering the cell suspension through a 60-80 micrometer nylon mesh. The collected hepatocytes can then be washed in cold HEPES buffer at pH 7.0 using slow centrifugation to remove collagenase and cell debris. Non-parenchymal cells may be removed by metrizamide gradient centrifugation (see U.S. Pat. No. 6,995,299).

Human hepatocytes can be obtained from fresh tissue (such as tissue obtained within hours of death) or freshly frozen tissue (such as fresh tissue frozen and maintained at or below about 0° C.). For some applications, it is preferred that the human tissue has no detectable pathogens, is normal in morphology and histology, and is essentially disease-free. The hepatocytes used for engraftment can be recently isolated, such as within a few hours, or can be transplanted after longer periods of time if the cells are maintained in appropriate storage media. One such media is VIASPAN™ (a universal aortic flush and cold storage solution for the preservation of intra-abdominal organs; also referred to as University of Wisconsin solution, or UW). Hepatocytes also can be cryopreserved prior to transplantation. Methods of cryopreserving hepatocytes are well known in the art and are described, for example, in U.S. Pat. No. 6,136,525.

In addition to obtaining human hepatocytes from organ donors or liver resections, the cells used for engraftment can be human stem cells or hepatocyte precursor cells which, following transplantation into the recipient animal, develop or differentiate into human hepatocytes capable of expansion. Human cells with ES cell properties have been isolated from the inner blastocyst cell mass (Thomson et al., *Science* 282: 1145-1147, 1998) and developing germ cells (Shamblott et al., *Proc. Natl. Acad. Sci. USA* 95:13726-13731, 1998), and human embryonic stem cells have been produced (see U.S. Pat. No. 6,200,806). As disclosed in U.S. Pat. No. 6,200,806, ES cells can be produced from human and non-human primates. Induced pluripotent stem (iPS) cells induced from human and non-human primate cells can also be obtained (see, for example, Yu et al., *Science* 318(5858):1917-1920, 2007; Takahashi et al., *Cell* 131(5):861-872, 2007; Liu et al., *Cell Stem Cell* 3(6):587-590, 2008). Generally, primate ES cells are isolated on a confluent layer of murine embryonic fibroblast in the presence of ES cell medium. ES cell medium generally consists of 80% Dulbecco's modified Eagle's medium (DMEM; no pyruvate, high glucose formulation, Gibco BRL), with 20% fetal bovine serum (FBS; Hyclone), 0.1 mM β-mercaptoethanol (Sigma), and 1% non-essential amino acid stock (Gibco BRL). Distinguishing features of ES cells, as compared to the committed "multipotential" stem cells present in adults, include the capacity of ES cells to maintain an undifferentiated state indefinitely in culture, and the potential that ES cells have to develop into every different cell type. Human ES (hES) cells express SSEA-4, a glycolipid cell surface antigen recognized by a specific monoclonal antibody (see, for example, Amit et al., *Devel. Biol.* 227:271-278, 2000).

Human hepatocytes derived from human mesenchymal stem cells (hMSCs) can also be used in the methods described herein. Sequential exposure of bone marrow-derived hMSCs to hepatogenic factors results in differentiation of the stem cells to cells with hepatocyte properties (see Snykers et al. *BMC Dev Biol.* 7:24, 2007; Aurich et al. *Gut.* 56(3):405-15, 2007). Hepatogenic differentiation of bone marrow-derived mesenchymal stem cells and adipose tissue-derived stem cells (ADSCs) has also been described (see Talens-Visconti et al. *World J. Gastroenterol.* 12(36):5834-45, 2006). Human hepatocytes can also be generated from monocytes. Ruhnke et al. (*Transplantation* 79(9):1097-103, 2005) describe the generation of hepatocyte-like (NeoHep) cells from terminally differentiated peripheral blood monocytes. The NeoHep cells resemble primary human hepatocytes with respect to morphology, expression of hepatocyte markers, various secretory and metabolic functions and drug detoxification activities. In addition, human hepatocytes derived from amniocytes, also can be used in the methods described herein.

Human ES cell lines exist and can be used in the methods disclosed herein. Human ES cells can also be derived from preimplantation embryos from in vitro fertilized (IVF) embryos. Experiments on unused human IVF-produced embryos are allowed in many countries, such as Singapore and the United Kingdom, if the embryos are less than 14 days old. Only high quality embryos are suitable for ES cell isolation. Culture conditions for culturing the one cell human embryo to the expanded blastocyst have been described (see, for example, Bongso et al., *Hum Reprod.* 4:706-713, 1989). Co-culturing of human embryos with human oviductal cells results in the production of high blastocyst quality. IVF-derived expanded human blastocysts grown in cellular co-culture, or in improved defined medium, allows isolation of human ES cells (see U.S. Pat. No. 6,200,806).

4. Collecting Human Hepatocytes from Fah-Deficient Pigs

Human hepatocytes can be collected from recipient animals using any of a number of techniques known in the art. For example, pigs can be anesthetized and the portal vein or inferior vena cava cannulated with a catheter. The liver can then be perfused with an appropriate buffer (such as a calcium- and magnesium-free EBSS supplemented with 0.5 mM EGTA and 10 mM HEPES), followed by collagenase treatment (for example, using a solution was of EBSS supplemented with 0.1 mg/ml collagenase XI and 0.05 mg/ml DNase I). The liver can be gently minced and filtered through nylon mesh (such as sequentially through 70 μm and 40 μm nylon mesh), followed by centrifugation and washing of the cells.

Human hepatocytes collected from recipient animals can be separated from non-human cells or other contaminants (such as tissue or cellular debris) using any technique well known in the art. For example, such methods include using an antibody which selectively binds to human hepatocytes. Such antibodies include, but are not limited to an antibody that specifically binds to a class I major histocompatibility antigen, such as anti-human HLA-A,B,C (Markus et al. *Cell Transplantation* 6:455-462, 1997) or CD46. Antibodies specific for human cells or human hepatocytes can be used in a variety of different techniques, including fluorescence activated cell sorting (FACS), panning or magnetic bead separation. Alternatively, antibodies which bind selectively to pig cells can be used to remove contaminating pig cells and thereby enrich human hepatocytes. FACS employs a plurality of color channels, low angle and obtuse light-scattering detection channels, and impedance channels, among other more sophisticated levels of detection, to separate or sort cells (see U.S. Pat. No. 5,061,620) bound by the antibody. Magnetic separation involves the use of paramagnetic particles which are: 1) conjugated to the human-specific antibodies; 2) conjugated to detection antibodies which are able to bind to the human-specific antibodies; or 3) conjugated to avidin which can bind to biotinylated antibodies. Panning involves a monoclonal antibody attached to a solid matrix, such as agarose beads, polystyrene beads, hollow fiber membranes or plastic petri dishes. Cells that are bound by the antibody can be isolated from a sample by simply physically separating the solid support from the sample.

Hepatocytes collected from Fah-deficient pigs can be, for example, cryopreserved for later use, or plated in tissue culture for shipping and future use.

5. Human Liver Reconstitution

Fah-deficient pigs provide a system for propagating human hepatocytes that can be used to reconstitute a human liver, as alternative or adjunct to liver transplant. Currently, patients suffering from liver disease may have to wait for long periods of time before a suitable organ for transplant becomes available. After transplant, patients need to be treated with immunosuppressive agents for the duration of their lives in order to avoid rejection of the donor's liver. A method for propagating the patient's own cells could provide a source of functional liver tissue which would not require immunosuppression to remain viable. Accordingly, the Fah-deficient pigs disclosed herein can be used to reconstitute the liver of a subject with liver disease and/or liver failure using their own hepatocytes, including those produced from patient specific stem cells, that have been expanded in the Fah-deficient pigs, or hepatocytes from a donor.

Reconstitution of liver tissue in a patient by the introduction of hepatocytes (also referred to as "hepatocyte transplantation") is a potential therapeutic option for patients with acute liver failure, either as a temporary treatment in anticipation of liver transplant or as a definitive treatment for patients with isolated metabolic deficiencies (Bumgardner et al., *Transplantation* 65: 53-61, 1998). A major obstacle to achieving therapeutic liver reconstitution is immune rejection of transplanted hepatocytes by the host, a phenomenon referred to (where the host and donor cells are genetically and phenotypically different) as "allograft rejection." Immunosuppressive agents have been only partially successful in preventing allograft rejection (Javregui et al., *Cell Transplantation* 5: 353-367, 1996; Makowka et al., *Transplantation* 42: 537-541, 1986). Human hepatocytes expanded in Fah-deficient pigs may also be used for gene therapy applications. In the broadest sense, such hepatocytes are transplanted into a human host to correct a genetic defect. The passaged hepatocytes need not, but can be derived originally from the same individual who is to be the recipient of the transplant.

In some embodiments, human hepatocytes expanded in Fah-deficient pigs may be used to reconstitute liver tissue in a subject as a prelude or an alternative to liver transplant. As one non-limiting example, a subject suffering from progressive degeneration of the liver, for example, as a result of alcoholism, may serve as a donor of hepatocytes which are then expanded in a Fah-deficient pig. The number of hepatocytes is expanded relative to the number originally obtained from the subject and transplanted into the Fah-deficient pig. Following expansion, the human hepatocytes can be isolated from the Fah-deficient pig and can be used to reconstitute the subject's liver function. Expanding hepatocytes in Fah-deficient pigs may be used not only to increase the number of hepatocytes, but also to selectively remove hepatocytes that are afflicted with infectious or malignant disease. Specifically, a subject may be suffering from hepatitis, where some but not all of the hepatocytes are infected and infected hepatocytes can be identified by the presence of viral antigens in or on the cell surface. In such an instance, hepatocytes can be collected from the subject, and non-infected cells can be selected for expanding in one or more Fah-deficient pigs, for example by FACS. Meanwhile, aggressive steps could be taken to eliminate infection in the patient. Following treatment, the subject's liver tissue may be reconstituted by hepatocytes expanded in the one or more Fah-deficient pigs. An analogous method could be used to selectively passage non-malignant cells from a patient suffering from a liver malignancy, such as HCC.

B. Porcine Model of HT1

Hereditary tyrosinemia type 1 (HT1) is a severe autosomal recessive metabolic disease that affects the liver and kidneys. HT1 results from defects in the Fah gene, located in q23-q25 of chromosome 15 in humans and in chromosome 7 in mice. HT1 patients display a variety of clinical symptoms, such as liver damage from infancy that advances to cirrhosis; reduced coagulation factors; hypoglycemia; high concentrations of methionine, phenylalanine, and aminolevulinic acid in serum plasma; high risk of hepatocellular carcinoma; and tubular and glomerular renal dysfunction. In its severe form, a pattern of progressive liver damage begins from early infancy. In its mild form, chronic liver damage with a high incidence of hepatoma is characteristic.

Mice homozygous for Fah gene disruption have a neonatal lethal phenotype caused by liver dysfunction. It has previously been demonstrated that treatment of Fah-deficient mice with NTBC restores liver function and abolishes neonatal lethality (Grompe et al., *Nat Genet.* 10:453-460, 1995). The prolonged lifespan of these animals resulted in a phenotype analogous to HT1 in humans, including the development of hepatocellular carcinoma and fibrosis. Accordingly, the Fah-deficient pigs disclosed herein represent a large animal model of the human disease HT1.

Currently, the most effective therapy for HT1 is liver transplantation. This procedure is associated with significant morbidity, mortality and cost. Thus, improved methods of treatment (such as pharmacological inhibition or gene therapy) are needed. The Fah-deficient pigs disclosed herein provide a large animal model to evaluate the efficacy of potential HT1 treatments. It is contemplated herein to use Fah-deficient pigs to evaluate a variety of different types of HT1 therapies, including screening for pharmaceutical agents that alleviate the disease, evaluating gene therapies (for example, but introducing a heterologous nucleic acid sequence into the human hepatocytes transplanted in the Fah-deficient pigs), and assessing dietary modifications.

C. Liver Disease Model

As discussed above, Fah deficiency in animals leads to a disease phenotype similar to the human disease HT1. To prevent lethality, Fah-deficient animals are maintained on NTBC or a similar compound to prevent liver dysfunction, however, titration of the dose of NTBC can be used promote the development of HT1-type phenotypes, including HCC, fibrosis and cirrhosis. Accordingly, the Fah-deficient pigs disclosed herein can be used to study a variety of liver diseases, including HCC and cirrhosis.

In some embodiments, the Fah-deficient pigs disclosed herein are used as a large animal model of human liver disease. Fah-deficient pigs may be used as models of liver disease resulting from, for example, exposure to a toxin, infectious disease or malignancy or a genetic defect (i.e., Fah-deficiency leading to HT1). Examples of human genetic liver diseases for which Fah-deficient pigs may serve as a model include, but are not limited to, hypercholesterolemia, hypertriglyceridemia, hyperoxaluria, phenylketonuria, maple syrup urine disease, glycogen storages diseases, lysosomal storage diseases (such as Gaucher's disease), and any inborn error of metabolism. The disclosed model systems can be used to gain a better understanding of particular liver diseases and to identify agents which may prevent, retard or reverse the disease processes.

Where the Fah-deficient pig is to be used as a model for liver disease caused by a toxin, the Fah-deficient pig is maintained on NTBC to prevent liver dysfunction. The amount of toxic agent required to produce results most closely mimicking the corresponding human condition may be determined by using a number of Fah-deficient pigs exposed to incremental doses of the toxic agent. Examples of toxic agents include, but are not limited to, ethanol, acetaminophen, phenyloin, methyldopa, isoniazid, carbon tetrachloride, yellow phosphorous and phalloidin. In some cases, the Fah-deficient pig in the absence of human hepatocytes is used as the model for evaluating the effect of a toxin. In other examples, the Fah-deficient pig is transplanted with human hepatocytes to evaluate the effect of the toxin on human hepatocytes. In these examples, it is not necessary to maintain the Fah-deficient pigs on NTBC. Typically, expansion of human hepatocytes is allowed to proceed to the point where the size of the human hepatocyte population is substantial (e.g. has approached a maximum), before the Fah-deficient pig is exposed to the toxic agent.

In embodiments where a Fah-deficient pig is to be used as a model for malignant liver disease (such as HCC or hepatoma), the Fah-deficient pig is administered a high enough dose of NTBC to prevent fatality due to liver dysfunction, but low enough to allow the development of HCC or other liver malignancy. Alternatively, the Fah-deficient pig can be maintained on a dose of NTBC that prevents any liver dysfunction and the malignancy can be produced by exposure to a transforming agent or by the introduction of malignant cells. In some examples, the Fah-deficient pig in the absence of human hepatocytes is used as the model for malignant liver disease. In other examples, the Fah-deficient pig is transplanted with human hepatocytes to evaluate malignant liver disease of the human cells. In these examples, it is not necessary to maintain the Fah-deficient pigs on NTBC. The transforming agent or malignant cells may be introduced with the initial colonizing introduction of human hepatocytes or after the human hepatocytes have begun to proliferate in the host animal. In the case of a transforming agent, it may be preferable to administer the agent at a time when human hepatocytes are actively proliferating.

Examples of transforming agents include aflatoxin, dimethylnitrosamine, and a choline-deficient diet containing 0.05-0.1% w/w DL-ethionine (Farber and Sarma, 1987, in Concepts and Theories in Carcinogenesis, Maskens et al., eds, Elsevier, Amsterdam, pp. 185-220). Such transforming agents may be administered either systemically to the animal or locally into the liver itself. Malignant cells may be inoculated directly into the liver.

D. Model for Hepatic Infections

Human hepatocytes expanded in and collected from Fah-deficient pigs can also be used for a variety of microbiological studies. A number of pathogens (e.g., bacteria, viruses and parasites) will only replicate in a human host or in primary human hepatocytes. Thus, having a sufficient source of primary human hepatocytes is critical for studies of these pathogens. The expanded human hepatocytes can be used for studies of viral infection and replication or for studies to identify compounds that modulate infection of hepatic viruses. Methods of using primary human hepatocytes for studies of hepatic viruses are described in, for example, European Patent No. 1552740, U.S. Pat. No. 6,509,514 and PCT Publication No. WO 00/17338. Examples of hepatic viruses include hepatitis A virus, hepatitis B virus (HBV), hepatitis C virus (HCV) and cytomegalovirus (CMV). Examples of parasites that infect the liver include, for example, the causative agents of malaria (*Plasmodium* species, including *Plasmodium falciparum, Plasmodium vivax, Plasmodium ovale, Plasmodium malariae* and *Plasmodium knowlesi*) and the causative agents of leishmaniasis (*Leishmania* species, including *L. donovani, L. infantum, L. chagasi, L. mexicana, L. amazonensis, L. venezuelensis, L. tropica; L. major; L. aethiopica, L. (V.) braziliensis, L. (V.) guyanensis, L. (V.) panamensis*, and *L. (V.) peruviana*).

In addition to using the human hepatocytes expanded in Fah-deficient pigs for microbiological studies, the Fah-deficient pigs themselves can serve as animal models of hepatic pathogen infection. For example, Fah-deficient pigs repopulated with human hepatocytes can be infected with a hepatic pathogen and used to screen candidate agents for treatment of the infection. Candidate agents include any compound from any one of a number of chemical classes, such as small organic compounds. Candidate agents also include biomolecules, such as, for example, nucleic acid molecules (including antisense oligonucleotides, small interfering RNAs, microRNAs, ribozymes, short hairpin RNAs, expression vectors and the like), peptides and antibodies, saccharides, fatty acids, steroids, purines, pyrimidines, derivatives, structural analogs or combinations thereof.

Candidate agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Using Fah-deficient pigs to study HCV and HBV infection, as well as evaluate candidate agents for the treatment of these infections, is discussed below. However, the methods can be applied to any hepatic pathogen of interest. In one embodiment, a Fah-deficient pig is used to identify agents that inhibit viral infection, decrease viral replication, and/or ameliorate one or more symptoms caused by HBV or HCV infection. In general, the candidate agent is administered to the Fah-deficient pig, and the effects of the candidate agent assessed relative to a control. For example, the candidate agent can be administered to an HCV-infected Fah-deficient pig, and the viral titer of the treated animal (e.g., as measured by RT-PCR of serum samples) can be compared to the viral titer of the animal prior to treatment and/or to an untreated HCV-infected animal. A detectable decrease in viral titer of an infected animal following treatment with a candidate agent is indicative of antiviral activity of the agent.

The candidate agent can be administered in any suitable manner appropriate for delivery of the agent. For example, the candidate agent can be administered by injection (such as by injection intravenously, intramuscularly, subcutaneously, or directly into the target tissue), orally, or by any other desirable means. In some cases, the in vivo screen will involve a number of Fah-deficient pigs receiving varying amounts and concentrations of the candidate agent (from no agent to an amount of agent that approaches an upper limit of the amount that can be safely delivered to the animal), and may include delivery of the agent in different formulations and routes. Candidate agents can be administered singly or in combinations of two or more, especially where administration of a combination of agents may result in a synergistic effect.

The activity of the candidate agent can be assessed using any one of a variety of means known in the art. For example, where the Fah-deficient pig is infected with a hepatotropic pathogen (e.g., HBV or HCV), the effect of the agent can be assessed by examining serum samples for the presence of the pathogen (e.g., measuring viral titer) or markers associated with the presence of the pathogen (e.g., a pathogen-specific protein or encoding nucleic acid). Qualitative and quantitative methods for detecting and assessing the presence and severity of viral infection are well known in the art. In one embodiment, the activity of an agent against HBV infection can be assessed by examining serum samples and/or tissue sections for the presence of a viral antigen (such as HBV surface antigen (HBsAg) or HBV core antigen (HbcAg)). In another embodiment, the activity of an agent against viral infection can be assessed by examining serum samples for the presence of viral nucleic acid (such as HCV RNA). For example, HCV RNA can be detected using, for example, reverse transcriptase polymerase chain reaction (RT-PCR), competitive RT-PCR or branched-DNA (bDNA) assay, detection of negative-strand RNA (the replicative intermediate of HCV) by RT-PCR, or sequencing of viral RNA to detect mutation/shift in the viral genome ("quasispecies evolution") with therapy. Alternatively or in addition, the host liver may be biopsied and in situ RT-PCR hybridization performed to demonstrate directly any qualitative or quantitative alterations in the amount of viral particles within tissue sections. Alternatively or in addition, the host can be euthanized and the liver examined histologically for signs of infection and/or toxicity caused by the agent.

Fah-deficient pigs can also be used to screen candidate vaccines for their ability to prevent or ameliorate infection by a hepatotropic pathogen. In general, a vaccine is an agent that, following administration, facilitates the host in mounting an immune response against the target pathogen. The humoral, cellular, or humoral/cellular immune response elicited can facilitate inhibition of infection by the pathogen against which the vaccine is developed. Of particular interest in the present disclosure are vaccines that elicit an immune response that inhibits infection by and/or intrahepatic replication of a hepatotropic pathogen (e.g., a microbial, viral, or parasitic pathogen), particularly a viral pathogen, such as HBV and/or HCV.

To evaluate candidate vaccines, the Fah-deficient pigs are transplanted with human hepatocytes to repopulate the pig liver with human hepatocytes. Screening for an effective vaccine is similar to the screening methods described above. In some embodiments, the candidate vaccine is administered to the Fah-deficient pig prior to inoculation with the hepatotropic pathogen. In some cases, the candidate vaccine is administered by providing a single bolus (e.g., intraperitoneal or intramuscular injection, topical administration, or oral administration), which is optionally followed by one or more booster immunizations. The induction of an immune response can be assessed by examining B and T cell responses that are specific for the antigen/vaccine according to methods well known in the art. The immunized Fah-deficient pig is then challenged with the hepatotropic pathogen. Typically, several immunized animals are challenged with increasing titers of the pathogen. The animals are then observed for development of infection, and the severity of infection is assessed (such as by assessing the titer of the pathogen present, or examining human hepatocyte function parameters). Vaccine candidates that provide for a significant decrease in infection by the pathogen and/or a significant decrease in the severity of disease that results post-challenge are identified as viable vaccines.

E. Pharmacology, Toxicology and Gene Therapy Studies

Fah-deficient pigs and/or human hepatocytes expanded in and collected from Fah-deficient pigs can be used to evaluate alterations in gene expression in human hepatocytes by any pharmacologic compound, such as small molecules, biologicals, environmental or biological toxins or gene delivery systems.

For example, human hepatocytes expanded in and collected from Fah-deficient pigs can be used to evaluate toxicity of particular compounds in human cells. Methods of testing toxicity of compounds in isolated hepatocytes are well known in the art and are described, for example, in PCT Publication No. WO 2007/022419. Similarly, Fah-deficient pigs transplanted with human hepatocytes can be used to evaluate the toxicity of exogenous agents. In some embodiments, the exogenous agent is a known or suspected toxin.

In some embodiments, Fah-deficient pigs transplanted with human hepatocytes (or human hepatocytes expanded in and collected from Fah-deficient pigs) are used to evaluate any one of a number of parameters of drug metabolism and pharmacokinetics. For example, studies can be carried out to evaluate drug metabolism, drug/drug interactions in vivo, drug half-life, routes of excretion/elimination, metabolites in the urine, feces, bile, blood or other bodily fluid, cytochrome p450 induction, enterohepatic recirculation, and enzyme/transporter induction.

In some embodiments, Fah-deficient pigs transplanted with human hepatocytes (or human hepatocytes expanded in and collected from Fah-deficient pigs) are used to evaluate toxicology and safety of a compound, including therapeutic agents or candidate agents (such as small molecules or biologicals), environmental or biological toxins, or gene delivery systems. For example, cell cycle proliferation in human hepatocytes can be evaluated, such as to determine the risk of cancer following exposure to the compound. Toxicity to hepatocytes can also be assessed, such as by histology, apoptosis index, liver function tests and the like. Analysis of hepatocyte metabolism can also be performed, such as analysis of metabolites after infection of stable isotope precursors.

The efficacy of particular drugs can also be evaluated in Fah-deficient pigs transplanted with human hepatocytes. Such drugs include, for example, drugs to treat hyperlipidemia/atherosclerosis, hepatitis and malaria.

In some embodiments, Fah-deficient pigs transplanted with human hepatocytes (or human hepatocytes expanded in and collected from Fah-deficient pigs) are used to study gene therapy protocols and vectors. For example, the following parameters can be evaluated: transduction efficiency of gene delivery vehicles including viral and non-viral vectors; integration frequency and location of genetic payloads (integration site analysis); functionality of genetic payloads (gene expression levels, gene knockdown efficiency); and side effects of genetic payloads (analysis of gene expression or proteomics in human hepatocytes in vivo).

The following examples are provided to illustrate certain particular features and/or embodiments. These examples should not be construed to limit the disclosure to the particular features or embodiments described.

EXAMPLES

Example 1

Materials and Methods

This example describes the experimental procedures for the studies described in Examples 2 and 3.

Genomic Clone Construction

Genomic DNA was isolated and purified (Qiamp; Qiagen) from pig fetal liver. Two fragments of DNA, adjacent to exon 5 of the Fah locus of chromosome 7, were amplified using primers MG2616 and MG2678 (left homologous recombination arm; 1479 bp) and MG2619 and MG2680 (right homologous recombination arm; 1523 bp) (see Table 1 for sequences) and a high fidelity polymerase (Phusion; Finnzymes). SEQ ID NO: 1 provides the nucleotide sequence of 20 kb around exon 5 of the Fah gene in pigs. Primers were designed based on the domestic pig working draft genomic sequence (Genbank accessions CU468492 and CU467891). These PCR products were subcloned into pCR-Blunt II-TOPO (Invitrogen) and confirmed by restriction digest and sequencing.

Fah-Null Targeting Vector Construction

The overall strategy to knockout the Fah gene was to insert an in-frame stop codon and a neomycin-resistance cassette (PGK-neo) into exon 5 of the porcine Fah gene. To generate a PGK-neo expression cassette, with an additional in-frame TGA stop codon at the 5' end, a 1681 bp fragment was amplified using primers MG2622 and MG2679, subcloned into pCR-Blunt II-TOPO, and confirmed by restriction digest and sequencing.

Figure 4A:
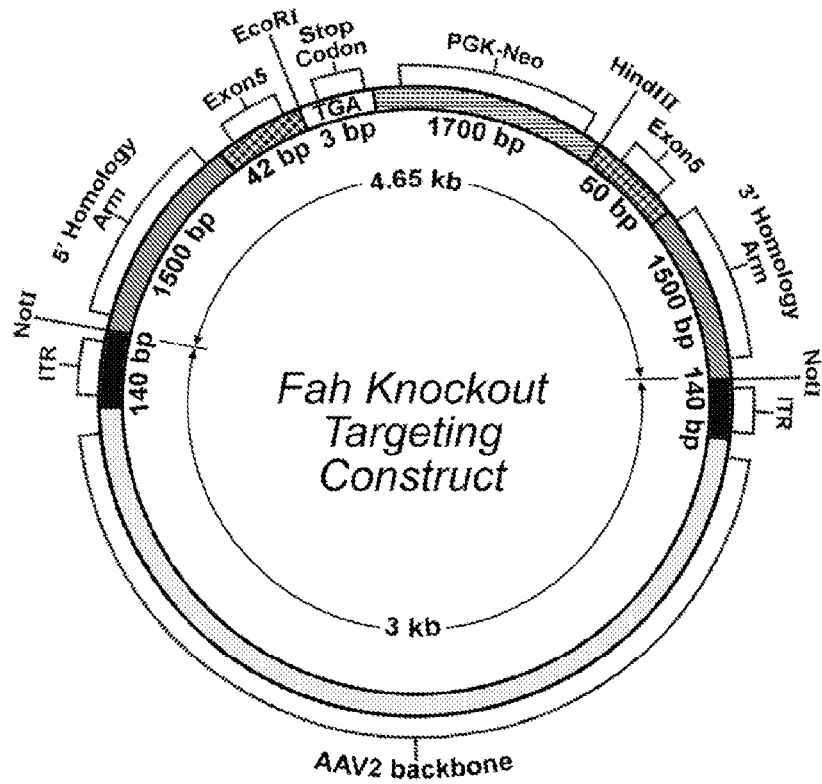
FIGS. 4A and 4B are schematic drawings of the Fah knock-out targeting construct (A) and the genotyping construct (B).

The PGK promoter is ubiquitously active and it was shown to work in pig fibroblasts. This strategy is similar to the creation of the CFTR-null pig (Welsh et al., *Trans Am Clin Climatol Assoc* 120:149, 2009; Rogers et al., *Science* 321: 1837, 2008). The frequency of homologous recombination with adeno-associated virus (AAV) vectors is significantly higher when the targeting event is an insertion and does not involve deletion of genomic sequences. The packaging limit of the AAV capsid is 4.7 kb and thus this construct contains two homology arms of 1.5 kb each and a 1.7 kb PGK-neo cassette, as illustrated in FIG. 4A (1.7+1.5+1.5=4.7).

To generate the two 1.5 kb homology arms from genomic DNA, PCR was used to amplify genomic DNA. The strategy used to generate the targeting vector is schematically depicted in FIG. 2. The PCR-primers located within exon 5 were designed to contain tails that introduced the stop codon as well as restriction sites that facilitated facile ligation into the PGK-neo expression vector. Unique restriction sites were then used for the 5' and 3' homology arms. This PCR-based strategy to generate the targeting construct was straightforward. Exon 5 was chosen for the insertion based on the following criteria: a) there was sufficient high quality sequence from the flanking genomic DNA to design the PCR primers and b) this area of the genomic sequence is highly conserved when compared to the human and mouse Fah gene. Additionally, exon 5 is was preferred because the murine Fah knockout previously generated by the inventors is an exon 5 insertion.

To generate the complete targeting vector, each fragment was sequentially subcloned into pcDNA3.1-(Invitrogen) and orientation confirmed by restriction digest and sequencing. Once the full-sized 4683 bp-targeting construct was generated, it was cloned into an AAV2 plasmid backbone, thus providing it with the inverted terminal repeat (ITR) sequences required for viral packaging (FIG. 4A). This final targeting construct was sequenced to ensure accuracy before production of the final AAV vector. The nucleotide sequence of the targeting construct is set forth herein as SEQ ID NO: 2.

Production of the AAV Vector

The AAV packaging helper used in this study expresses a hybrid capsid containing AAV2, AAV5 and AAV8 capsid proteins and the AAV2 rep protein (Grimm et al., *J Virol* 82:5887, 2008). The targeting AAV-DJ vector was generated by standard calcium-phosphate triple transfection methods. This involved the transduction of HEK293 cells with equal amounts of the following plasmids: the AAV packaging helper containing the AAV2rep and AAV-DJ cap genes, the adenoviral helper pladeno5, and the AAV-targeting construct (FIG. 4A). To generate a large virus prep ($10^{13}$ particles) that can be used for the entire project, 30 150 mm plates of 293 cells were prepared. After transfection of all 3 plasmids into the cells, crude AAV particle-extracts were prepared by subjecting the 293 cells to multiple rounds of freezing and thawing. Crude extracts of the viral prep were used to infect and target fetal fibroblasts.

Fetal Fibroblasts

Porcine fetal fibroblasts were isolated from day 35 fetuses as previously described (Lai and Prather, *Cloning Stem Cells* 5:233-241, 2003). Fetal gender was determined by PCR amplification of the Sry gene on the Y chromosome (Pomp et al., *J Anim Sci* 73:1408-1415, 1995). Cells were initially grown in a 37° C., 5% $CO_2$ humidified incubator in high glucose DMEM media (HyClone), containing 15% fetal bovine serum (HyClone) and antimicrobials (100 U/ml penicillin, 100 µg/ml streptomycin and 0.25 µg/ml Amphotericin B; Cellgro).

Infection and Selection

Fetal fibroblasts ($1.0 \times 10^6$) were thawed and plated on a 100 mm collagen I-coated culture dish (Biocoat; BD Biosciences). After 24 hours, cells were infected with virus (200 µl, $3 \times 10^{11}$ viral particles/ml). Cells were trypsinized (0.05% Trypsin; HyClone) 22 hours later and 500-2000 cells were transferred to 96-well collagen I-coated plates in media supplemented with 150 µg/ml G418. Ten to twelve days later, cells were again trypsinized and split three different ways. For future cell freezing, 20% of the cells were transferred to a 96-well collagen I-coated plate. For cell expansion and further molecular analyses, 20% of the cells were transferred to an additional 96-well collagen I-coated plate. For PCR screening, 60% of the cells were transferred to a 96-well PCR plate.

PCR Screening

Figure 4B:
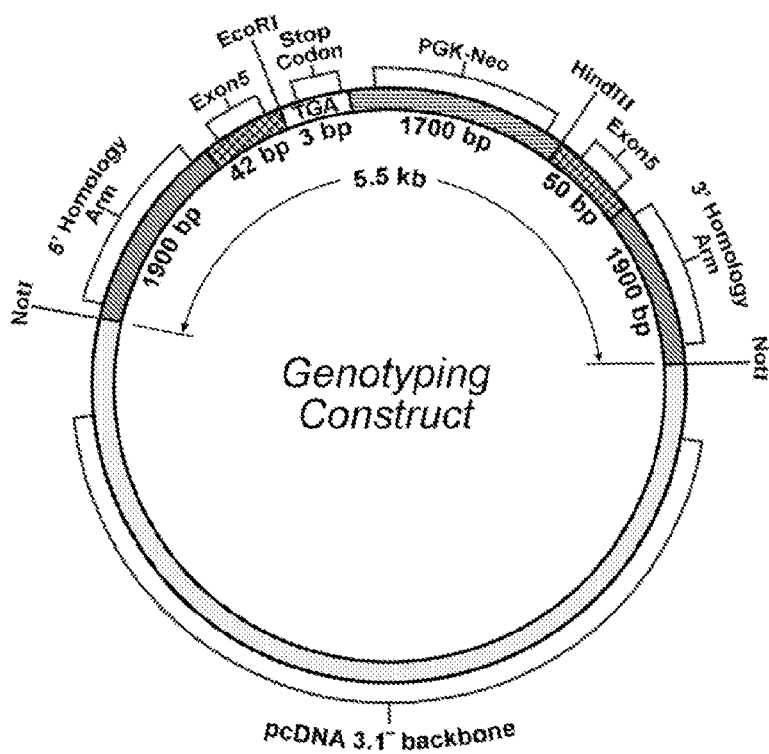

The rapid detection of properly targeted fibroblast clones requires a robust and rapid screening methodology. A PCR-based screening strategy was created that has been carefully optimized. One primer is placed in the PGK-neo cassette and the other outside the 1.5 kb targeting homology but within the Fah gene (see FIG. 4B). Cells in the 96-well PCR plates were spun down and washed in 250 µl of PBS. The plates were spun again, and the cell pellets resuspended in 5 µl lysis buffer (stock lysis solution=660 µl 0.01% SDS; 60 µl 10 mg/ml proteinase K; 30 µl 0.5M EDTA). Following a 90-minute incubation at 50° C. and 30-minute denaturation at 95° C., 1 µl of the lysed cells were used for each 25 µl PCR reaction. Primer pairs MG2844/2821 and MG2824/2851 (see Table 1 for sequences) were used to detect targeted integration at the 5' and 3' ends, respectively. PCR conditions were as follows: 3 minutes at 98° C., 40 cycles of 98° C. for 10 seconds, 68° C. for 20 seconds, and 72° C. for 75 seconds, and then 72° C. for 5 minutes. PCR generated products of 1622 bp and 1774 bp at the 5' and 3' ends, respectively, which were electrophoresed on a 2.0% TAE agarose gel and visualized with ethidium bromide staining.

If the Fah locus is properly targeted by homologous recombination, this primer combination yields a ~1.6 kb fragment, whereas amplification cannot occur if the plasmid integrates randomly. This PCR fragment can be reliably created with small amounts of genomic DNA.

The screening strategy was validated by first creating a plasmid that contains the same sequence as the properly targeted locus. This plasmid construct was inserted into the genomic DNA of control pig fetal fibroblasts using calcium precipitation and G418 selection. The DNA from these control cells was then used to optimize the PCR conditions. In order to construct the control plasmid, a PCR reaction very similar to that used to generate the targeting construct, but with slightly larger homology arms, was performed such that DNA sequence outside the targeting homology is represented. Homology arms 1.9 kb in size, instead of 1.5 kb, were created containing an additional 400 bp of genomic sequence. These larger homology arms were ligated into the PGK-neo cassette just as in the targeting construct itself (FIG. 4A). Once constructed, the plasmid was chemically transduced into a pig fetal fibroblast cell line, followed by G418 selection to isolate clones in which the PGK-neo was integrated. Several G418 resistant colonies were picked, expanded and genomic DNA isolated. This DNA was then used to test primer combinations and PCR cycling conditions until a robust signal could be obtained. These exact conditions were used to screen G418-resistant clones obtained from infecting fetal fibroblasts with the AAV-DJ targeting vector.

Processing of Positive Clones

Following identification of double positive (5' and 3' PCR products) PCR clones, cells in the freezing-down 96-well plate were grown to 90% confluency and trypsinized with 30 µl 0.05% Trypsin. Fifteen µl of detached cells were placed into each of two cryovials (Nalgene) and 300 µl of freezing media (90% FBS; 10% DMSO) was added to each cryovial. These vials were then transferred to an isopropanol cryofreezing container at −80° C. Sixteen hours later, the vials were transferred to liquid nitrogen for storage. In order to increase the cell number to allow for sufficient DNA isolation for additional molecular analyses, clones in the 96-well expansion plate were grown to confluency and transferred to 24-well plates, and subsequently expanded in 6-well and 100 mm collagen-coated dishes. DNA was purified using a standard salting out procedure, as previously described (Miller et al., *Nucleic Acids Res* 16:1215, 1988).

Southern Probe Design and Labeling

The Fah specific probe was generated using primers MG2840 and MG2841 (see Table 1 for primer sequences) to amplify a 601 bp fragment of genomic Fah sequence located outside of the homologous recombination region. The Neo specific probe was generated using primers MG3159 and MG3160 to amplify a 542 bp fragment of Neo. PCR products were purified (Qiaquick; Qiagen) and 25 ng of template was labeled with $^{32}$P-dCTP using random oligonucleotides (Roche). Labeled probes were purified (Qiaquick; Qiagen) prior to hybridization.

Southern Blotting

Four μg of isolated genomic DNA was digested overnight with AflII (NEB) at 37° C. and electrophoresed on a 0.7% TAE agarose gel. Following acid depurination, the genomic digests were then transferred to a positively charged nylon membrane (Zeta-Probe; BioRad) by alkaline transfer in 0.4M NaOH. The membrane was prehybridized at 63° C. in Church buffer with 150 μg/ml fish sperm sodium salt (Amresco) for 60 minutes. For both Fah and Neo blots, the membranes were hybridized overnight in Church buffer with the $^{32}$P-labeled probe at 63° C. Membranes were subsequently washed in successive baths of 2×, 1×, and 0.1×SSC with 0.1% SDS at 63° C. for 10 minutes each. Membranes were developed by autoradiography for 2-7 days (BioMax MS; Kodak).

Preparation of Fibroblasts and Oocytes for SCNT

Porcine fetal fibroblasts were seeded in a 4-well plate and grown until contact inhibited. The cells were trypsinized until cells started to become detached and resuspended in salt-buffered NCSU-23 containing 10% FCS. Oocytes were matured in Earle's TC199-Hepes supplemented with 5 mg/mL insulin, 10 ng/mL EGF, 0.6 mM cysteine, 0.2 mM sodium pyruvate, 25 mg/mL gentamicin, 5 mg/mL FSH, and 10% porcine follicular fluid for 40 hours prior to manipulation.

SCNT, Surrogate Preparation and Embryo Transfer

All SCNT and embryo transfers were performed by Viagen (Austin, Tex.) and Exemplar Genetics (Sioux Center, Iowa) following standard protocols as described by Walker et al. (*Cloning Stem Cells* 4:105-112, 2002) and Polejaeva et al. (*Nature* 407:86-90, 2000). All reconstructed oocytes were transferred into naturally cycling gilts on the first day of standing estrus. A midline laparotomy was performed exposing the uterus following which the reconstructed embryos were transferred into the oviduct at the ampullary-isthums junction. Four gilts underwent embryo transfer with each gilt receiving 136 embryos.

Phenotype Characterization of Fah-Null Heterozygote Pigs

Histological analyses and FAH immunostaining were performed as previously described (Overturf et al., *Am J Pathol* 151:1273-1280, 1997). For Western blot analysis, liver samples were homogenized in cell lysis buffer (Cell Signaling) and 30 μg of isolated total protein were analyzed by SDS-PAGE followed by immunoblotting onto a polyvinylidene fluoride microporous membrane (Immobilon-P, Millipore). The primary antibodies against FAH and beta-Actin (Cell Signaling) were detected with a secondary HRP anti-rabbit antibody (BioRad), and imaged using a chemiluminescent substrate for detection of HRP (Thermo Scientific). FAH enzyme assays were carried out on a cytosolic fraction of homogenized liver as described previously (Grompe et al., *Genes Dev* 7:2298-237, 1993). Protein concentrations were measured by fluorometric quantification according to the manufacturer's instructions (Qubit, Invitrogen). Concentrations of succinyl acetone, tyrosine and phenylalanine were measured from dried blood spots as previously described (Turgeon et al., *Clin Chem* 54:657-664, 2008). Quantitative RT-PCR gene expression was performed as described previously (Dorrell et al., *Hepatology* 48:1282-1291, 2008). The primers for the transcripts Fah and Actb are detailed in Table 1.

TABLE 1

Primer Sequences

| Primer | Sequence | SEQ ID NO: |
| --- | --- | --- |
| MG2616 | GTAGCGAATTCGCGGCCGCGCAATG TTTTGCTAATTTCTGC | 3 |
| MG2678 | GGATAGAATTCCTGCCGGGAGGAAT AGAAGT | 4 |
| MG2619 | GTAGCAAGCTTCACGCCACAAACGT CGGAGT | 5 |
| MG2680 | GGATAAAGCTTGCGGCCGCACTCTT CCACCAGCAAGCAT | 6 |
| MG2622 | GTAGCGAATTCTGATCTACCGGGTA GGGGAGGCG | 7 |
| MG2679 | GGATAAAGCTTTAGAACTAGTGGAT CTCGAG | 8 |
| MG2844 | GAACCCAAATTCTCATGGATACC | 9 |
| MG2821 | CTAAAGCGCATGCTCCAGAC | 10 |
| MG2824 | ATTGCATCGCATTGTCTGAG | 11 |
| MG2851 | TATGCCTCCTGATCCTAAATCTTCC | 12 |
| MG2840 | CCGTTGTGTAGGCATCACATT | 13 |
| MG2841 | TAACAATTTCTGCCCCCTTG | 14 |
| MG3159 | TGCTCCTGCCGAGAAAGTAT | 15 |
| MG3160 | CAACAGATGGCTGGCAACTA | 16 |
| Fah qPCR F | ACGACCAGCCCTACATGTTC | 17 |
| Fah qPCR R | GAGTGGTGAGTGAGCTGCTG | 18 |
| Actb qPCR F | CACGCCATCCTGCGTCTGGA | 19 |
| Actb qPCR R | AGCACCGTGTTGGCGTAGAG | 20 |

Example 2

Gene Targeting and Screening in Fetal Fibroblasts

Figure 5A:
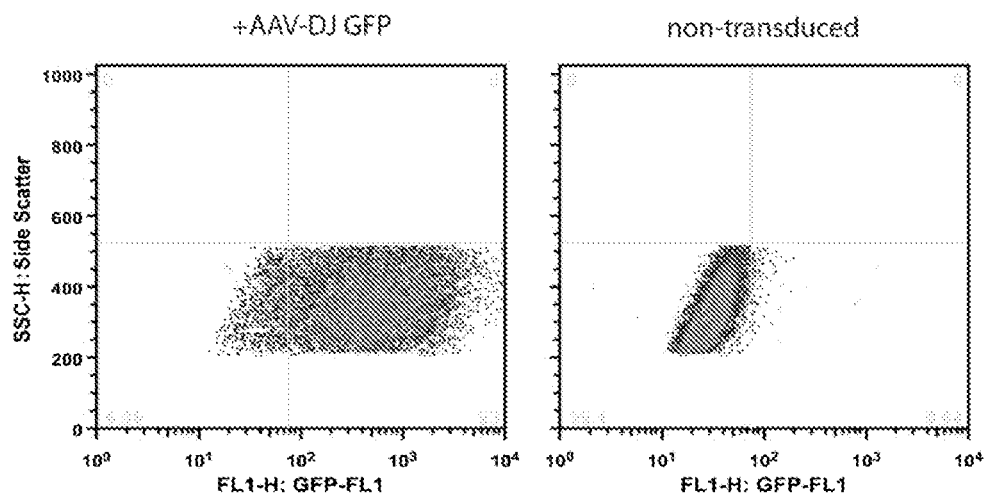
FIG. 5A is a pair of flow cytometry plots showing that the AAV-DJ GFP construct can transduce pig fetal fibroblasts. Twenty-four hours post transduction 93% of the pig fetal fibroblast were GFP-positive as detected by flow cytometry compared to non-transduced cells.
Figure 5B:
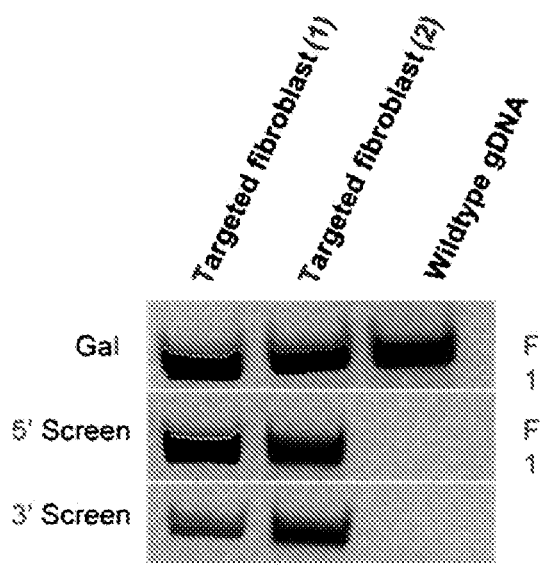
FIG. 5B is a PCR gel image showing two targeted fibroblast lines (1) and (2). Wild-type genomic DNA (gDNA) was isolated from the liver tissue of an adult pig. PCR primers designed to amplify the $\alpha 1,3$-galactosyltransferase (Gal) gene served as an internal control for the lysis procedure and PCR. Two separate sets of primers were used to amplify either the 5' or 3' end of the construct. One primer is placed in the PGK-neo cassette and the other outside the 1.5 kb targeting arm so that only properly targeted fibroblasts would yield a PCR product.
Figure 5C:
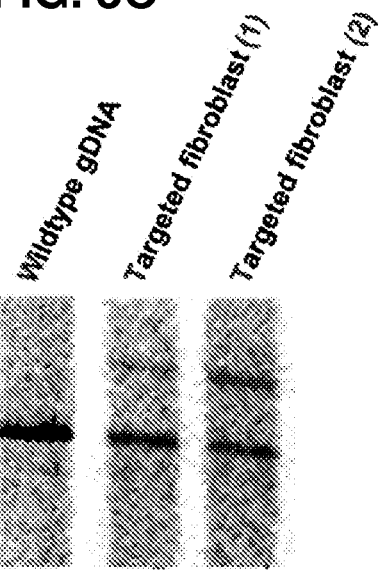
FIG. 5C is an image of Southern Blot with Fah probe. Two representative targeted lines are shown with wild-type gDNA. The lower bands represent the native wild-type Fah locus and the upper bands are the result of a 1.7 kb stop-neo cassette insertion into exon 5 of the genomic Fah gene. The Southern probe was generated from unique gDNA sequence located in intron 4 of the Fah gene outside of the homologous targeting region.

In order to be assured of success in the cloning step of this project, it was necessary to generate multiple independently targeted male and female fetal fibroblast lines. This was necessary because the cloning efficiency (ability to generate embryos by nuclear transfer) is highly variable and unpredictable from cell line to cell line. Also, it is important to establish genetic diversity in the herd of pigs outside of the Fah gene. Using PCR and Southern blot accurate targeting of multiple female and male fetal fibroblast lines was verified (FIGS. 5B-5C).

Multiple monoclonal fibroblasts were obtained from day 35 pig fetuses (Exemplar Genetics, Iowa). All screening strategies were performed on these cell lines. Culture conditions for these fibroblasts included standard media (DMEM+15% fetal calf serum) at low oxygen (1% $O_2$). Low $O_2$ is to minimize genetic damage and maximize clonability. PCR to look for Y-chromosome specific sequence was performed to identify which cell lines would generate male and female clones.

Targeting efficiencies with AAV are typically in the 0.1-1% range. Therefore, for gene targeting, 1 million cells from an individual fetus were infected on a 100 mm dish with the AAV-DJ targeting vector at a multiplicity of infection (MOI) of 500, yielding about 1,000 neo resistant clones with stable integration of the PGK-neo construct. Of these 1-10 clones were expected to have proper targeting. Using the recombinant knockout construct, targeting efficiencies were found to be much higher, in the range of 1-10%.

Six hours after infection, infected cells were trypsinized and distributed into ten 96-well collagen-coated plates (960 wells) in media that contained G418 at a concentration of 100 μg/ml, the optimal concentration for pig fetal fibroblasts. Given the presence of approximately 1,000 fetal fibroblast clones that had integrated the neo-resistance cassette, about ⅓ cells contained a clone and displayed growth. This low density ensured that each well likely contained an independent clone. After 12-14 days of growth in G418 medium, any well displaying cell growth (G418 resistance) was trypsinized and its contents were split 3 ways: 1) 20% of the cells were immediately frozen for future use (this early passage stock was expanded and sent to Exemplar Genetics to be used for cloning); 2) 70% of the cells were used for DNA extraction, PCR genotyping and detection of targeting; 3) the remaining 10% of cells were transferred to new collagen-coated 96-well plates for short-term (4-7 days) re-expansion in culture. These cells were then further expanded on 100 mm dishes for verification of gene targeting by Southern blotting.

The DNA of each clone was screened by the PCR assay described above. All fibroblasts were screened while the clones were undergoing short-term re-expansion. This means that 800-2000 PCRs were performed and analyzed in a very short period of time. If a given well had a positive result, the corresponding cells were serially passaged into a 24-well plate, than a 6-well plate, followed finally by passage into 100 mm dishes. The cells were harvested, an aliquot was frozen and the rest was processed for DNA. Southern blotting of the DNA was then used to examine the structure of the Fah locus and validate proper gene targeting. Once targeting was validated for a given clone, the immediately frozen stock was set aside for cloning. The frozen cells were shipped to Exemplar Genetics for cloning of pigs.

Currently, SCNT is the most efficient technique for production of transgenic pigs such as the FAH-deficient pigs disclosed herein. The SCNT procedure is illustrated, and the outline for creating newborn Fah$^{+/-}$ pigs from fetal fibroblasts is summarized, in FIG. 6. Briefly, mature oocytes were first isolated from female pigs. These oocytes were then cultured in vitro until shortly before the time of fusion with targeted fetal fibroblasts. Enucleated oocytes in metaphase 2 were then fused with donor fibroblasts creating the desired knockout embryos. These embryos were then transferred into activated recipient gilts. Following 15 days of progesterone therapy and 2 days of FSH-HCG (follicle-stimulating hormone-human chorionic gonadotropin) therapy, implantation was coordinated roughly 48 hours after ovulation in the recipient gilts. After an approximate 115-day gestation period, piglets arising from SCNT were born. All piglets underwent PCR and Southern blot screening to confirm their Fah$^{+/-}$ status. The results demonstrated that five of five piglets were properly targeted, as described below in Example 3.

Example 3

Production of Fah-Null Heterozygote Pigs

This example describes the production of Fah-deficient heterozygote pigs by chimeric adeno-associated virus-mediated gene knockout and somatic cell nuclear transfer.

Creation of a Targeting Vector to Disrupt the Pig Fah Gene

Figure 3:
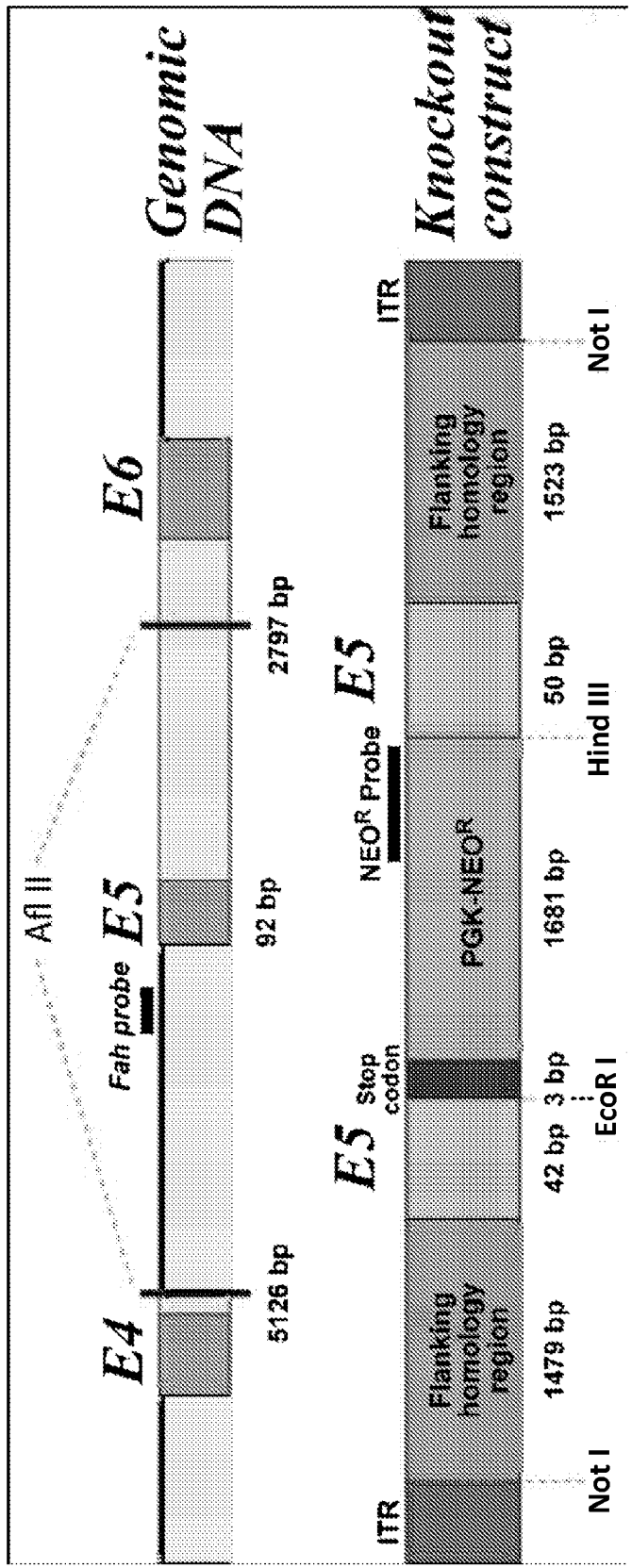
FIG. 3 is a schematic that illustrates the generation of the AAV-DJ targeting vector. The PCR primers located within exon 5 were designed to contain tails that introduced the stop codon as well as restriction sites that facilitated facile ligation into the PGK-neo expression vector. Unique restriction sites were then used for the 5' and 3' homology arms. Once the full-sized 4683 bp targeting construct had been generated, it was cloned into the backbone of an AAV2 plasmid. The approximate location of Southern blot probes is also depicted.

An Fah knockout targeting construct was created to disrupt exon 5 of the porcine Fah gene with a neomycin resistance cassette (Neo$^R$) and an in-frame stop codon (FIG. 3). The in-frame stop codon leads to nonsense-mediated mRNA decay and prematurely interrupted any translation of FAH (Maquat et al., *Cell* 104:173-176, 2001). In addition, exon 5 of the porcine Fah gene is 92 bp long and the 1.5 kb neo insertion will lead to a significant frameshift and subsequent null allele, even if the TGA-stop codon is bypassed during transcription. The Neo$^R$ inserted in the middle of exon 5 also served as a method to select for integration of the targeting vector within the genome during fibroblast expansion using G418 selection.

To improve the process of gene targeting in pigs, the chimeric AAV-DJ vector was selected to deliver the knockout construct. AAV-DJ has been shown to have high tissue tropism for fibroblasts, an essential cell type used in the pig cloning process (Grimm et al., *J Virol* 82:5887-5911, 2008; Lai et al., *Science* 295:1089-1092, 2002; Lai et al., *Nat Biotechnol* 24:435-436, 2006). In a preliminary experiment, pig fetal fibroblasts were infected with AAV-DJ containing the GFP transgene. The rAAV-DJ infected 93% of cells with the relatively low MOI of 185 (FIG. 5A). This result indicated that the chimeric AAV-DJ could be used for specific gene targeting of the Fah locus.

rAAV-DJ Vector Delivered the Fah Disruption Cassette

In pigs, cloning is performed through the process of SCNT followed by embryo transfer (Polejaeva et al., *Nature* 407:86-90, 2000); Onishi et al., *Science* 289:1188-1190, 2000; Betthauser et al., *Nat Biotechnol* 18:1055-1059, 2000). Therefore, all gene-targeting steps occurred using fetal fibroblasts and after selection and confirmation these targeted fibroblasts were used as nuclear donors in the SCNT step. Fetal fibroblasts were obtained from 35-day-old male and female pig fetuses. Primary cultures of pig fetal fibroblasts were infected with the rAAV-DJ targeting vector containing the Fah disruption cassette. Twenty-two hours after infection, fibroblasts were transferred to a number of 96-well plates and cultured under G418 selection. All wells in all plates were screened by PCR to identify wells containing Fah exon 5-targeted clones. A sensitive PCR screening strategy was created to identify target specific events using two different sets of PCR primers (FIG. 5B). The 5' PCR screen was designed using a forward primer outside the targeting region and a reverse primer for unique sequences inside our targeting construct. Similarly the 3' PCR screen utilized a forward primer for unique sequences inside our targeting construct and a reverse primer for sequences outside the targeting regions.

Targeted fibroblast clones generating PCR products obtained from the 5' and 3' PCR screen were considered double positive and were subsequently confirmed by repeat PCR, sequencing and Southern blot. Southern blot was conducted using a Fah-specific probe located outside of the homologous targeting region (FIG. 5C). The targeting frequencies obtained using the rAAV-DJ were extremely high, with an average targeting frequency of 5.4% (range=2.29-8.50%) (Table 2). Confirmed Fah-null heterozygote fibroblasts that had been in culture for 15-19 days were frozen down for SCNT. Southern blot using a neo-specific probe was used to identify clones with targeted Fah alleles that were free of other random integration events. All double positive PCR clones were also positive by Southern blot and no additional random integration events or sequence anomalies were observed.

FAH enzyme activity can be measured by fluorometric quantification. FAH converts 4-fumarlacetoacetate (FAA) to acetoacetate and fumarate. The loss of FAA is detected as decreased absorbance at 330 nm. In accordance with FAH protein levels, the Fah-null heterozygotes showed reduced FAH enzyme activity when compared to their wild-type littermates (FIG. 8E).

TABLE 3

Biochemical parameters in Fah-null heterozygote pigs

|  | Units | Wt/Wt Female n = 5 | Wt/Wt Male n = 6 | Wt/Mut Female n = 4 | Wt/Mut Male n = 5 | Normal Range |
|---|---|---|---|---|---|---|
| Succinylacetone | μmol/L | 0.96 (.05) | 0.94 (0.09) | 0.92 (0.12) | 0.91 (0.04) | <3 |
| Tyrosine | μmol/L | 105 (23) | 53 (10) | 86 (40) | 93 (19) | 55-147 |
| Phenylalanine | μmol/L | 97 (5) | 74 (17) | 77 (21) | 73 (13) | 38-137 |

Measurements were made from dried blood spot samples from 7 and 8-day old piglets for either Fah-null heterozygotes (Wt/Mut) or their wildtype siblings (Wt/Wt). Values in parentheses represent the standard error for each reading. N is the number of pigs for each group.

TABLE 2

Gene targeting frequency in donor fibroblasts

| Donor (Cell Line) | Sex | G418-resistant clones (%) | Targeted/G418-resistant clones (%) |
|---|---|---|---|
| 1 | F | 0.15 | 8.50 |
| 2 | M | 0.29 | 2.29 |

Two cell lines (1 and 2) are shown. The percentage of G418-resistent clones was obtained by dividing the number of G418-resistent clones by the number of infected cells and then multiplied by 100. Fah-null heterozygote targeted clones were those that were PCR-positive for targeted homologous recombination.

SCNT Followed by Embryo Transfer Produced Fah-Null Heterozygote Piglets

Figure 7A:
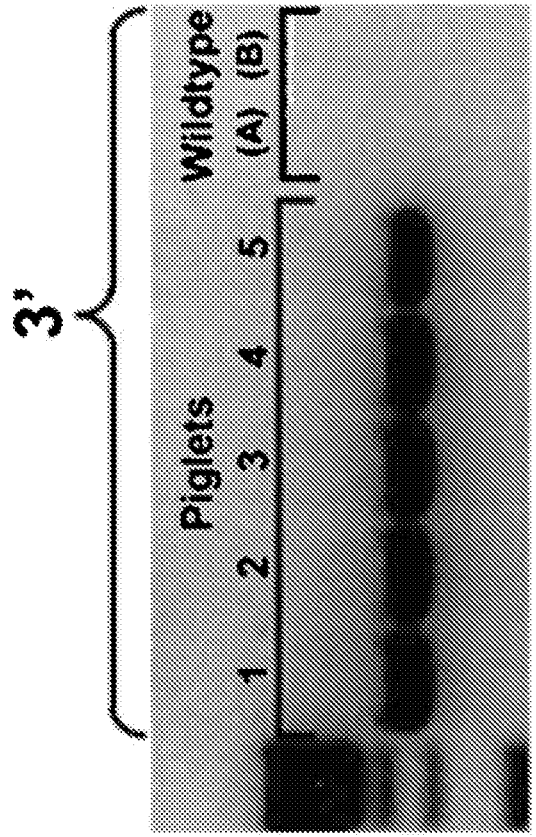
FIG. 7A is a pair of PCR gel images showing the genotyping confirmation of the newborn piglets. Five piglets are represented (numbers 1-5). Wild-type genomic DNA (WTA and WTB) was isolated from the liver of an adult pig and served as a negative control. Two separate sets of primers were used to amplify either the 5' or 3' end of the disruption cassette. One primer is placed in the PGK-neo cassette and the other outside the 1.5 kb targeting homology arm but within the Fah gene so that only properly targeted fibroblast would yield a PCR product.
Figure 7B:
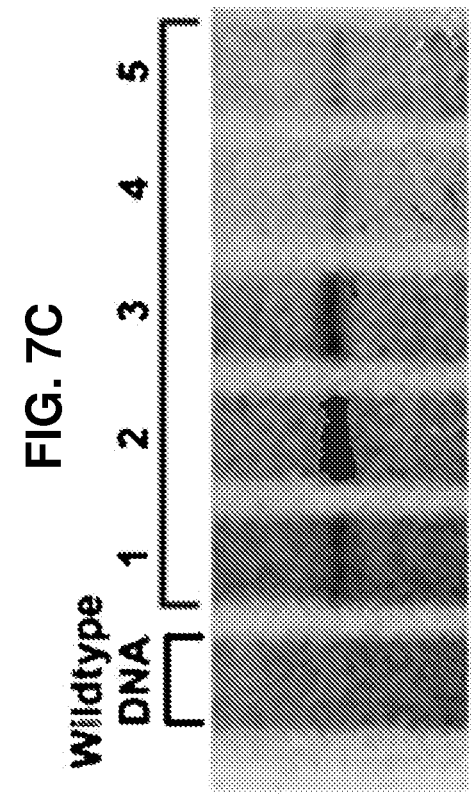
FIG. 7B is an image of a Southern blot. The lower bands represent the native wild-type Fah locus and the upper bands are the result of the insertion of the 1.7 kb disruption cassette into exon 5 of the genomic Fah gene. The Southern probe was generated from unique gDNA sequence located in intron 4 of the Fah gene outside of the homologous targeting region.
Figure 7C:
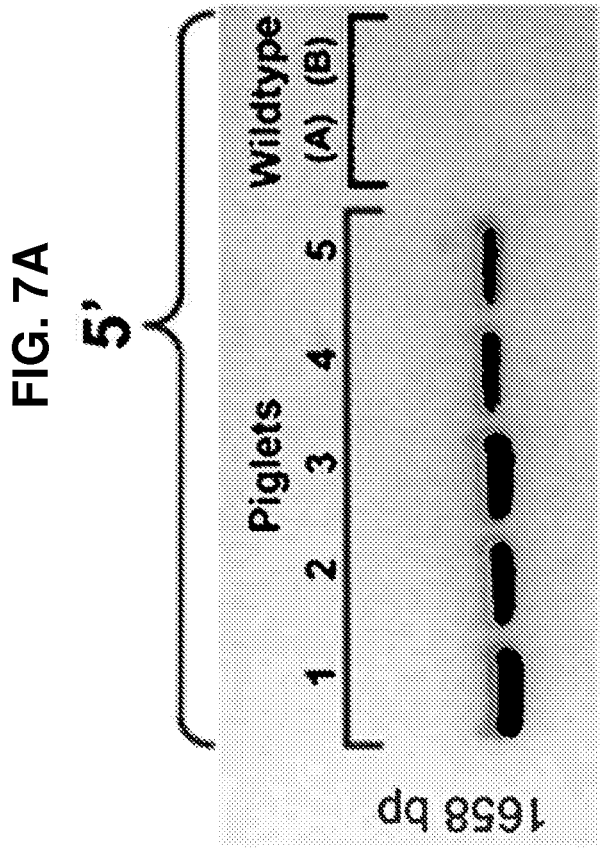
FIG. 7C is an image of a Southern blot with neo probe. A unique probe homologous to the neo cassette was generated and hybridized to detect integrated targeting constructs within the pig genome. Only a single band was ever detected, indicating a single integration within the genome.
Figure 7C:
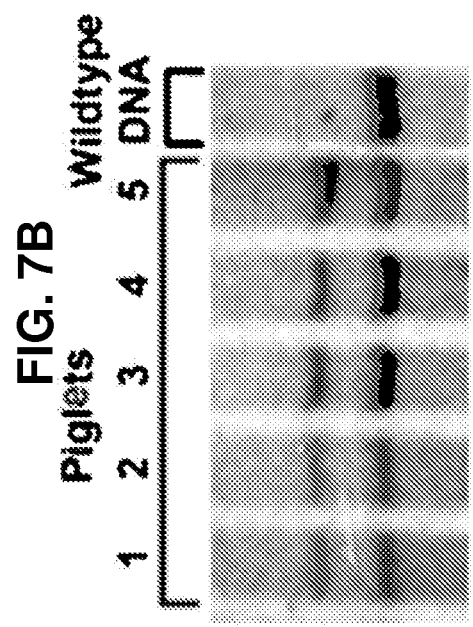

To produce heterozygote pigs, Fah-null-targeted fetal fibroblasts were used as nuclear donors for transfer to enucleated oocytes. Then to each of 4 surrogate females, 134 embryos were transferred with only one surrogate reaching full term and delivering 5 viable offspring by natural vaginal birth. PCR and Southern blot revealed that all 5 of the offspring were Fah-null heterozygotes (FIGS. 7A-7C). One of the newborn Fah-null heterozygote piglets was euthanized 24 hours after birth because of failure to thrive.

Phenotypic Characterization of Fah-Null Heterozygote Piglets

Upon reaching reproductive maturity, female Fah-null heterozygote pigs were bred to male wild-type pigs. The Fah knockout allele was inherited by newborn piglets with the expected Mendelian result: 50% of males and 55% of females carried the knockout allele. Fah-null heterozygotes were then compared to wild-type littermates. Fah-null heterozygote piglets were phenotypically normal and had normal levels of the amino acids phenylalanine and tyrosine, as well as the tyrosinemia type 1 marker succinylacetone, which indicated normal tyrosine metabolism in these animals compared to wild-type sibling controls (Table 3). In addition, H&E staining of livers of Fah-null heterozygotes appeared histologically normal and were positive for FAH by immunostaining within the hepatocytes (FIGS. 8A-8B). However, qPCR analysis revealed a 55% reduction of the Fah transcript, in addition to a reduction of the overall FAH protein seen by western blot analysis from livers of Fah-null heterozygotes when compared to wild-type animals (FIGS. 8C-8D). Finally, Example 4

Cross-Breeding Fah$^{+/-}$ Heterozygote Pigs to Produce Fah$^{-/-}$ Homozygote Pigs Fah$^{+/-}$ heterozygote pigs will be cross-bred to generate Fah$^{-/-}$ homozygote knockout animals that will effectively have hereditary tyrosinemia type 1 (HT1). HT1 is an autosomal recessive inborn error of metabolism resulting from a deficiency in FAH, the catalyst of the last step of tyrosine degradation. HT1 is characterized by the early development of cirrhosis and hepatocellular carcinoma (HCC) in humans (Russo et al., *Am J Hum Genet.* 47:317, 1990). Fah$^{-/-}$ homozygote knockout mice have been previously been created (Grompe et al., *Genes Dev* 7:2298, 1993). These animals die from liver failure unless treated with NTBC during pregnancy and immediately after birth (Grompe et al., *Nat Genet.* 10:453, 1995). When given suboptimal doses of NTBC, Fah$^{-/-}$ mice develop HCC and fibrosis (Al-Dhalimy et al., *Mol Genet Metab* 75:38, 2002; Vogel et al., *Hepatology* 39:433, 2004). The porcine model of human HT1 disclosed herein will be a significant advancement and a tool for the study of cirrhosis and HCC. This model will allow for development and testing of novel therapies used to treat cirrhotic liver failure and HCC that cannot be accomplished in other less adequate models. Importantly, the degree of liver injury in this model can be titrated with the dose of NTBC as well the timing of its administration. This has been shown in both mice and humans with the disease. Once cirrhosis or HCC have been established, the animal can be put on fully therapeutic doses of NTBC (or a similar compound) to stabilize the health of the animal for surgical procedures and other interventions.

Additionally, it is anticipated that the porcine model of HT1 disclosed herein will be amenable to repopulation by human hepatocytes, and thus represents a system for large-scale expansion of this important cell type. Furthermore, alternative therapies, such as cell transplantation either intrauterine or after birth, are still needed in the treatment of hereditary metabolic disorders such as HT1. The availability of a large animal model will facilitate development of these alternative therapies.

Cross-Breed Fah$^{+/-}$ Heterozygote Pigs and Identify Fah$^{-/-}$ Homozygotes

In order to create a Fah$^{-/-}$ homozygote, the heterozygote pigs obtained from the SCNT procedure will be cross-bred. Eight pigs, 6 females and 2 males, will be used to establish a herd of Fah$^{-/-}$ pigs. The herd will first be expanded by breeding heterozygote animals and then with genetically divergent pigs, both to increase the genetic diversity of the herd and to reduce the cost of maintaining homozygous Fah$^{-/-}$ pigs on NTBC therapy. The Fah gene status of the offspring will be determined by PCR and Southern blot based genotyping assays that have already been developed. Based on human observations and studies with transgenic Fah knockout mice, it is anticipated that the newly created Fah$^{-/-}$ homozygote pigs will die of acute liver failure early in life without the supplementation of the protective drug NTBC. In order to prevent liver failure and the development of hepatocellular carcinoma and cirrhosis, a dose of 1 mg/kg/day is used in humans and mice. Sows pregnant with Fah$^{-/-}$ fetuses will be treated with NTBC in the second half of pregnancy, starting at approximately day 55. All newborn piglets will start out on a 1 mg/kg/day dose of NTBC until genotyping has been completed. Once genotyping is complete, homozygote pigs can be studied to characterize their phenotype and the development of cirrhotic liver failure and HCC.

Correlate the Dose Response of NTBC to the Development of Liver Failure, Cirrhosis and Hepatocellular Carcinoma in Fah$^{-/-}$ Pigs Once genotyping is complete, the Fah$^{-/-}$ homozygote phenotype in pigs can be properly characterized. The suboptimal NTBC dose of 0.2 mg/kg/day allows mice to survive but develop hepatocellular carcinoma with a high penetrance rate exceeding 50% within the first six months of life. Based on these observations, the phenotype of the Fah$^{-/-}$ homozygous knockout pigs will be evaluated under the influence of NTBC at doses ranging from 0 to 1 mg/kg/day. Larger doses of NTBC will be considered if evidence of cirrhosis, hepatocellular carcinoma or liver failure occur at a dose of 1 mg/kg/day. Pigs will be treated with NTBC at a daily dose ranging from 0 to 0.1 to 0.2 to 0.5 to 1.0 mg/kg/day. The proper dose of NTBC can be titrated using plasma or urinary succinylacetone (SA) as a marker. SA is not found in normal body fluids and is pathognomonic for HT1 (Grompe, *Semin Liver Dis* 21:563, 2001). Plasma amino acid levels will be determined in order to monitor the degree of tyrosinemia. Serum alanine aminotransferase (ALT), alkaline phosphatase and bilirubin levels will be obtained to follow markers of liver injury. Blood clotting will be measured to determine the extent of synthetic liver failure. Additionally, serum alpha-fetoprotein levels will be obtained as a measure of tumor development (hepatocellular carcinoma). Homozygous study animals will be sacrificed at 3 months, 6 months, and 9 months and their liver and other internal organs will be examined for evidence of primary and metastatic tumor at autopsy (Table 4). Proper characterization of this model will be beneficial for future studies intended to use Fah$^{-/-}$ homozygous knockout pigs in the study of cirrhosis, HCC, HT-1.

TABLE 4

Dose of NTBC and study timetable

| NTBC Dose (mg/kg/day) | 3 months | 6 months | 9 months | Total # pigs |
|---|---|---|---|---|
| 0 | 2 | 0 | 0 | 2 |
| 0.1 | 2 | 2 | 2 | 6 |
| 0.2 | 2 | 2 | 2 | 6 |
| 0.5 | 2 | 2 | 2 | 6 |
| 1.0 | 2 | 2 | 2 | 6 |

Repopulation with Human Hepatocytes

Once Fah$^{-/-}$ pigs are available and the proper dose of NTBC has been determined, experiments will be performed to repopulate the Fah$^{-/-}$ liver with human hepatocytes. Two general approaches will be taken: (1) pre-immune fetal transplantation and (2) postnatal transplantation with immune suppression.

In pre-immune fetal transplantation, Fah$^{-/-}$ pigs will be bred to each other while on NTBC to generate pregnancies consisting entirely of Fah$^{-/-}$ fetuses. At approximately day 35-45 of gestation (such as day 40), the fetuses will be surgically externalized and injected with 300,000 human hepatocytes into the umbilical vein or directly into the fetal liver. At this time in gestation the immune system has not yet developed and tolerance to the human cells will develop. Immune suppressive medication will not be needed. The pregnancies will be continued on NTBC. After birth, engrafted piglets will be taken off NTBC to permit expansion of human hepatocytes.

In post-natal transplantation, Fah$^{-/-}$ piglets will be transplanted with human hepatocytes via the hepatic artery, intrasplenic injection or portal vein after birth while on NTBC. Immune suppressive drugs will be given, starting on day 2 before transplantation and then continued indefinitely. NTBC will then be stopped to permit expansion of human hepatocytes in the pig liver, as has been done successfully with mice (Azuma et al., *Nat Biotechnol* 25:903, 2007; PCT Publication No. WO 2008/151283).

Example 5

Pre-Immune Tolerization of Piglets to Human Cells

This example describes an experiment to tolerize normal piglets to human cells by fetal exposure. In this experiment, three study groups were used: (1) normal (non-tolerized) control piglets without fetal exposure to human cells (mesenchymal stem cells), and not stimulated with human stem cells; (2) non-tolerized piglets stimulated with human stem cells at 2, 4 and 6 weeks of age; and (3) piglets tolerized to human hepatocytes by fetal injection at approximately day 40 gestation and stimulated with human stem cells at 2, 4 and 6 weeks of age.

Pig fetuses from study group 3 were injected with $1 \times 10^7$ human mesenchymal stem cells (MSCs) directly into the fetal liver. At 2, 4 and 6 weeks of age, piglets from study groups 2 and 3 were injected with human $5 \times 10^7$ MSCs intraperitoneally. The immune response of each study group against human cells was evaluated by determining cytotoxicity of pig serum to human PBLs at weeks 4, 6 and 8 (baseline measurements were taken at week 2). The results are shown in FIGS. 9A-9C and summarized in Table 5 below. As expected, no cytotoxicity was observed with the control group (FIG. 9A), while serum from non-tolerized piglets (group 2) exhibited a significant immune response against the human cells (FIG. 9B). In addition, piglets from group 3 exhibited no significant immune response to the human cells following stimulation at weeks 2, 4 and 6 (FIG. 9C), demonstrating tolerization of the piglets to human cells.

TABLE 5

Tolerization of normal piglets to human stem cells by fetal exposure

| Group | Fetal exposure to human stem cells* (fetal day 40) | Stimulation using human stem cells* (weeks 2, 4 & 6) | Cytotoxicity of pig serum to human PBLs (week 8) |
|---|---|---|---|
| 1 | − | − | − |
| 2 | − | + | + |
| 3 | + | + | − |

*Mesenchymal stem cells

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of expanding human hepatocytes in vivo, comprising: (i) transplanting human hepatocytes or human hepatocyte precursor cells into a Fah-deficient pig, wherein the Fah-deficient pig is administered 2-(2-nitro-4-trifluoromethyl-benzoyl)-1,3 cyclohexanedione (NTBC) prior to transplantation at a dose sufficient to prevent liver dysfunction, and allowing the human hepatocytes to expand; or (ii) transplanting human hepatocytes or human hepatocyte precursor cells into a Fah-deficient pig fetus of a pregnant sow, wherein the sow pregnant with the Fah-deficient pig fetus is administered NTBC, and allowing the human hepatocytes to expand following birth of the Fah-deficient pig, wherein the Fah-deficient pig or pig fetus comprises homozygous disruptions in the Fah gene such that the disruption results in loss of expression of functional FAH protein, thereby expanding the human hepatocytes.

2. The method of claim 1, wherein the human hepatocytes are allowed to expand in the Fah-deficient pig for at least about 2 weeks, at least about 4 weeks, at least about 2 months, at least about 4 months, at least about 6 months or at least about 8 months.

3. The method of claim 1, wherein the Fah-deficient pig is further administered NTBC for at least two days, at least three days, at least four days, at least five days or at least six days following hepatocyte transplantation.

4. The method of claim 3, wherein NTBC is administered to the Fah-deficient pig at a dose of about 0.2 mg/kg to about 2.0 mg/kg per day.

5. The method of claim 4, wherein NTBC is administered to the Fah-deficient pig at a dose of about 1 mg/kg per day.

6. The method of claim 1, comprising transplanting human hepatocytes or human hepatocyte precursor cells into the Fah-deficient pig, wherein the Fah-deficient pig is immunosuppressed.

7. The method of claim 1, comprising transplanting human hepatocytes or human hepatocyte precursor cells into the Fah-deficient pig, wherein the human hepatocytes or human hepatocyte precursor cells are transplanted by injection into the hepatic artery, spleen or portal vein of the Fah-deficient pig.

8. The method of claim 1, comprising transplanting human hepatocytes or human hepatocyte precursor cells into the Fah-deficient pig fetus, wherein the Fah-deficient pig fetus is surgically externalized to transplant the human hepatocytes or human hepatocyte precursor cells.

9. The method of claim 8, wherein the human hepatocytes or human hepatocyte precursor cells are transplanted at about day 35 to about day 45 of gestation of the pig.

10. The method of claim 1, comprising transplanting human hepatocytes or human hepatocyte precursor cells into the Fah-deficient pig fetus, wherein the human hepatocytes or human hepatocyte precursor cells are transplanted by injection into the umbilical vein of the Fah-deficient pig fetus.

11. The method of claim 10, wherein about 100,000 to about $1 \times 10^8$ human hepatocytes or human hepatocyte precursor cells are injected.

12. The method of claim 1, comprising transplanting human hepatocytes or human hepatocyte precursor cells into the Fah-deficient pig fetus, wherein the Fah-deficient pig is administered NTBC after birth.

13. The method of claim 1, further comprising collecting the expanded human hepatocytes from the Fah-deficient pig.

14. The method of claim 13, further comprising expanding the collected human hepatocytes by serial transplantation.

15. The method of claim 1, wherein the human hepatocyte precursor cells are derived from human induced pluripotent stem (iPS) cells.

* * * * *

SEQUENCE LISTING

<160> NUMBER OF SEQ ID NOS: 20

<210> SEQ ID NO 1
<211> LENGTH: 20091
<212> TYPE: DNA
<213> ORGANISM: Sus scrofa

<400> SEQUENCE: 1

```
catgggaagt tcatcttttt tttttttttt tttttttttt tttctatttt ggctgccctg      60
tggcatatgg agttcccagg acagggatca atccgagccg tagtatcaac ctaggctgca     120
gctgtagcaa ttctggatcc ttaacccact gtgctgggca ggggatcgaa cctgtattcc     180
agggcgccca agatggagca ggaactcctg ccttccattt ctgatgaagg tagtaacttc     240
agaggtccca ggaattttgt ttggatgaga tggggcaggc ttgagacacc acaggatggc     300
ttcctaggtg agaatagtgt caggctctct gcagtcctgg gtctttcctg attgtctctg     360
atgtgaggct ctccagtaac tggttcattt ccttatttta agttgattga gcgtctgcct     420
gttccaggct tctgctgggc cctccaaggg agggaaccac gagccctgcc ctccaggttg     480
gttgatgcag cccgagagga atggacagct gggcccagtg cttctgtgtt accaccattt     540
aggcgtcagc ctgaagccca catatatgaa tgatggacgt gaatttactc ccctctgaat     600
ggttgggtgc tttgaagggc atcgtcccat tctgtggatc aggaagaagg tggtatttat     660
tgagcacctt ctatgtgcca ggtcctttgg acacatctct catttcaggg cgtcagaaag     720
ctggtcagcc tctcctgtca acagagaggt agcacaaagg gcttcccatg tatgatcttt     780
cttcctcgct gtcttagttt tagccaactc tttttttttt tttttttttt tttttttttt     840
tttttttttt ttaagggctg cacctgcagc acatggaagt tcccaggcta ggggtccaat     900
tggcctacac cacagccata gcaacaccgg atccgagccg catctgctac ctacaccaca     960
gctcctggca atgctggatc cttaacccac tgagtgaggc cagggagcga acctgcatcc    1020
tcatggatac tagttgggtt cgttacagct tagccatgat gggaactcct tttttttaaaa   1080
aactttttc attctctttt tttaaaaaaa atatttcagt gaatttttatt atatttatag    1140
ttgtagagtc atcatcacaa cctaatttta gaacatttcc atcccaaacc ctcagtccac    1200
ccctctttcc cccttacctg tcccctctgg taaccataag tttttcaaag tctgtgagtc    1260
tgtttctgtt ttgcaaataa gtgcacttgt atccttttt tagattccat atgtgatatc    1320
atatgatgtt tgtctctcac tgtcacttag catgataatt gctgtgtcca tccatgttgc    1380
tgcaaatgcc acgatttctt tcttttttacg gctgagtaac attccattgg atacatgtac    1440
cacatcttct ttatccattt ctctgtcaat ggacatttag gttgcttccc tatcttggct    1500
attgtatatg ttgcttttaat gaacattggg gtacatcttc ttttcaagtc atggtattct    1560
```

```
cctggataca tgcccaggag tgggattact ggatcatatg gtaattctat tttatttttt   1620
attttttttg ttttttttagg ccacacccg cagcatatgg aagttcccag gctaggggtc   1680
agatcggagc tgtagctgct ggcctacacc acagccttgg caatgctgga tccttaaccc   1740
actgagcatg gtcagggatt gaacctgtgt cctcatggga tgctagtcag attcattaat   1800
cgctgaacca caatgggaac tcctattttt aggtttttg aggaaactcc atactgtttt    1860
ccatcgtggc tgcaccgatt tacattccca ccagcagcgt gagagggttc ccttttctct   1920
ataccctctc tagcacttat cgtttatagg ctctctaatg atggccattc tggctggtgt   1980
aaggtggtac ctcatggtag ttttgatttg catttctcta ataattagtg atattgagca   2040
tcttttcatg tgtttggtcc tagccaactc ttaacagctt catgggcctg ggccaggctg   2100
cctggaagga agcaagagca ttcttgcaaa acctactatc tgccagccaa gccaggctca   2160
gagatgacac agaacttcgg aagcggtaag gagcccatgg accttggctg gtggaatgaa   2220
gggcacttgg ctgggcagaa gaggacagca tgctaatcga ggacattctt agtcacttct   2280
tggctgcctt ggctcatcta gccctgcct gggctgcata ttggtgagat gtctctgggc    2340
caaatgagat tacctctctg cctggagtgg ggtatccagt ccaggcctgg cccgttggcc   2400
cacgcccttg ctcactcagc cattcctcat cagcatcatt cgtgtccatg tctgggttcc   2460
agagcagggc taatttagcc cgtttcctag agtggaacaa agaagcagga gagcggcacc   2520
ttgcctttag tgggtggatg ccctcccctgc tgtggcccca tctcagccag ctctggcccc  2580
aggccaacct ggatgtgctc actggcagta gtgagcagga ttctaggaat ggtctgggct   2640
gagcatgtgg gtgggtgacc agagcagggg ccccgcttgg ctgcttgttg accttgaagc   2700
tgctcgttct gtgtttcagc gcattcacct cccaggcctc cgccacgatg catcttcctg   2760
ccgccatagg tgagtacagt ctctttacca ggacaccgag gactttaatg ggccaaggtg   2820
gctgcccagg ggtgctggtc cccgcttcct ggtgagggag ttcacagagg aggggtcctc   2880
tccccatcgg ggagctaggc cgtttctaaa ggcctgtgct ctcgcctagg ggagtcactg   2940
gctgcccaga tttgcagttg gctacctggc ttcttgtgca gcacatcact ctgtcttctc   3000
aagaggctgt ggggtgatgc tctgagctca gtctgcgagt cagcagattt gaggaaagag   3060
gccagagggt cctgaagggc ctcagttgga ccgctggct ggatgtctga ctggcatttg    3120
agtcaggaag ttggacttgt ccagactttc ttggcctgaa gcagagagag tccagatcgg   3180
ggagatcttt gcccaggagc cgggggtgct tgcctgctgg ctttgcctgg gctccgggtg   3240
ctgagaggct ggctggtccc ttggggaggc cctggcaggc cttcctgctg cctctgtccc   3300
cgtttctggg gcctgtgtcc tagcacagcc cgggaggcct gcctgggagg ataatttcct   3360
tccaaagacc ggcacacaca ggttcagtgt gttgctgacc ctcctctatg gtttgaggat   3420
taaaggcagg gagatgctgt gcttggaagc acatggctcc agttgaaatc cagggatggc   3480
gagaatggaa cgtctgcctt gtgctcagca gccgctggct cccagacttc tcctcccatc   3540
tccccacccc ctttcatttt cttctcttct ctggcttttt tatttggctg tggcatatag   3600
cagtttgatg tgggggtctc agttcccaga ccagggattg aacctgggct gcaggggcga   3660
ataggctgaa tcctaaccac aagaccacca gggacctcct ccggttctta tcttttcaga   3720
tttatttctg aagcctttcc catttatgta tttatttatt tgtgcttttt tttttttttt   3780
tttaagagct gcacctgtgg catatggagg ttcccagact agggattgaa tcggagctat   3840
agcctctggc ctacaccaca accacagcaa tgccagatct gagccacatc tgcagcctac   3900
accatagctc atggcaatgc cagatcctta acccactgag tggggccagc gattgaaccc   3960
```

```
aagtccttat ggatactact tgggctcatt agtgctgagc cacaaaggga acttcctgaa    4020
cccttcccct tttaaacatc tttttgtgtg tgtgtgtgtg tgtgtgtcct ttcttttta     4080 aggctgcacc catggcgtat ggaggttccc aggctagggg tcgaattgga gctacagctg    4140
ccagcctaca ccacggccac agcgacgctg gatcctttaag ccactgagcg aggccaggga   4200
tcgaacttgt gtcctcatgg atgctagtca gattcgttaa ccactgagcc acaacgggaa    4260
ctccttacta aggtgtaatt tacgttttcc acgatttccc caccgggagt gtacacttta    4320
atgagtttta gacaatatac cgttgtgtag gcatcacatt tgaaaacact ctgtcaccac    4380
aaaaagtctg tttgtagaca accccctgttc tcacccctgc gcaaccactg cctgtctgtg    4440
cccatagtcg cacctctcct agaatttcac atgcgtagaa tcacaccaca tgcaggtctt    4500
ctgtgtctct ctcagctgga atgtcccccc gtagtactgt tgttcttttc ctcatactgc    4560
ttttttcata acatgtattt ttttattaaa tgaaaatcag cttcgtcgtt caggaggtct    4620
ttgaaaactg ttttttaaaat tgtggtgaaa tacgcagtta cgtaacatcg actgccttta   4680
tgattgttaa gtgtccagct cagtggtatc aagtacatga catcgtctcc aatattattt    4740 ttagccttt ggaacagcag gcgctgcccc ctaaactggg ttgtaagcac ctgccggggt     4800
gtcggggtgt gtgtgtgggg gtcttcctgt ctctgcctca cagcctggcc tggacaccat    4860
cttttccaat cctttttgaag tgatcatgat gtggactggc atatagatcg tgaaaacaaa   4920 caaggggggca gaaattgtta atttttcttgt aatttggcag gaatgttctg aaatgctatg   4980
ctggttctgc ccagggctcc taccaaggca gttgggcctt ttgtaaaat gcagcaatga     5040 agtgttactt taaagtaaat gccaggagtt cccgtcttgg cgcagcagaa atgaatccaa    5100
ctaggaacca tgaggttgcg ggttcaatcc ctggcctcac tcagtgggtt aaggatccag    5160
cattgccatg agctgtggta tgtaggtcac agatgcgact cagatctggc gtggctgtgg    5220
ctgtggctgt ggcgtaggct ggtagctccg attagacccc tggcctggga acctccatat    5280
gcggtggctg cggacctcaa aagacataaa taaataaata aataaaataa aataaaaaat    5340
taaagtaaat gccagagtga cctacactta cactgcactt tatagtatgt aagacatgtt    5400
cttataactt tcgaaaagat tattatctga aaaagactca gtctctgcgt ctgccttgat    5460
cctctctaag gagcaattcc gttggcacag ccatggcagg gcaacagcaa ctcccagtag    5520
gggcaaggaa gggaattta tttgggggcct actatgtgcc aggcactatg ataaggactt    5580
gagatatatt aatccccttta ctgtatagat acgcctgtga ttggcattat tattcccaat   5640
ggagaacctg agttctagag cggcaaagga acttttccaa ggccacacac agccaggaaa    5700
cagcagagtc agaaatcaaa tctagtaggt tcgggcctgt tgtttgatat gtgggcctca    5760
ctcatgtatg aaatgagaat agaattatct acctgaaggt atagttttaa ccaggctcct    5820
tctggccctc agacctatga ttttatcaaa taaaacccac tcacttccat gtttctgggt    5880
tttttggttt gtttgttttt gttttttgtct ttttagggcc ccactcgaag tatatgcagg   5940
ttcccaggct ccagtcggag ctgtagccac cggcctatac cacagccaca gcaacatggg    6000
atccaagcca tgtctgtgac ctacgccaca gctcacggcc acgccggatc cttaacccac    6060
caaggccagg gattgaaccc acaacctcat ggacactagt caggctcatt actgctgagc    6120
cacgacggga actcccatgt ttcttgtttt taagagaaga actggaacac agacttttat    6180
tttgcttttc ttttctatat atgattgtct gtgtcttgca tgctttccat cccacaagag    6240
ggccgagggg aagcatgtcc agcttcagtc aaatgacagg aactgagcag gctgactcct    6300
```

```
gggaggggag ggcacatagg agcccaggac catcctcctt gagtctgacg ggggcaccgt   6360
ccagccgctt ttcattttcc atttttaaa aattttatg gctgcaccca cagtatatga    6420
aagttcctga gccagggatt gaatctgagc cacaggtgca acctacactg cagctgtggc  6480
catgccagat ccttgaaccc actgagcctg gcctgggatg gaacctgcac ctctgcagtg  6540
acccaagctg ctgcagtcca gattcttaac ccactatgcc acagtaggaa ctcctcactt  6600
tccttttttt tttttctttt ttagggctgc acccacagca tatagaagtt cccaggcttg  6660
gggtcaaatc agagctacag ctgccaacct cctgccacag caatgcagga tctgagccat  6720
gcctatgacc tacattacag ctcacagtaa cgccggatcc ttaacccact gagccaggga  6780
ttgaacccac agtcaggtga attaccactg agccacaacg gaacactttt gcatttttaa  6840
gatctgagga ttaatttttc acaatcagtc tgttacttat tattttttgg ctgcacttgt  6900
ggcatgagaa aattcctggg ccaaggattg aacccacgcc ccagttgcgg cctgcaccat  6960
agctggggca atactggatc cttaacccac tgcgccacga ggggacttcc tcaaacaacc  7020
tgttctggat tcatggatga acatctttt cttttttaa aattaggtat attaaaggat    7080
gcttcttttt cagtctcctt ctggtgtctc tattatttct atttccttcc tttcatttct  7140
tttgcgagtt gaattggtac ctctctcccg gtgaggattc tcctgatgcc tggtgattct  7200
cgtgctcatc tttatttgcg tagaaaatgc ctccaattag gtgtctgtgg gtgtggtttt  7260
cctgtagccg tccccaagga aagggtcaga atgtactttc ggtggggagc tctggttctg  7320
tttcccggct atggggctgc tctggtcctc tggaggcact gagtcagatc tccggaccag  7380
ctcttcaacc tgggcccccct cttctactga ggctgcttgg gaaaagctgg gtaaaggaga  7440
aattgggggg cacaggctaa tcacccagac cctctttgcc actctctctc cgtctcatgt  7500
acacacaggg ctgtgctgtt ttctggcagc cacttggctt tcagggattc cttgttattt  7560
ctggttggct gatggtacct tcttgttttc ttttttactt ttttttttttc agtgcctcac  7620 gtggggcatg tggaggttcc cagactgagg gtgaaattgg agctgtagct gccggcctac  7680
accacagcca cagcaatgcc agatccgagc tgcatctacg acctacacag ctcacagcaa  7740
cactggacac ttaacccact gagagaggcc agggatcgaa cccaaattct catggatacc  7800
agttggattt gttacccctg agccgcaact ggaactccct cttttacgt atttttaaa    7860 aaattaaagt atagttgatt tgcaatgttt tgctaatttc tgcagtacag cacagtgacc  7920
cagtcataca tatatacata tttcttttct tatagtatct tccatcatgg tctatcccca  7980
aagattggat atagtttcct ggatatagtc ggacctcatt tcttgtccat tctaaatgta  8040
atagtttgca tctactaacc ccaagctccc agttgttttc ttgtcatgga tttattcttc  8100 taaaagtat ctcagctgtt gtctctgtgc cttgggacca agatgggaag caggaacaag   8160
cctcaggtca cccctgctct aatcaaccct tgcagatttt tctctcctct catccatcct  8220
tcaccgattc catttctagt ctaggctatt ggtactggcc tacacagctt tatctattaa  8280
aagaaatttc tgggacgggg gcagtttcca ttgtgactgg gtggaaacga atccaactag  8340
taaccatgag gttgcgggtt caatccctgg ccttcctcag gggttaagga tccagcgttg  8400
ctgtgggctg tggtgtaggt cgcagacgtg gctcggatct ggcattgctg tggctgtggt  8460
gtaggctggc ggctacagct ccaatttgac ccctagcctg gaacctcca tatgttatgg    8520 gtgaggtcct ataagataa aaaaaatttt tgttttggca ggaaggagag gtttaggaaa   8580
ataaatagga agctgtccca gcttgttttt cctgcgtatt tgagcagttc actgccttgt  8640
gggagcctgt gcctacagca tgccatccac ccggttcgct cagttcttgg tcatcaccgg  8700
```

```
gcactgatga gccttgttct tggcactgag acagagtcaa acaaaacgag gcctggcctg    8760
ggcagctctg aagaggctat agtctagcag agggatacga tctgcataca tgtgaccggg    8820
acacaagtgg gccctcaagc ctgccccagg acgggctccc tcccatgagg ggattgggag    8880
gaggagaggt cctgctaggg agagtgtggc ttcacgggca aggggacac cagggacatg    8940 agggagaggc tggtcccctg gcaggcacag cttgagcaaa agcctagtga gctggcctgt    9000
gggtaggagg gaggggtggg ggtgtgtgtg tctaccattc atgtgcaaat gacattgtct    9060
gtttcagaaa gtcttgggtc cttatttctt tttcatttct cagctggaag ttctaaaatt    9120
cttaggcgaa tttgtgttgc attttgcacg gagctttggg acgcacacat gttaggcgtg    9180
tgctcctggc tcctgcctgc cctccctctg tgttctcccg ccccgcccct ccctggactg    9240
gcccttctcc gagtcctaca gcagccaggt cactgatggc ctctcccggc ctttcctccg    9300
caggtgacta cacagacttc tattcctccc ggcagcacgc cacaaacgtc ggagtcatgt    9360 tcagggcaa ggagactgca ctgatgccca attggtatgt cccagaccag tgtctggctg    9420
agttctagtt tgccttcccg tgtccagcag catgttgtcc cagggccacc aggtcctctc    9480
aggttaaaga aattgggta gaaatcagtc agtaatgatg tccccacttc tgggaaaggt    9540
ggtctcagcc tctggtcttc ttggctcagc cttggaccag ctgtgggatc gtgggcagt    9600 cctttaagct ctttgatcta gagaactgga attagatccc ctgagtcact aagatccttc    9660
cagatccttt tatttgtaag ctgtgaatcc aggttctatg ggcaagtctt ttttttttt    9720 tttggctttt gtcttttag ggcctcagtc gcgacacatg gaggttccca ggctaggggt    9780
ctaatcggag ctacagctac tggcctacac cagagccaca gcaactcggg atccgagctg    9840
tgtctgtgac ctacaccaca gctcacagca atgtgggacc cttaacccac tgagcaaagc    9900
cagggatcga accagcctcc ttgtggatac tagtcgggtt tgttcactgc tgagctgtga    9960
cgggaactcc atatgggcaa gtcttaaatc ccagctttct ccgtacttcg aatcttctga   10020
tggatgagaa tcctcaagtg gcccggggc tgtgtatttc tcaagctcac aacgggagct   10080 ccttgtatt atttgatcct cataggagtt cgtgggtccc cagggctgta cctggtagcc   10140
ccatttcaca gggggggaaa caggctcaga gaagtatcct tgcctgagtt gtccttgcct   10200
tttagaggct gcctcctaaa acccagtcaa ggccattgct caggcctaga acacaaagct   10260
gcagtttctg cccctttgtc gtgtgttggc agaggcacag cccaggccag gtgccctggg   10320
ccacacgcac agtcactgga gtgggcagag acttctgagt gtttcaggta ggctgtgcca   10380
ggaagagcag gctctctcag aaccaagaga gcagaggagg aagaaaacgg gagagagcag   10440
gttacgatcc agagaagtta agcaaccagg ccaaggttgc agaacaaggc tgaggtgaat   10500
ccaggactgc agggagcaag gccaagtgga ggaggctcgg tgcatttgct tttgcaggat   10560
aagaggacac aggctttctt tcactatgtg tgatgcaagg ggtctgtgcc ttttcttctt   10620
tatgcgtgta tccttgatta taaaggtgat agatactcac tgcgattaac ccaaacataa   10680
aatacataag gcagaacact aaaaatttaa atgtgcatcc cattggaggc ccaatctcac   10740
tttcatggct ctatcccacg gaaatgtttg tattcaagga taaagatgtt taccagcagt   10800 cttttctaaag gaagggcctg aagctggaag cagtctgaat gcttgctggt ggaagagttg   10860
aaaaattatg gtctgttcac aacctgaagt atttcacagc tattgaaagg aagatttagg   10920
atcaggaggc atatatgcat gatatatata tatatatata tattttttt tttttgtctt   10980 tttgctattt cttgggccgc tcctgcggca catggaggtt cccaggctag gggtcgaatc   11040
```

```
ggagctgtag ccttcggcct acgccagagc cagagcaacg caggatccga gccgcgtctg    11100
caacctacac cacagctcac ggcaacgccg gatcgttaac ccactgagca agggcaggga    11160
ccgaacccgc aacctcatgg ttcctagttg gattcgttaa ccactgcgcc acgacaggaa    11220
ctcctatgca tgatatatta agtgagttct catatttata aaagacaca tgaaaatata     11280 tgtacatacc tacttattag tttcctgttg tgctgtaaca aatgaccaca aacttggtgg    11340
cttaaagcaa tgggaatata ttctctcata gttcaggagg ccagaagtcc gaaatcagtc    11400
tcattgggcc aaagtcaagg tgctggctgt gctggttgct cctggaagct ccaggggaag    11460
aatccattcc cttgtcttct tcagctttca gggctcccac attccctggc tgggggcctc    11520
ttcctcagat aactccaacc tcttgcttcc atttgcaatt attctacttc ctcctttgac    11580
cttcttgcct cccctttata aggaccacct ggataatcca gaatactctc ccccatctca    11640
agatcattga cttcatcaca tctgcaggtg tcttttgctg tagacaccca ccagttccag    11700
ggcttaggat ctggagatgt tctgagggcc tattattcag cctgagacac acacacccac    11760
actcatacat gtctacatac acatacatac acctacacac atacgtacat aaagcacaca    11820
cgtacacaca gacacactta gacatacaca tgctacacgt acacagacac acttggacac    11880
acttatacat acacatatgt acatacacac atagacacac gcagacaccc ttatacatat    11940
acataataca catacagaga cacacgtaca cactcttata catacacata tatgcataca    12000
catgatgcac atacacagac acacacacat ttgcacaggc tggtaggtgc atagagaaag    12060
gtccagaata ataggctcca gaccattact cccctcaagg gaggggctgg atggacattg    12120
ctgactagct tctgtgttgt ttgaataatt gcacgtaatg taagtgcacg cagttgtatt    12180
ttataactta agccagtaag agacaaaggg ggagaagagg gagaccccca gctcactctc    12240
cagaggtcct tacttgagtg gtagttggcc ccatcgcctc cacctctcca ggttccaagt    12300
gtgcacaccc acacacgcac acatgcgttt tatttctttt tttaaagatt tttatttttt    12360
tctattgtag ttgatgtaca atgttctgtc aatttctgct gtacagcaaa gtgatccagg    12420
tgcacacatt cttttctca cattatcctc catcatgttc tatcacaagt gactagatgt     12480
agctccgtgt gctctacagc aggagcattt tatttcttta gttaacaaaa tgagaccatg    12540
ctgactgaca tttgcatttt tcccttaat ttaccattga catcgctctg tgtaaataaa     12600
cttgtctacc ccaattacc aaatagattt ttttctttct ttcttcttct ttttttgtt     12660 tcttcttttt tttttttttt agggccacac ctgcagcaca tggaggttcc caggctagga    12720
gtcgaattgg aactcaaact gctggcctac accacagcca cagcaacgtg ggatctgagc    12780
cacatctgcg gcctacacca tagctcacgg caacaccgga tccttaacca actgatcgag    12840
gcccggattg aaccttcatc ctcatggatg ctagccagat tcgttccac tgagccatga     12900 caggagctcc caaaatagat tttttggatg aggttctgca aggcaaaagc acagtgaact    12960
ggcatttatc tcaccagatg caaagaacac tagacaggga gttctcttgt ggcacagtgg    13020
gctagggatc tggcattgtc actgcagtgg ctccagtcac tgctgtgtgt aggtttgatc    13080
cctggctctg ggtacttcca cctgccatgg gtgtggcgaa agaaagaaag gaaagaaaa     13140 aaagaggaaa tacaagttgg tggtaaaagt gtatggaaat atagaggaat gagggacagc    13200
aaattccagg tgtgactccc tctagggacg gggcaggagg ggcgggaagc agagggaaga    13260
gtccaggagg actgtgaagg gggcatttca tcggcttaga aagccttttg gtgccatgtg    13320
gttatttgtt ttatatcttt ttgtatagca taaatactgc aaaataaaat tgcaaatatt    13380
taaaaaacta aaagcagcca aaagatcatc ggtgtgtatg aatggtccag aatgcaaaag    13440
```

```
gaatttatag gtaaacagtg caaacaaagc aagtttctcc caccgtgtcc ttcatcctcc    13500
tttgcctctt cagaggcaaa accatggtca gctgctcaga ttttccttca cagatatctt    13560
gcttactctc tgccaatttt ctgcatggtc actgctctct taataatttg agagactttc    13620
atatttaata gaacttaacc cttctttgtg atgcattgca catcctttcc cccagtgtga    13680
catcttttta ctttatttgc tattttcctt gatgcagaag cttgacattt ttataaagtc    13740
aaacatgtca gtcattctct ttatggcatt tacttctatg tcgtgctcgg gctttctcta    13800
tgccaagaat ttgaagtttg ggggggtatt cttttcctac tacgtgtttc agtcttactt    13860
tttacaaatt tagatcacaa tccatctctc tctctctctc ttttttttt tttttggctg    13920
tggcatgcag caacagcttg atgtgggacc tcagttccca gactggggat tgaacccaga    13980
cctctgtggt aaaagcacag aatcctaacc actgggccac caggaaactc cctggaatt    14040
cctttgtgt gtgatgtgag gtgtgggtct gtgtctgttt cctgggctgc cgtaacaaac    14100
taccatgtgt cgggtggctt gcaacaacgg aaatttatta tcctgctgtt ctggaggcca    14160
caagtccaga atcaaggttt tagcagggcc cctctccctc tgaaggctct aggggacaag    14220
cagcttcctg gcccatccag ctctggtggc tgcaggccat ccttcctggg catcactgtg    14280
gcaggctctg cctctgtctg cacatggcct tcacctcttc tctgtgtctc ttcttctgtc    14340
tctcgtaaag acacttgtca ctggatctag ggcccaactg gatggtccag gatgacctca    14400
tttcaagagc cttaacttaa tcccttttc caaataaggt caaatccata ttttcttttt    14460
tcttttctt tctttttct ttgtcttttt gccttttta gggccgcacc cacagcatat    14520
ggaggttccc aggctagggg tctaatcgaa gctgtagctg ccggcctaca ccagagccac    14580
cagcaactca ggatccatat tttctagggg tcaggatgtg gatgcacttc tggggaacca    14640
ccattcaacc ccttacaggg tctaacttat ctcgttatgc aaaaaccttt ttcaacttt    14700
agttctcatg ttctacattt taaccatata tgggtctcag cttgttcagc tggcccattc    14760
ctagcagttc cggactgttt taaattgcct tagggtcctt ggcagtcctt tcctctccta    14820
tatttctttc tttctttttt tttttttttt ttttttttc tctcttttta gggccactcc    14880
tgtggcatat ggaggttccc aggctagggg ttgaatcgga gctgcagctg ccagcctgca    14940
ccacagccac agccacagca acttgggatc ccagctacat ctgcgaccta caccgcagct    15000
cacggcaacg ccagatcctt taacccactg agcgaggcca ggaatcgaac ctgcatcctc    15060
atggatacta gtcaggttgg ctactgctga gccacagtgg aaattccacc atatttctgt    15120
cttataaaca gctcttgaca gtgttcctgc tgccctgggt gactcttctg ttctgagcat    15180
tatgatctag ttccagggtc cccttgtatt tggtagcgag ggggctaaag ggaaagtagc    15240
agaactttgc tgctggagag gcaggggttt gaatcccgac atccaccagg acttcatcct    15300
gggtcacctc agccaagcca cggatactct ccaagcctgc atttgctcag tgctgtctga    15360
taacatggtc tgctgtgcag gcagttgtg gagggaacat gaaagggaa atgataggaa    15420
aagcatgttg ccagcatgtc cccaataact ggtgctgtta ttctgcatga gtctgcatca    15480
gcaccgtatt gatgctggag acaagactag gagaaaatct cacttttccc cactatttaa    15540
ggacgttttg atttttttaaa aaaatgtaaa atgcacataa aaaatttacc accttaagca    15600
ttcaaaaatt ttttcatga ccacacccat gacacatgaa gttcctggac cagggattga    15660
ctctgagcca cagctgtaac ctacaccaca gctgtggcaa caccagatcc ttcaacccac    15720
ggtactaggc cagggatcca acccacaccc cggcagtgac ccaagcccca ctgcagtgga    15780
```

```
atttttttttt tttttttttt tttttttttt tttttttttt ttttgccttt tagggcccac    15840
tcctatggag gccacatggc atatggagat tcccaggcta ggggtctgat cagaactaca    15900
gctgccagcc cacaccagag ccacagcaat gccagatctg agctgcatct gcaatgtaca    15960
ccacagctca cagcaacgct ggatccttaa cccactaagt gaggtctggg attgaacccg    16020
taacctcata gttcctagtc agatttgttt ccactgcgcc acgacgggaa ctcctgcagt    16080
gggattctta accccttgcg ccatggtggg aactcccatc ctaagcattt ttatgtgtac    16140
agttcagtgg catcaagtac attcatactg ttgtgcaacc atcaccacca tccatctcca    16200 gaagttttc ctcttttcaa actgaaactg tagccattaa agaataactc cccatttttcc    16260 ctccaccagc ccctggcaac caccatgcta ctttctatct ctatgaattt gaatccttta    16320
ggtacctcat gtatgtggaa tcatgcaata tttgtgcttt gatgtctggc ttatttcatc    16380
agcgcagtgt cctcaagctt tatccacgtt gtggcctgtg ccattatttt ctttctttt    16440 aatgctgagc aatatccatc gtttgtaaag accacgttct gctttcccat gtattaaccg    16500
atggatgctt gggagtagct tttcatttg aaccgtgtat gtatgttgac tcccattttt    16560
tttccttctt tcttttcttt tctttcttc tttcttt cttt tcttcttc ttcttt cttt     16620 tctttcttc tttcttt ctt tcttt cttc ttcctt cct tccttcct cttccttcct       16680 tctttcctt ccttcctt ccttcctt ccttctt ctttct tc tttctttcaa             16740 gggctgcact gtggcacatg gaattctca gactaggtgt caaattgaag ctacagccgc     16800
cagcctacac cacagctcat ggcaacacct gatccttaac ccactgagca aggccaggaa    16860
tcgaactctt gacctcctgg ttacttgtca gattcgttga ctcccttttt tttagaaaaa    16920 aattatttt gcctttttag ggctgcacca cacggcacat ggaggttccc aggcgagggg    16980
tcgaattgga cctgtagccg ccagcctaca ccacatccac agtaacgtgg gatccgagct    17040
gcgaatgcaa cctacaccac agctcacagt gaaaattttt ttactatagt tgatttacaa    17100
tgttctgtcg attgttgact tctttttaat tttaaaacat tgtgaaattt atcttgcatg    17160
agtaatagag ttcatgcttt ctcgcgcttc cctccatcag gctgcatcta ccggtggcct    17220
accatggccg tgcctcctct gtcgtggtgt ctggcacccc aatccgcagg cccatgggac    17280
agatgcgccc cgatgactgt aagtgcctcc agagtccagg ccccgccgtg ctcagctctg    17340
tgtccccgca taccaagttc catgcctggc actcactaca gccccttttt ctgatgctgt    17400
tctagctaag cctcctgtgt atggtgcctg caaactcttg acatggagt tggaaatggt    17460 aagctgggtc ttggtgtttt attggcctgg ggtctgtata cacgttaggg caggagatct    17520
ctctgggatg gcagccctga gcaatgggct gttcccctgt ctcagccacg tcaatgacag    17580
ctctggcttc agaagtactg tccatcctca ctatgcacgg attctgtatt tgtgaattca    17640
cctactcgca gtcagtttgt aacccggaaa tcaatattct cagagttttg ggggtcatt    17700 caaggatacg catggactgg caaaaaattt gatttacatg ttcccacctg aggttgagca    17760
aggccatgct ctgcctttat atttcaaccg ctatcatgca aacaagtgtc ttttcagggc    17820
catgttattt tgaattttgt gcttttttgtt gacgtgcttt ttgctgtgtg gtgttcctaa    17880
gcacaagaaa gttgtgatgt gcccagtgga gaaaggtgt gcactggata agctgtattt     17940
gggacctgat agtgcccgtg gccatgagtt catgatcacg aattaacaac atgcaggccg    18000
acctcatctt cctgcacttt gctatgctgt gctttgcaga tgttgcattt ttcacatatt    18060
gaaggtttgc ggcaacccct cgtcaagcaa agtctgttgc ccacgccgtg tctctgtgtc    18120 acatttggt aattcttcta atatttcaaa cttttttcatc attattgtat ctatcatggc    18180
```

```
gatctaagat cagtggtctt tttttttttt tcttttttc ttttatggc cttttagggc    18240 cgcacttgtg gcatatggaa atttccaggc tagggggtcaa atcagagctg cagctgccgg   18300
cctacaccac ggccacagca aggccagatc tgagctgcat ctgagaccaa caccacagct    18360
cacggcagtg ctggatcctt aacctactga gcaagaccag ggctcaaacc caaatcctca    18420
tggatactag tttttaaccc tgagcacaag gggaactcct aaacataatt tttataagca    18480
ctggcaaacc tcactttatt gagatctttg cttaattgca gtgctctgga cctaaacctg    18540
aaatatcacc aaggttggcc tggtatgttg aaagaagtgt ccttaaatag aaacacacat    18600
aaagccaggc tgtgtactga ttcattgatg caaatgttgg gaccagaggc tggcaggaac    18660
ttaaccttgg atatttttt gtgggtgtgt gtgtgtgttt gccatttctt gggccgctct    18720
tgcggcatat ggaggttccc aggcgagggg tcaaataggga gctgtagcca ccggcctaca    18780
ccagagccac agcaatgcgg gatttgagcc ttgtctgcga cctacaccac agctcacggc    18840
aacgctggat ccttaaccca ctgaacaagg ccagggattg aacctgcaac tcatggttc    18900 ctagtcggat tcgttaacca ctgagccacg acgggaactc cttaaccctg attttcccc    18960 tgggagcgat ctgtctgtat ttgctaactc agtgtttctt gtgatttat gttgatggtg    19020 tttcctcaga ggctgtgggt gagggggtggg gtgtgggggtt tgccgtgaca gactctcttg   19080
gctgcatcat ggaggcagcc ttttcatttt tcatgacaca aacacaaggc ttgtgtagct    19140
gtcaaagctt aaaatgcaga gtgagaacgg gatggagggg aaggagcaga ggcgtgggag    19200
gaggtcgatg caggggccgg tgctcagggg ccgtgagggg gcctcaggag gcactggcat    19260
acagctgctc accgcttccc agggtggcta tctgtccact caggggtcct ttaggatgtt    19320
ggaaatatgg tggatttgta gccttgccag gccccggtgg ctgtccaggt ccccggctac    19380
tgtttggaac tgcctgacct ttgccctcca gggaagtgac ctggggcagc aggtcagagc    19440
cagattctca tcagctttcc cccatgtcag gctttctttg taggccctgg aacagactt    19500 ggagagccca tccccatctc caaggcccac gagcacattt ttggaatggt ccttatgaac    19560
gactggagtg gtaattatgg ggcgctgggc ttcctggagc tgtttcctgt gcacacactg    19620
ctctggggga aggctgggta cctgggacac tttcacagat gccagggatg gtcgcctggg    19680
cccggtgcca gacaaaggca gcaggtggta cagtggctga gagctcaggc ttgggtatca    19740
aacagacttc ccagctctga gctccaagtt tcttgtaagt tgaataagga taagactgga    19800
tgtcccagct aacgtttctg agctgttatg ctccaggctc tgtgctgaac accccacgtg    19860
gactcttctc ctgagtccct gcttggatcg ggccatatta ttactcccct tttataggcg    19920
aggaatgagg cacagagatt tcagctagtt gtggagctga aatttcaaac aagcagccct    19980
gtttctgagc ctgtgtcaac cctgaggcca tatacagagg aagatgggc cgcgagtccc     20040 aggaagtgtc acctcaggta taaggatgag cttccagccc cttcagggga a              20091
```

<210> SEQ ID NO 2
<211> LENGTH: 4683
<212> TYPE: DNA
<213> ORGANISM: Artificial Sequence
<220> FEATURE:
<223> OTHER INFORMATION: Synthetic nucleic acid construct

<400> SEQUENCE: 2

```
gcggccgcgc aatgttttgc taatttctgc agtacagcac agtgacccag tcatacatat      60
atacatattt cttttcttat agtatcttcc atcatggtct atccccaaag attggatata     120
```

```
gtttcctgga tatagtcgga cctcatttct tgtccattct aaatgtaata gtttgcatct      180
actaacccca agctcccagt tgttttcttg tcatggattt attcttctaa aaagtatctc      240
agctgttatc tctgtgcgtt gggaccaaga tgggaagcag aacaagcct caggttaccc       300 ctgctctaat caaccctgc agatttttct cttctctcat ccatccttca ccgcttccat       360
ttctagtcta ggctattggt actggcctac acagctttta tctattaaaa gaaatttctg      420 ggacggggc agtttccatt gtgactgggt ggaaacgaat ccaactagta accatgaggt       480
tgcaggttca atccctggcc ttcctcaggg gttaaggatc cagcgttgct gtgggctgtg       540
gtgtaggtca cagacgtggc tcggatctgg cattgctgtg gctgtggtat aggctggcgg      600
ctacagctcc gatttgaccc ctagcctggg aacctccata tgttatgggt gaggtcctac      660
aaagataaaa aaattttttg ttttggcagg aaggagaggt ttaggaaaat aaataggaag      720
ctgtcccagc ttgttttttcc tgcgtatttg agcagttcac tgccttgtgg gagcctgtgc     780
ctacagcatg ccatccaccc ggttcgctca gttcttggtc atcaccgggc actgatgagc      840
cttgttcttg gcactgagac agagtcaaac aaaacgaggc ctggcctggg cagctccgaa      900
gaggctatag tctagcagag ggataagatc tgcatacatg tgaccgggac accagtgggc      960
cctcaagcct gccccaggac gggctccctc ccatgagggg attgggagga ggagaggtcc     1020
tgctagggag agtgtggctt cacgggcaag ggggacacca gggacatgag ggagaggctg     1080
gtcccctggc aggcacagct tgagcaaaag cctagtgagc tggcctgtgg gtaggaggga     1140
ggggtggggg tgtgtgtgtc taccattcat gtgcaaatga cattgtctgt ttcagaaagt     1200
cttgggtcct tatttctttt tcatttctca gctggaagtt ctaaaattct taggcgaatt     1260
tgtgttgcat tttgcacgga gctttgggac gcacacatgt taggcgtgtg ctcctggctc     1320 ctgcctgcc tccctctggg ttctcccgcc ccgcccctcc ctggactggc ccttctccga      1380
gtcctacagc agccaggtca ctgatggcct ctcccggcct ttcctccgca ggtgactaca     1440
cagacttcta ttcctcccgg caggaattct gatctaccgg gtaggggagg cgcttttccc     1500
aaggcagtct ggagcatgcg ctttagcagc cccgctgggc acttggcgct acacaagtgg     1560
cctctggcct cgcacacatt ccacatccac cggtaggcgc caaccggctc cgttctttgg     1620
tggccccttc gcgccaccnt ctactcctcc cctagtcagg aagttccccc ccgccccgca     1680 gctgcgtcg tgcaggacgt gacaaatgga agtagcacgc tcactagtc tcgtgcagat      1740 ggacagcacc gctgagcaat ggaagcgggt aggccttttgg ggcagcggcc aatagcagct    1800
ttgctccttc gctttctggg ctcagaggct gggaaggggt gggtccgggg gcgggctcag    1860
gggcgggctc aggggcgggg cgggcgcccg aaggtcctcc ggaggcccgg cattctgcac    1920
gcttcaaaag cgcacgtctg ccgcgctgtt ctcctcttcc tcatctccgg gcctttcgac    1980
ctgcagccaa tatgggatcg gccattgaac aagatggatt gcacgcaggt tctccggccg    2040
cttgggtgga gaggctattc ggctatgact gggcacaaca gacaatcggc tgctctgatg    2100
ccgccgtgtt ccggctgtca gcgcaggggc gcccggttct ttttgtcaag accgacctgt    2160
ccggtgccct gaatgaactg caggacgagg cagcgcggct atcgtggctg gccacgacgg    2220
gcgttccttg cgcagctgtg ctcgacgttg tcactgaagc gggaagggac tggctgctat    2280
tgggcgaagt gccggggcag gatctcctgt catctcacct tgctcctgcc gagaaagtat    2340
ccatcatggc tgatgcaatg cggcggctgc atacgcttga tccggctacc tgcccattcg    2400
accaccaagc gaaacatcgc atcgagcgag cacgtactcg gatggaagcc ggtcttgtcg    2460
atcaggatga tctggacgaa gagcatcagg ggctcgcgcc agccgaactg ttcgccaggc    2520
```

```
tcaaggcgcg catgcccgac ggcgatgatc tcgtcgtgac ccatggcgat gcctgcttgc    2580
cgaatatcat ggtggaaaat ggccgctttt ctgattcat cgactgtggc cggctgggtg     2640
tggcggaccg ctatcaggac atagcgttgg ctacccgtga tattgctgaa gagcttggcg    2700
gcgaatgggc tgaccgcttc ctcgtgcttt acggtatcgc cgctcccgat cgcagcgca    2760 tcgccttcta tcgccttctt gacgagttct tctgagggga tcaattctct agagctcgct   2820
gatcagcctc gactgtgcct tctagttgcc agccatctgt tgtttgcccc tccccgtgc    2880 cttccttgac cctggaaggt gccactccca ctgtcctttc taataaaat gaggaaattg    2940 catcgcattg tctgagtagg tgtcattcta ttctgggggg tggggtgggg caggacagca   3000
agggggagga ttgggaagac aatagcaggc atgctgggga tgcggtgggc tctatggctt   3060
ctgaggcgga aagaaccagc tggggctcga gatccactag ttctaaagct tcacgccaca   3120
aacgtcggag tcatgttcag gggcaaggag actgcactga tgcccaattg gtatgtccca   3180
gaccagtgtc tggctgagtt ctagtttgcc ttcccgtgtc cagcagcatg ttgtcccagg   3240
gccaccaggt cctctcaggt taaagaaatt ggggtagaaa tcagtcagta atgatgtccc   3300
cacttctggg aaaggtggtc tcagcctctg gtcttcttgg ctcagccttg gaccagctgt   3360
gggatcgtgg ggcagtcctt taagctcttt gatctagaga actggaatta gatcccctga   3420
gtcactaaga tccttccaga tccttttatt tgtaagctgt gaatccaggt tctatgggca   3480
agtctttttt ttttttttt ggcttttgtc tttttagggc ctcagtcgcg acacatggag    3540
gttcccaggc tagggtcta atcggagcta cagctactgg cctacaccag agccacagca    3600
actcgggatc cgagctgtgt ctgtgaccta caccacagct cacagcaatg tgggacccct   3660
aacccactga gcaaagccag ggatcgaacc agcctccttg tggatactag tcgggtttgt   3720
tcactgctga gctgtgacgg gaactccata tgggcaagtc ttaaatccca gctttctccg   3780
tacttcgaat cttctgatgg atgagaatcc tcaagtgggc ccggggctgt gtatttctca   3840
agctcacaac gggagctcct tgtatttatt tgatcctcat aggagttcgt gggtccccag   3900
ggctgtacct ggtagcccca tttcacaggg ggggaaacag gctcagagaa gtatccttgc    3960
ctgagttgtc cttgcctttt agaggctgcc tcctaaaacc cagtcaaggc cattgctcag    4020
gcctagaaca caaagctgca gtttctgccc ctttgtcgtg tgttggcaga ggcacagccc    4080
aggccaggtg ccctgggcca cacgcacagt cactggagtg ggcagagact tctgagtgtt   4140
tcaggtaggc tgtgccagga agggcaggct ctctcagaac caagagagca gaggaggaag    4200
aaaacgggag agagcaggtt acgatccaga gaagttaagc aaccaggcca aggttgcaga   4260
acaaggctga ggtgaatcca ggactgcagg gagcaaggcc aagtggagga ggctcggtgc   4320
atttgctttt gcaggataag aggacacagg ctttctttca ctatgtgtga tgcaagggggt  4380 ctgtgccttt tcttctttat gcgtgtatcc ttgattataa aggtgataga tactcactgc    4440
gattaaccca aacataaaat acataaggca gaacactaaa aatttaaatg tgcatcccat    4500
tggaggccca atctcacttt catggctcta tcccacggaa atgtttgtat tcaaggataa    4560
agatgtttac cagcagtctt tctaaaggaa gggcctgaag ctggaagcag tctgaatgct    4620
tgctggtgga agagtgcggc cgcaggaacc cctagtgatg gagttggcca ctccctctct    4680
gcg                                                                  4683
```

<210> SEQ ID NO 3
<211> LENGTH: 41
<212> TYPE: DNA

<213> ORGANISM: Artificial Sequence
<220> FEATURE:
<223> OTHER INFORMATION: Synthetic oligonucleotide

<400> SEQUENCE: 3
gtagcgaatt cgcggccgcg caatgttttg ctaatttctg c         41

<210> SEQ ID NO 4
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 4
ggatagaatt cctgccggga ggaatagaag t                    31

<210> SEQ ID NO 5
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 5
gtagcaagct tcacgccaca aacgtcggag t                    31

<210> SEQ ID NO 6
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 6
ggataaagct tgcggccgca ctcttccacc agcaagcat            39

<210> SEQ ID NO 7
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 7
gtagcgaatt ctgatctacc gggtagggga ggcg                 34

<210> SEQ ID NO 8
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 8
ggataaagct ttagaactag tggatctcga g                    31

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 9
gaacccaaat tctcatggat acc                             23

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
ctaaagcgca tgctccagac                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
attgcatcgc attgtctgag                                                    20

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12
tatgcctcct gatcctaaat cttcc                                              25

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 13
ccgttgtgta ggcatcacat t                                                  21

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
taacaatttc tgcccccttg                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
tgctcctgcc gagaaagtat                                                    20

<210> SEQ ID NO 16
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 16
caacagatgg ctggcaacta                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
acgaccagcc ctacatgttc                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
gagtggtgag tgagctgctg                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
cacgccatcc tgcgtctgga                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
agcaccgtgt tggcgtagag                                                  20
```